(12) United States Patent
Greenhouse et al.

(10) Patent No.: US 7,863,305 B2
(45) Date of Patent: *Jan. 4, 2011

(54) 3-AMINO-1-ARYLPROPYL INDOLES AS MONOAMINE REUPTAKE INHIBITORS

(75) Inventors: Robert Greenhouse, Newark, CA (US); Saul Jaime-Figueroa, Fremont, CA (US); Lubica Raptova, Sunnyvale, CA (US); Deborah Carol Reuter, Los Gatos, CA (US); Karin Ann Stein, Mountain View, CA (US); Robert Weikert, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 1508 days.

This patent is subject to a terminal disclaimer.

(21) Appl. No.: 11/142,076

(22) Filed: Jun. 1, 2005

(65) Prior Publication Data
US 2006/0025467 A1 Feb. 2, 2006

Related U.S. Application Data

(60) Provisional application No. 60/576,044, filed on Jun. 1, 2004.

(51) Int. Cl.
| A61K 31/404 | (2006.01) |
| A61K 31/416 | (2006.01) |
| A61K 31/4184 | (2006.01) |
| A61K 31/423 | (2006.01) |
| A61K 31/428 | (2006.01) |
| C07D 209/04 | (2006.01) |
| C07D 231/56 | (2006.01) |
| C07D 235/04 | (2006.01) |
| C07D 263/54 | (2006.01) |
| C07D 277/64 | (2006.01) |

(52) U.S. Cl. ............... 514/367; 514/375; 514/394; 514/405; 514/412; 548/152; 548/217; 548/302.7; 548/452; 549/49; 549/462

(58) Field of Classification Search ............ 548/152, 548/217, 302.7, 452; 549/49, 462; 514/367, 514/375, 394, 405, 412
See application file for complete search history.

(56) References Cited

U.S. PATENT DOCUMENTS

| 2,708,197 | A | 5/1955 | Speeter |
| 2,752,358 | A | 6/1956 | Ehrhart et al. |
| 2,984,670 | A | 5/1961 | Szmuszkovicz et al. |
| 2005/0222148 | A1 | 10/2005 | Kim et al. |
| 2006/0025467 | A1 | 2/2006 | Greenhouse et al. |

FOREIGN PATENT DOCUMENTS

| DE | 849 108 | | 9/1952 |
| EP | 0 509 402 | A1 | 10/1992 |
| EP | 0 534 343 | A | 3/1993 |
| EP | 0 600 830 | A1 | 11/1993 |
| EP | 0 775 694 | A2 | 5/1997 |
| EP | 0 887 348 | A1 | 12/1998 |
| FR | 2 814 073 | A1 | 3/2002 |
| GB | 705652 | | 3/1954 |
| GB | 992731 | | 5/1965 |
| JP | 3-14562 | A2 | 1/1991 |
| WO | WO 94/12478 | A1 | 6/1994 |
| WO | WO 96-40094 | A1 | 12/1996 |
| WO | WO 97/10219 | A1 | 3/1997 |
| WO | WO 97/46511 | A1 | 12/1997 |
| WO | WO 98/43942 | A1 | 10/1998 |
| WO | WO 99/16755 | A1 | 4/1999 |
| WO | WO 99/21553 | A1 | 5/1999 |
| WO | WO 99/21557 | A1 | 5/1999 |
| WO | WO 00/02551 | A2 | 1/2000 |
| WO | WO 01/32622 | A1 | 5/2001 |
| WO | WO 02/069965 | A1 | 9/2002 |

OTHER PUBLICATIONS

CAPLUS Accession No. 1955:24163, abstract of GB 705652.*
Caplus Accession No. 1955:24163, abstract of GB 705652.*
Ganellin, C.R., et al., "Aminoalkylation of Metal Derivatives of Indole: Part III." J. Chem Society, Section C (Organic), vol. 11, 1969, pp. 1537-1540.
Lindner, E., "Über ein neues Antihistaminicum, das-1-Phenyl-1-Pyridyl-(2)-3-dimethylaminopropan und sein Salz mit der p-Aminosalicylsäure (A vil)", Naunyn-Schmiedbergs Archiv für Pharmakologie und Experimentelle Pathologie, vol. 211, 1950, pp. 328-344.
Kraxner, J. et. al., "Azepino- and Diazepinoindoles: Synthesis and Dopamine Receptor Binding Profiles," Archiv der Pharmazie, vol. 333 (9) 2000 pp. 287-292.
Schmidt, A. M. et. al., "Synthesis of Pharmacologically Relevant Indoles with Amine Side Chains via Tandem Hydroformylation/ Fischer Indole Synthesis," J. Organic Chem. vol. 70 (14) 2005 pp. 5528-5535.

* cited by examiner

Primary Examiner—Rei-Tsang Shiao
Assistant Examiner—Janet L Coppins
(74) Attorney, Agent, or Firm—Robert C. Hall

(57) ABSTRACT

Compounds of formula I:

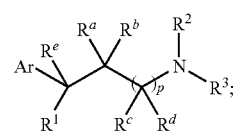

or pharmaceutically acceptable salts, solvates or prodrugs thereof,
wherein p, Ar, $R^1$, $R^2$, $R^3$, $R^a$, $R^b$, $R^c$, $R^d$ and $R^e$ are defined herein. Also provided are pharmaceutical compositions, methods of using, and methods of preparing the compounds.

28 Claims, No Drawings

3-AMINO-1-ARYLPROPYL INDOLES AS MONOAMINE REUPTAKE INHIBITORS

CROSS REFERENCE TO RELATED APPLICATIONS

This application is entitled to the benefit of U.S. Provisional Patent Application Ser. No. 60/576,044 filed on Jun. 1, 2004, the disclosure of which is incorporated herein by reference.

FIELD OF THE INVENTION

This invention pertains to compounds and methods useful for treatment of diseases associated with monoamine reuptake inhibitors. More particularly, this invention provides compounds usable as dual reuptake inhibitors of serotonin and norepinephrin, as well as related methods for making and using such compounds.

BACKGROUND OF THE INVENTION

Monoamine deficiency has been long been linked to depressive, anxiolytic and other disorders (see, e.g.: Charney et al., *J. Clin. Psychiatry* (1998) 59, 1-14; Delgado et al., *J. Clin. Psychiatry* (2000) 67, 7-11; Resser et al., *Depress. Anxiety* (2000) 12 (Suppl 1) 2-19; and Hirschfeld et al., *J. Clin. Psychiatry* (2000) 61, 4-6. In particular, serotonin (5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Masand et al., *Harv. Rev. Psychiatry* (1999) 7, 69-84). Noradrenaline or norepinephrin reuptake inhibitors such as reboxetine, atomoxetine, desipramine and nortryptyline have provided effective treatments for depressive, attention deficit and hyperactivity disorders (Scates et al., *Ann. Pharmacother.* (2000) 34, 1302-1312; Tatsumi et al., *Eur. J. Pharmacol.* (1997) 340, 249-258).

Enhancement of serotonin and norepinephrine neurotransmission is recognized to be synergistic in the pharmacotherapy of depressive and anxiolytic disorders, in comparison with enhancement of only serotonin or norepinephrine neurotransmission alone (Thase et al., *Br. J. Psychiatry* (2001) 178, 234, 241; Tran et al., *J. Clin. Psychopharmacology* (2003) 23, 78-86). Dual reuptake inhibitors of both serotonin and norepinephrine, such as duloxetine, milnacipran and venlafaxine are currently under development for treatment of depressive and anxiolytic disorders (Mallinckrodt et al., *J. Clin. Psychiatry* (2003) 5(1) 19-28; Bymaster et al., *Expert Opin. Investig. Drugs* (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behaviour, attention deficit disorders, panic attacks, social phobias, eating disorders such as obesity, anorexia, bulimia and "binge-eating", stress, hyperglycaemia, hyperlipidemia, non-insulin-dependent diabetes, seizure disorders such as epilepsy, and treatment of conditions associated with neurological damage resulting from stroke, brain trauma, cerebral ischaemia, head injury and haemorrhage. Dual reuptake inhibitors of serotonin and norepinephrine also offer potential treatments for disorders and disease states of the urinary tract, and for pain and inflammation.

There is accordingly a need for compounds that are effective as serotonin reuptake inhibitors, norepinephrine reuptake inhibitors, and/or dual reuptake inhibitors of serotonin and norepinephrine, as well as methods of making and using such compounds in the treatment of depressive, anxiolytic, genitourinary, and other disorders. The present invention satisfies these needs.

SUMMARY OF THE INVENTION

The invention provides compounds of formula I:

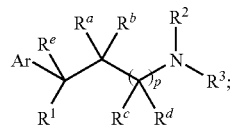

or pharmaceutically acceptable salts thereof, wherein:
p is 1 or 2;
Ar is:
  indolyl selected from indol-1-yl, indol-2-yl and indol-3-yl, each optionally substituted;
  2,3-dihydroindolyl selected from 2,3-dihydroindol-1-yl, 2,3-dihydroindol-2-yl and 2,3-dihydroindol-3-yl, each optionally substituted;
  indazolyl selected from indazol-1-yl, indazol-2-yl and indazol-3-yl, each optionally substituted;
  benzimidazolyl selected from benzimidazol-1-yl and benzimidazol-2-yl, each optionally substituted;
  benzofuranyl selected from benzofuran-2-yl and benzofuran-3-yl, each optionally substituted;
  benzothiophenyl selected from benzothiophen-2-yl and benzothiophen-3-yl, each optionally substituted;
  optionally substituted benzoxazol-2-yl; or
  optionally substituted benzothiazol-2-yl;
$R^1$ is:
  aryl selected from phenyl and naphthyl, each optionally substituted;
  heteroaryl selected from thienyl, furanyl, pyridinyl, pyrimidinyl, pyridazinyl, pyrazinyl, oxazolyl, thiazolyl, isoxazolyl, isothiazolyl, imidazolyl, pyrazolyl quinolinyl and isoquinolinyl, each optionally substituted;
  optionally substituted arylalkyl;
  optionally substituted heteroarylalkyl;
  cycloalkyl;
  cycloalkylmethyl; or
  branched alkyl;
$R^2$ and $R^3$ each independently is:
  hydrogen;
  alkyl;
  hydroxyalkyl;
  alkoxyalkyl;
  benzyl;
  or $R^2$ and $R^3$ together with the nitrogen to which they are attached may form an optionally substituted four to seven membered ring that optionally includes an additional heteroatom selected from N, O and S;
$R^a$ is:
  hydrogen;
  fluoro; or
  alkyl;

$R^b$ is:
- hydrogen;
- alkyl;
- hydroxy;
- alkoxy;
- fluoro; or
- hydroxyalkyl;

$R^c$ and $R^d$ each independently is:
- hydrogen; or
- alkyl;

or one of $R^2$ and $R^3$ together with one of $R^a$ and $R^b$ and the atoms to which they are attached may form a five or six membered ring that optionally includes an additional heteroatom selected from O, N and S;

or on of $R^2$ and $R^3$ together with one of $R^c$ and $R^d$ together with the atoms to which they are attached may form a four to six membered ring that optionally includes an additional heteroatom selected from O, N and S; and $R^e$ is hydrogen or alkyl;

provided that when p is 1, $R^a$, $R^b$, $R^c$ and $R^d$ are hydrogen, Ar is indol-1-yl and $R^1$ is phenyl, then $R^2$ and $R^3$ are not simultaneously methyl and do not form a six-membered ring, and further provided that when Ar is indol-3-yl, p is 1, $R^a$, $R^b$, $R^c$ and $R^d$ are hydrogen, and $R^1$ is phenyl or 3-methoxyphenyl, then $R^2$ and $R^3$ are not simultaneously hydrogen.

The invention also provides pharmaceutical compositions, methods of using, and methods of preparing the aforementioned compounds.

The methods comprise, in certain embodiments:
reacting an indole a:

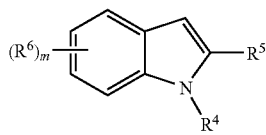

with an aldehyde b:

in the presence of 2,2-dimethyl-[1,3]dioxane-4,6-dione, to form a compound c:

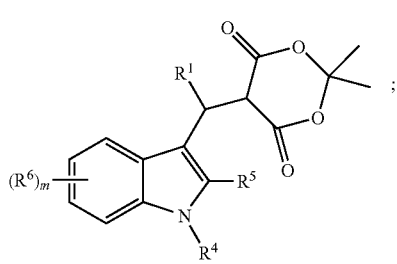

reacting the compound c with an amine d:

in the presence of pyridine, to form a compound of formula e:

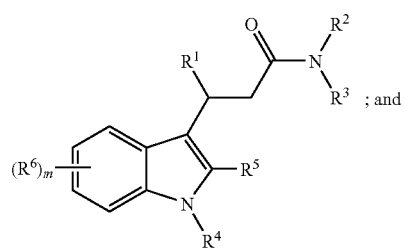

reducing compound e to form a compound of formula VI:

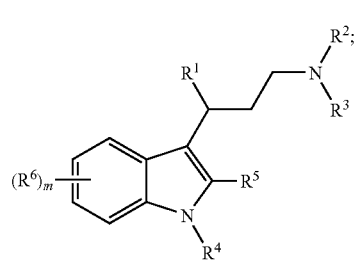

wherein m, $R^1$, $R^2$, $R^3$, $R^4$, $R^5$ and $R^6$ are as defined herein.

In other embodiments, the subject methods comprise:
heating a compound of formula VI wherein $R^5$ is hydrogen, in the presence of polyphosphoric acid, to form a compound of formula V:

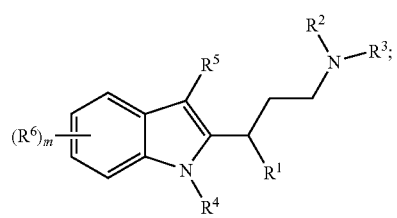

wherein m, $R^1$, $R^2$, $R^3$, $R^4$, $R^5$ and $R^6$ are as defined herein.

In still other embodiments the subject methods comprise:
reacting an indole k

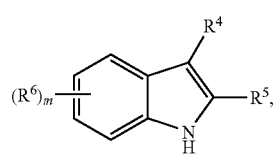

with an acrylic estr l

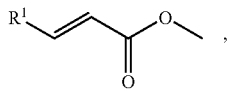

to form an indole propionic ester m

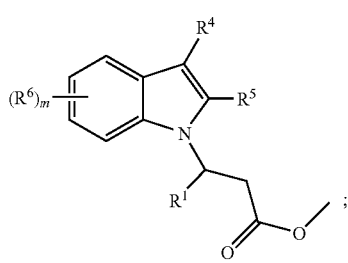

reducing indole propionic ester m to afford an indole propanol n

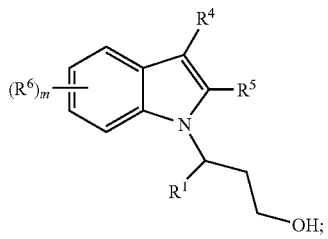

treating indole propanol n with methanesulfonyl chloride, followed by lithium chloride, to provide an indole propyl chloride o

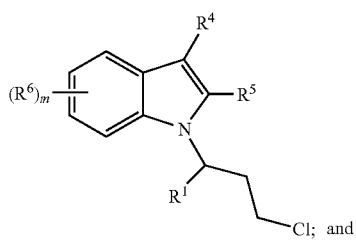

reacting indole propyl chloride o with an amine d

HNR²R³  d in the presence of sodium iodide, to yield a compound of formula IV;

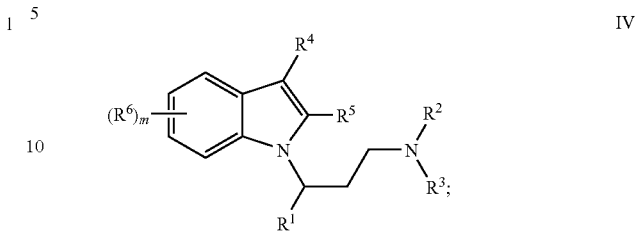

wherein m, R¹, R², R³, R⁴, R⁵ and R⁶ are as defined herein.

In yet other embodiments, the methods may comprise:
reacting an aminopropyl compound f

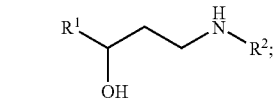

with trifluoroacetic anhydride to produce a trifluoroacetate compound g

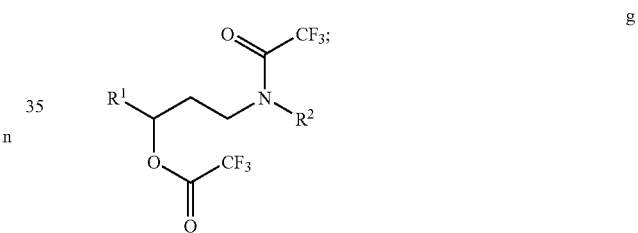

reacting trifluoracetate compound g with indole compound h

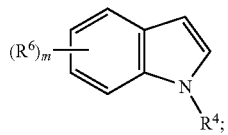

and
treating the resulting compound with base to afford a compound of formula VI;

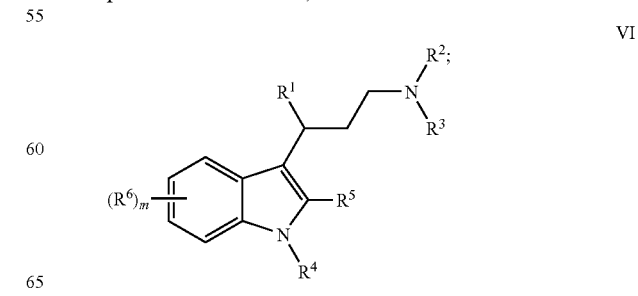

wherein m, R¹, R², R³, R⁴, R⁵ and R⁶ are as defined herein.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfonyloxy" means a moiety of the formula $R^a$—$SO_2$—O—, where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R", where R' is alkylene and R" is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, $NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" and "heteroaralkyl", which may be used interchangeably, mean a radical-$R^aR^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzofuranyl such as benzofuran-2-yl and benzofuran-3-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl)" or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elsevier, N.Y.-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin and norepinephrine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract.

"Depression" as used herein includes, but is not limited to, major depression, long-term depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v. 4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For convenience, the IUPAC numbering of the positions of representative indole and related compounds described herein is shown by the formula:

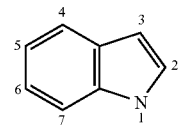

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

The invention provides compounds of formula I:

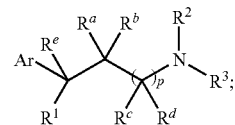

or pharmaceutically acceptable salts thereof, wherein:
p is 1 or 2;
Ar is:
  indolyl selected from indol-1-yl, indol-2-yl and indol-3-yl, each optionally substituted;
  2,3-dihydroindolyl selected from 2,3-dihydroindol-1-yl, 2,3-dihydroindol-2-yl and 2,3-dihydroindol-3-yl, each optionally substituted;
  indazolyl selected from indazol-1-yl, indazol-2-yl and indazol-3-yl, each optionally substituted;
  benzimidazolyl selected from benzimidazol-1-yl and benzimidazol-2-yl, each optionally substituted;
  benzofuranyl selected from benzofuran-2-yl and benzofuran-3-yl, each optionally substituted;
  benzothiophenyl selected from benzothiophen-2-yl and benzothiophen-3-yl, each optionally substituted;
  optionally substituted benzoxazol-2-yl; or
  optionally substituted benzothiazol-2-yl;
$R^1$ is:
  aryl selected from phenyl and naphthyl, each optionally substituted;
  heteroaryl selected from thienyl, furanyl, pyridinyl, pyrimidinyl, pyridazinyl, pyrazinyl, oxazolyl, thiazolyl, isoxazolyl, isothiazolyl, imidazolyl, pyrazolyl quinolinyl and isoquinolinyl, each optionally substituted;
  optionally substituted arylalkyl;
  optionally substituted heteroarylalkyl;
  cycloalkyl;
  cycloalkylmethyl; or
  branched alkyl;
$R^2$ and $R^3$ each independently is:
  hydrogen;
  alkyl;
  hydroxyalkyl;
  alkoxyalkyl;
  benzyl;
  or $R^2$ and $R^3$ together with the nitrogen to which they are attached may form an optionally substituted four to seven membered ring that optionally includes an additional heteroatom selected from N, O and S;

$R^a$ is:
hydrogen;
fluoro; or
alkyl;

$R^b$ is:
hydrogen;
alkyl;
hydroxy;
alkoxy;
fluoro; or
hydroxyalkyl;

$R^c$ and $R^d$ each independently is:
hydrogen; or
alkyl;

or one of $R^2$ and $R^3$ together with one of $R^a$ and $R^b$ and the atoms to which they are attached may form a five or six membered ring that optionally includes an additional heteroatom selected from O, N and S;

or on of $R^2$ and $R^3$ together with one of $R^c$ and $R^d$ together with the atoms to which they are attached may form a four to six membered ring that optionally includes an additional heteroatom selected from O, N and S; and $R^e$ is hydrogen or alkyl;

provided that when p is 1, $R^a$, $R^b$, $R^c$ and $R^d$ are hydrogen, Ar is indol-1-yl and $R^1$ is phenyl, then $R^2$ and $R^3$ are not simultaneously methyl and do not form a six-membered ring, and further provided that when Ar is indol-3-yl, p is 1, $R^a$, $R^b$, $R^c$ and $R^d$ are hydrogen, and $R^1$ is phenyl or 3-methoxyphenyl, then $R^2$ and $R^3$ are not simultaneously hydrogen.

It is to be understood that the scope of this invention encompasses not only the various isomers which may exist but also the various mixture of isomers which may be formed. Furthermore, the scope of the present invention also encompasses solvates and salts of compounds of formula I.

In certain embodiments of formula I, p is 1.

In many embodiments of formula I, $R^a$, $R^b$, $R^c$ and $R^d$ are hydrogen.

In many embodiments of formula I, $R^e$ is hydrogen.

In certain embodiments of formula I, $R^1$ is optionally substituted aryl, preferably optionally substituted phenyl or optionally substituted naphthyl.

In certain embodiments of formula I, $R^1$ is optionally substituted heteroaryl. In such embodiments $R^1$ may be pyridinyl, pyrimidinyl, pyridazinyl, pyrazinyl, thienyl or quinolinyl, each optionally substituted. Preferably, when $R^1$ is optionally substituted heteroaryl, $R^1$ is pyridinyl, pyrimidinyl, pyrazinyl or pyridazinyl, eacho optionally substituted. More preferably, $R^1$ may be optionally substituted pyridinyl, such as optionally substituted pyridin-2-yl, optionally substituted pyridin-3-yl or optionally substituted pyridin-4-yl, and more specifically optionally substituted pyridin-2-yl or optionally substituted pyridin-3-yl.

In certain embodiments of formula I, $R^1$ is optionally substituted phenyl.

In certain embodiments of formula I, $R^1$ is optionally substituted pyridinyl.

In certain embodiments of formula I, $R^1$ is arylalkyl, preferably optionally substituted benzyl or optionally substituted phenylethyl.

In certain embodiments of formula I, $R^1$ is heteroarylalkyl, preferably optionally substituted pyridinylmethyl.

In certain embodiments of formula I, $R^1$ is cycloalkyl, preferably cyclohexyl.

In certain embodiments of formula I, $R^1$ is branched alkyl such as isobutyl or isopropyl.

In certain embodiments of formula I, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, 2-chloro-phenyl, naphthylene-1-yl, naphthylene-2-yl, thien-2-yl, thien-3-yl, pyridin-4-yl, pyridin-3-yl, pyridin-2-yl, pyrimidin-5-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula I, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, 2-chloro-phenyl, naphthylene-1-yl, or naphthylene-2-yl.

In certain embodiments of formula I, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, or 2-chloro-phenyl.

In certain embodiments of formula I, $R^1$ is thien-2-yl, thien-3-yl, pyridin-4-yl, pyridin-3-yl, pyridin-2-yl, pyrimidin-5-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula I, $R^1$ is pyridin-4-yl, pyridin-3-yl, pyridin-2-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula I, Ar is indolyl, indazolyl, 2,3-dihydroindolyl, benzimidazolyl or benzofuranyl, each optionally substituted. In such embodiments Ar is preferably optionally substituted indolyl or optionally substituted indazolyl. Where Ar is optionally substituted indolyl, Ar is more preferably optionally substituted indol-1-yl or optionally substituted indol-3-yl. Where Ar is optionally substituted indazolyl, Ar is more preferably optionally substituted indazol-1-yl or optionally substituted indazol-2-yl.

In many embodiments of formula I, one of $R^2$ and $R^3$ is hydrogen and the other is alkyl, preferably methyl.

In certain embodiments of formula I, p is 2 and $R^a$, $R^b$, $R^c$ and $R^d$ are hydrogen. In such embodiments Ar may be optionally substituted indolyl, $R^1$ may be optionally substituted phenyl, and one of $R^2$ and $R^3$ is hydrogen while the other is alkyl, preferably methyl.

In certain embodiments of formula I, p is 1, $R^a$, $R^b$ and $R^c$ are hydrogen, and $R^d$ is alkyl, preferably methyl. In such embodiments Ar may be optionally substituted indolyl, $R^1$ may be optionally substituted phenyl, and one of $R^2$ and $R^3$ is hydrogen while the other is alkyl, preferably methyl.

In certain embodiments of formula I, p is 1, $R^a$, $R^c$ and $R^d$ are hydrogen, and $R^b$ is alkyl, preferably methyl. In such embodiments Ar may be optionally substituted indolyl, $R^1$ may be optionally substituted phenyl, and one of $R^2$ and $R^3$ is hydrogen while the other is alkyl, preferably methyl.

In certain embodiments of formula I, p is 1, $R^a$, $R^c$ and $R^d$ are hydrogen, and $R^b$ is hydroxy. In such embodiments Ar may be optionally substituted indolyl, $R^1$ may be optionally substituted phenyl, and one of $R^2$ and $R^3$ is hydrogen while the other is alkyl, preferably methyl.

In certain embodiments of formula I, p is 2, $R^a$, $R^c$ and $R^d$ are hydrogen, $R^2$ is hydrogen, and $R^b$ together with $R^3$ and the atoms to which they are attached form a six membered ring.

In such embodiments Ar may be optionally substituted indolyl and $R^1$ may be optionally substituted phenyl.

In certain embodiments of formula I, p is 1, $R^a$, $R^c$ and $R^d$ are hydrogen, $R^2$ is hydrogen, and $R^b$ together with $R^3$ and the atoms to which they are attached form a four membered ring. In such embodiments Ar may be optionally substituted indolyl and $R^1$ may be optionally substituted phenyl.

In certain embodiments of formula I, p is 1, $R^a$, $R^b$ and $R^c$ are hydrogen, $R^2$ is hydrogen, and $R^3$ and $R^d$ together with the atoms to which they are attached form a five membered ring, preferably an imidazolinyl ring. In such embodiments Ar may be optionally substituted indolyl and $R^1$ may be optionally substituted phenyl.

In certain embodiments of formula I, p is 1 and $R^a$, $R^b$, $R^c$ and $R^d$ are hydrogen, and $R^e$ is alkyl, preferably methyl. In such embodiments Ar may be optionally substituted indolyl, $R^1$ may be optionally substituted phenyl, and one of $R^2$ and $R^3$ is hydrogen while the other is alkyl, preferably methyl.

In certain embodiments of formula I: p is 1; $R^a$, $R^b$, $R^c$, $R^d$ and $R^e$ are hydrogen; Ar is indolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—S(O)$_r$$R^f$; —$(CH_2)_q$—NR$^g$R$^h$; —$(CH_2)_q$—C(=O)—NR$^g$R$^h$; —$(CH_2)_q$—C(=O)—C(=O)—NR$^g$R$^h$; —$(CH_2)_q$—SO$_2$—NR$^g$R$^h$; —$(CH_2)_q$—N(R$^f$)—C(=O)—R$^i$; —$(CH_2)_q$—C(=O)—R$^i$; or —$(CH_2)_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy; $R^1$ is phenyl optionally substituted one, two, three or four times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indol-1-yl. Alternatively, in such embodiments Ar may be indol-3-yl.

In certain embodiments of formula I: p is 1; $R^a$, $R^b$, $R^c$, $R^d$ and $R^e$ are hydrogen; Ar is indolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—S(O)$_r$$R^f$; —$(CH_2)_q$—NR$^g$R$^h$; —$(CH_2)_q$—C(=O)—NR$^g$R$^h$; —$(CH_2)_q$—C(=O)—C(=O)—NR$^g$R$^h$; —$(CH_2)_q$—SO$_2$—NR$^g$R$^h$; —$(CH_2)_q$—N(R$^f$)—C(=O)—R$^i$; —$(CH_2)_q$—C(=O)—R$^i$; or —$(CH_2)_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy; $R^1$ is pyridinyl optionally substituted one, two or three times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indol-1-yl. Alternatively, in such embodiments Ar may be indol-3-yl. In such embodiments $R^1$ is preferably pyridin-3-yl.

In certain embodiments of formula I: p is 1; $R^a$, $R^b$, $R^c$, $R^d$ and $R^e$ are hydrogen; Ar is indazolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—S(O)$_r$$R^f$; —$(CH_2)_q$—NR$^g$R$^h$; —$(CH_2)_q$—C(=O)—NR$^g$R$^h$; —$(CH_2)_q$—C(=O)—C(=O)—NR$^g$R$^h$; —$(CH_2)_q$—SO$_2$—NR$^g$R$^h$; —$(CH_2)_q$—N(R$^f$)—C(=O)—R$^i$; —$(CH_2)_q$—C(=O)—R$^i$; or —$(CH_2)_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy; $R^1$ is phenyl optionally substituted one, two, three or four times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indazol-1-yl. Alternatively, in such embodiments Ar may be indazol-2-yl.

In certain embodiments of formula I: p is 1; $R^a$, $R^b$, $R^c$, $R^d$ and $R^e$ are hydrogen; Ar is indazolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—S(O)$_r$$R^f$; —$(CH_2)_q$—NR$^g$R$^h$; —$(CH_2)_q$—C(=O)—NR$^g$R$^h$; —$(CH_2)_q$—C(=O)—C(=O)—NR$^g$R$^h$; —$(CH_2)_q$—SO$_2$—NR$^g$R$^h$; —$(CH_2)_q$—N(R$^f$)—C(=O)—R$^i$; —$(CH_2)_q$—C(=O)—R$^i$; or —$(CH_2)_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy; $R^1$ is pyridinyl optionally substituted one, two or three times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indazol-1-yl. Alternatively, in such embodiments Ar may be indazol-2-yl. In such embodiments $R^1$ is preferably pyridin-3-yl.

In certain embodiments of formula I where p is 1 and $R^a$, $R^b$, $R^c$, $R^d$ and $R^e$ are hydrogen, the subject compounds may be represented by formula II:

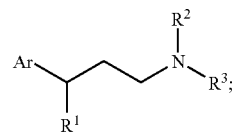

II wherein:
$R^2$ and $R^3$ each independently is hydrogen or alkyl; and
Ar and $R^1$ are as defined herein;
provided that when Ar is indol-1-yl and $R^1$ is phenyl, then $R^2$ and $R^3$ are not simultaneously methyl, and further provided that when Ar is indol-3-yl and $R^1$ is phenyl or 3-methoxyphenyl, then $R^2$ and $R^3$ are not simultaneously hydrogen.

In certain embodiments of formula II, one of $R^2$ and $R^3$ is hydrogen and the other is alkyl, preferably methyl.

In certain embodiments of formula II, $R^1$ is optionally substituted aryl, preferably optionally substituted phenyl or optionally substituted naphthyl.

In certain embodiments of formula II, $R^1$ is optionally substituted heteroaryl. In such embodiments $R^1$ may be pyridinyl, pyrimidinyl, pyridazinyl, pyrazinyl, thienyl, thiazolyl, oxazolyl or quinolinyl, each optionally substituted. Preferably, when $R^1$ is optionally substituted heteroaryl, $R^1$ is pyridinyl, pyrimidinyl, pyrazinyl or pyridazinyl, each optionally substituted. More preferably, $R^1$ may be pyridinyl or pyrimidinyl. Still more preferably, $R^1$ may be optionally substituted pyridinyl, such as optionally substituted pyridin-2-yl, optionally substituted pyridin-3-yl or optionally substituted pyridin-4-yl, and more specifically optionally substituted pyridine-3-yl or optionally substituted pyridine-3-yl.

In certain embodiments of formula II, $R^1$ is optionally substituted phenyl or optionally substituted pyridyl.

In certain embodiments of formula II, $R^1$ is optionally substituted phenyl.

In certain embodiments of formula II, $R^1$ is optionally substituted pyridyl.

In certain embodiments of formula II, $R^1$ is arylalkyl, preferably optionally substituted benzyl or optionally substituted phenylethyl.

In certain embodiments of formula II, $R^1$ is heteroarylalkyl, preferably optionally substituted pyridinylmethyl.

In certain embodiments of formula II, $R^1$ is cycloalkyl, preferably cyclohexyl.

In certain embodiments of formula II, $R^1$ is branched alkyl such as isobutyl, tert-butyl or isopropyl.

In certain embodiments of formula II, $R^1$ is optionally substituted pyridinylmethyl.

In certain embodiments of formula II, $R^1$ is cycloalkylmethyl, preferably cyclohexylmethyl.

In certain embodiments of formula II, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, 2-chloro-phenyl, naphthylene-1-yl, or naphthylene-2-yl.

In certain embodiments of formula II, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, or 2-chloro-phenyl.

In certain embodiments of formula II, $R^1$ is thien-2-yl, thien-3-yl, pyridin-4-yl, pyridin-3-yl, pyridin-2-yl, pyrimidin-5-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula II, $R^1$ is pyridin-4-yl, pyridin-3-yl, pyridin-2-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula II, Ar is indolyl, indazolyl, 2,3-dihydroindolyl, benzimidazolyl or benzofuranyl, each optionally substituted. In such embodiments Ar is preferably optionally substituted indolyl or optionally substituted indazolyl. Where Ar is optionally substituted indolyl, Ar is more preferably optionally substituted indol-1-yl or optionally substituted indol-3-yl. Where Ar is optionally substituted indazolyl, Ar is more preferably optionally substituted indazol-1-yl or optionally substituted indazol-2-yl.

In certain embodiments of formula II, Ar is optionally substituted indolyl or optionally substituted indazolyl. Where Ar is optionally substituted indolyl, Ar is more preferably optionally substituted indol-1-yl or optionally substituted indol-3-yl. Where Ar is optionally substituted indazolyl, Ar is more preferably optionally substituted indazol-1-yl or optionally substituted indazol-2-yl.

In certain embodiments of formula II, Ar is optionally substituted indolyl selected from optionally substituted indol-1-yl, optionally substituted indol-2-yl or optionally substituted indol-3-yl. More preferably, in such embodiments Ar is optionally substituted indol-1-yl or optionally substituted indol-3-yl.

In certain embodiments of formula II, Ar is optionally substituted indazolyl selected from optionally substituted indazol-1-yl, optionally substituted indazol-2-yl or optionally substituted indazol-3-yl. More preferably, in such embodiments Ar is optionally substituted indazol-1-yl or optionally substituted indazol-2-yl.

In certain embodiments of formula II, Ar is optionally substituted 2,3-dihydroindonlyl, preferably 2,3-dihydroindol-1-yl.

In certain embodiments of formula II, Ar is optionally substituted benzimidazolyl, preferably benzimidazol-1-yl.

In certain embodiments of formula II, Ar is optionally substituted benzofuranyl, preferably optionally substituted benzofuran-2-yl.

In certain embodiments of formula II, Ar is optionally substituted benzothiophenyl, preferably optionally substituted benzothiophen-2-yl.

In certain embodiments of formula II, Ar is optionally substituted benzoxazol-2-yl.

In certain embodiments of formula II, Ar is optionally substituted benzothiazol-2-yl.

In certain embodiments of formula II, Ar is: indol-1-yl; indol-2-yl; indol-3-yl; 2,3-dihydroindol-1-yl; indazol-1-yl; indazol-2-yl; or indazol-3-yl; each optionally substituted one, two or three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)-SO_2-R^g$; where q is 0 or 1, r is from 0 to 2, $R^f$, $R^g$ and $R^h$ each independently is hydrogen or alkyl, and each $R^i$ is independently hydrogen, alkyl, hydroxy, or alkoxy.

In certain embodiments of formula II, Ar is: indol-1-yl; indol-2-yl; indol-3-yl; 2,3-dihydroindol-1-yl; indazol-1-yl; indazol-2-yl; or indazol-3-yl; each optionally substituted one, two or three or four times with fluoro, chloro, bromo, methoxy, cyano, ethoxy, isopropoxy, dimethylamino-oxo-acetamide, carboxylic acid methyl ester, carboxylic acid amide, carboxylic acid methyamide, carboxylic acid dimethylamide, acetamide, methanesulfonamido, methanesulfonyl, benzyloxy, trifluoromethyl, 2,2,2-trifluoroethoxy, thien-2-yl, cyclopropylmethoxy, cyclobutylmethoxy, morpholin-4-yl-methanone, pyridin-3-yl and 1-methyl-pyrazol-4-yl.

In certain embodiments of formula II, Ar is: indol-1-yl; indol-2-yl; or indol-3-yl; each optionally substituted one, two or three times with alkyl, alkoxy, halo, haloalkyl, haloalkoxy, cyano, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)-SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy.

In certain embodiments of formula II, Ar is: indol-1-yl; indol-2-yl; or indol-3-yl; each optionally substituted one, two or three times with fluoro, chloro, bromo, methoxy, cyano, ethoxy, isopropoxy, dimethylamino-oxo-acetamide, carboxylic acid methyl ester, carboxylic acid amide, carboxylic acid methyamide, carboxylic acid dimethylamide, acetamide, methanesulfonamido, methanesulfonyl, benzyloxy, trifluoromethyl, 2,2,2-trifluoroethoxy, thien-2-yl, cyclopropylmethoxy, cyclobutylmethoxy, morpholin-4-ylmethanone, pyridin-3-yl or 1-methyl-pyrazol-4-yl.

In certain embodiments of formula II, Ar is: indazol-1-yl; or indazol-2-yl; each optionally substituted one, two or three times with alkyl, alkoxy, halo, haloalkyl, haloalkoxy, cyano, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy.

In certain embodiments of formula II, Ar is: indazol-1-yl; or indazol-2-yl; each optionally substituted one, two or three times with fluoro, chloro, bromo, methoxy, cyano, ethoxy, isopropoxy, dimethylamino-oxo-acetamide, carboxylic acid methyl ester, carboxylic acid amide, carboxylic acid methyamide, carboxylic acid dimethylamide, acetamide, methanesulfonamido, methanesulfonyl, benzyloxy, trifluoromethyl, 2,2,2-trifluoroethoxy, thien-2-yl, cyclopropylmethoxy, cyclobutylmethoxy, morpholin-4-ylmethanone, pyridin-3-yl or 1-methyl-pyrazol-4-yl.

In many embodiments of formula II: Ar is indolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; $R^1$ is phenyl optionally substituted one, two, three or four times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indol-1-yl, which may be substituted once or twice at the 4- and/or 7-position with halo or alkoxy. Alternatively, in such embodiments Ar may be indol-3-yl, which may be substituted once at the 4- or 7-position with halo or alkoxy. A preferred halo in such embodiments is chloro, and a preferred alkoxy in such embodiments is methoxy.

In many embodiments of formula II: Ar is indolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; $R^1$ is pyridinyl optionally substituted one, two or three times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indol-1-yl, which may be substituted once at the 4- or 7-position with halo or alkoxy. Alternatively, in such embodiments Ar may be indol-3-yl, which may be substituted once or twice at the 4- and/or 7-position with halo or alkoxy. A preferred halo in such embodiments is chloro, and a preferred alkoxy in such embodiments is methoxy.

In certain embodiments of formula II: Ar is indazolyl optionally substituted one, two, three or four times with alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; $R^1$ is phenyl optionally substituted one, two, three or four times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indazol-1-yl, which may be substituted once or twice at the 4- and/or 7-position with halo or alkoxy. Alternatively, in such embodiments Ar may be indazol-2-yl, which may be substituted once or twice at the 4- and/or 7-position with halo or alkoxy. A preferred halo in such embodiments is chloro, and a preferred alkoxy in such embodiments is methoxy.

In certain embodiments of formula II: Ar is indazolyl optionally substituted one, two, three or four times with alkyl, alkoxy, halo, haloalkyl, haloalkoxy, cyano, nitro, hydroxyalkyl, heteroalkyl, heteroalkyl, alkoxyalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —$(CH_2)_q$—$S(O)_rR^f$; —$(CH_2)_q$—$NR^gR^h$; —$(CH_2)_q$—$C(=O)$—$NR^gR^h$; —$(CH_2)_q$—$C(=O)$—$C(=O)$—$NR^gR^h$; —$(CH_2)_q$—$SO_2$—$NR^gR^h$; —$(CH_2)_q$—$N(R^f)$—$C(=O)$—$R^i$; —$(CH_2)_q$—$C(=O)$—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; $R^1$ is pyridinyl optionally substituted one, two or three times with alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indazol-1-yl, which may be substituted once or twice at the 4- and/or 7-position with halo or alkoxy. Alternatively, in such embodiments Ar may be indazol-2-yl, which may be substituted once or twice at the 4- and/or 7-position with halo or alkoxy. A preferred halo in such embodiments is chloro, and a preferred alkoxy in such embodiments is methoxy.

In compounds of formula II in which Ar is optionally substituted indolyl, the subject compounds may be represented by formula III:

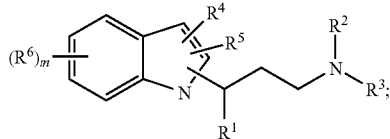

III wherein:
  m is from 0 to 4;
  R⁴ and R⁵ each independently is: hydrogen; alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, morpholinocarbonyl, —(CH₂)_q—S(O)_rR^f; —(CH₂)_q—NR^gR^h; —(CH₂)_q—C(═O)—NR^gR^h; —(CH₂)_q—C(═O)—C(═O)—NR^gR^h; —(CH₂)_q—SO₂—NR^gR^h; —(CH₂)_q—N(R^f)—C(═O)—R^i; —(CH₂)_q—C(═O)—R^i; or —(CH₂)_q—N(R^f)—SO₂—R^g; where q is 0 or 1, r is from 0 to 2, R^f, R^g, and R^h each independently is hydrogen or alkyl, and each R^i is independently hydrogen, alkyl, hydroxy, or alkoxy;
  each R⁶ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —(CH₂)_q—S(O)_rR^f; —(CH₂)_q—NR^gR^h; —(CH₂)_q—C(═O)—NR^gR^h; —(CH₂)_q—C(═O)—C(═O)—NR^gR^h; —(CH₂)_q—SO₂—NR^gR^h; —(CH₂)_q—N(R^f)—C(═O)—R^i; —(CH₂)_q—C(═O)—R^i; or —(CH₂)_q—N(R^f)—SO₂—R^g; where q is 0 or 1, r is from 0 to 2, R^f, R^g, and R^h each independently is hydrogen or alkyl, and each R^i is independently hydrogen, alkyl, hydroxy, or alkoxy; and
  R¹, R² and R³ are as defined herein.

In embodiments of formula II wherein Ar is optionally substituted indol-1-yl, the compounds of the invention may be more specifically of formula IV:

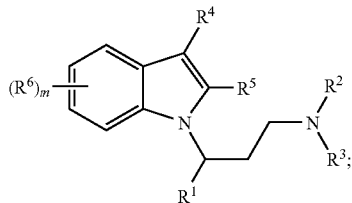

IV wherein m, R¹, R², R³, R⁴, R⁵ and R⁶ are as defined herein.
In certain embodiments of formula IV, the subject compounds may be more specifically of formula IVa or IVb:

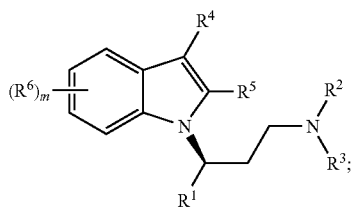

IVa

-continued

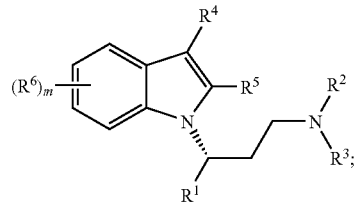

IVb wherein m, R¹, R², R³, R⁴, R⁵ and R⁶ are as defined herein. Preferably such compounds are of formula IVa.

In embodiments of formula II wherein Ar is optionally substituted indol-2-yl, the compounds of the invention may be more specifically of formula V:

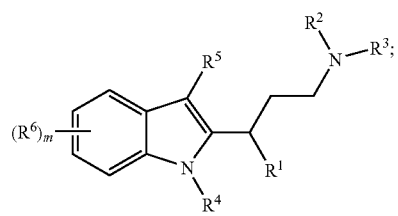

V wherein m, R¹, R², R³, R⁴, R⁵ and R⁶ are as defined herein. In embodiments of formula V, R⁴ is preferably hydrogen.

In embodiments of formula II wherein Ar is optionally substituted indol-3-yl, the compounds of the invention may be more specifically of formula V:

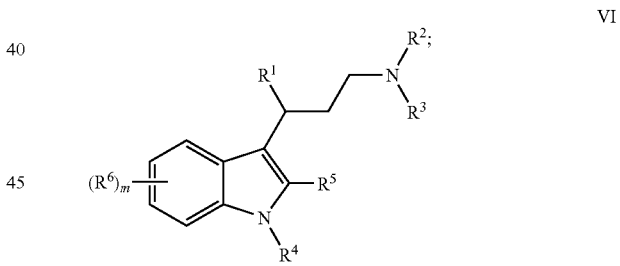

VI wherein m, R¹, R², R³, R⁴, R⁵ and R⁶ are as defined herein. In embodiments of formula VI, R⁴ is preferably hydrogen.

In certain embodiments of formula VI, the subject compounds may be more specifically of formula VIa or VIb:

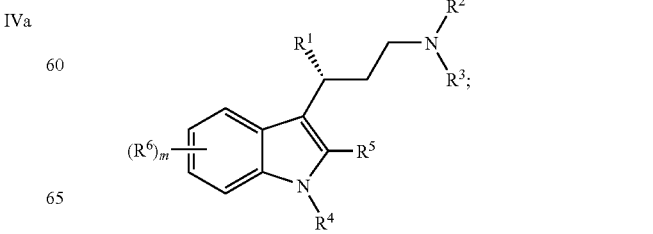

VIa

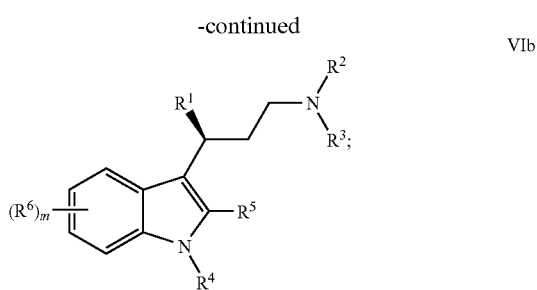

VIb wherein m, $R^1$, $R^2$, $R^3$, $R^4$, $R^5$ and $R^6$ are as defined herein. Preferably such compounds are of formula VIa. In embodiments of formula VIa and VIb, $R^4$ is preferably hydrogen.

In certain embodiments of any of formulas III, IV, IVa, IVb, V, VI, VIa or VIb, one of $R^2$ and $R^3$ is hydrogen and the other is alkyl, preferably methyl.

In certain embodiments of any of formulas III, IV, IVa, IVb, V, VI, VIa or VIb, $R^1$ is optionally substituted aryl, preferably optionally substituted phenyl.

In certain embodiments of any of formulas III, IV, IVa, IVb, V, VI, VIa or VIb, $R^1$ is optionally substituted heteroaryl. In such embodiments $R^1$ may be pyridinyl, pyrimidinyl, pyridazinyl, pyrazinyl, thienyl or quinolinyl, each optionally substituted. Preferably, when $R^1$ is optionally substituted heteroaryl, $R^1$ is pyridinyl, pyrimidinyl, pyrazinyl or pyridazinyl, each optionally substituted. More preferably, $R^1$ may be pyridinyl or pyrimidinyl. Still more preferably, $R^1$ may be optionally substituted pyridinyl, such as optionally substituted pyridin-2-yl, optionally substituted pyridin-3-yl or optionally substituted pyridin-4-yl, and more specifically optionally substituted pyridin-2-yl or optionally substituted pyridine-3-yl.

In certain embodiments of any of formulas III, IV, IVa, IVb, V, VI, VIa or VIb, $R^1$ is optionally substituted phenyl or optionally substituted pyridyl.

In certain embodiments of any of formulas III, IV, IVa, IVb, V, VI, VIa or VIb, $R^1$ is optionally substituted phenyl.

In certain embodiments of any of formulas III, IV, IVa, IVb, V, VI, VIa or VIb, $R^1$ is optionally substituted pyridyl.

In certain embodiments of any of formulas III, IV, IVa, IVb, V, VI, VIa or VIb, $R^1$ is arylalkyl, preferably optionally substituted benzyl or optionally substituted phenylethyl.

In certain embodiments of any of formulas III, IV, IVa, IVb, V, VI, VIa or VIb, $R^1$ is heteroarylalkyl, preferably optionally substituted pyridinylmethyl.

In certain embodiments of any of formulas III, IV, IVa, IVb, V, VI, VIa or VIb, $R^1$ is cycloalkyl, preferably cyclohexyl.

In certain embodiments of any of formulas III, IV, IVa, IVb, V, VI, VIa or VIb, $R^1$ is branched alkyl such as isobutyl, tert-butyl or isopropyl.

In certain embodiments of any of formulas III, IV, IVa, IVb, V, VI, VIa or VIb, $R^1$ is optionally substituted pyridinylmethyl.

In certain embodiments of any of formulas III, IV, IVa, IVb, V, VI, VIa or VIb, $R^1$ is cycloalkylmethyl, preferably cyclohexylmethyl.

In certain embodiments of formula III, IV, IVa, IVb, V, VI, VIa or VIb, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, 2-chloro-phenyl, naphthylene-1-yl, or naphthylene-2-yl.

In certain embodiments of formula III, IV, IVa, IVb, V, VI, VIa or VIb, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chloro-phenyl, 3-chloro-phenyl, or 2-chloro-phenyl.

In certain embodiments of formula III, IV, IVa, IVb, V, VI, VIa or VIb, $R^1$ is thien-2-yl, thien-3-yl, pyridin-4-yl, pyridin-3-yl, pyridin-2-yl, pyrimidin-5-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula III, IV, IVa, IVb, V, VI, VIa or VIb, $R^1$ is pyridin-4-yl, pyridin-3-yl, pyridin-2-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of any of formulas III, IV, IVa, IVb, V, VI, VIa or VIb, each $R^6$ is independently fluoro, chloro, bromo, methoxy, difluoromethoxy, cyano, ethoxy, isopropoxy, dimethylamino-oxo-acetamide, carboxylic acid methyl ester, carboxylic acid amide, carboxylic acid methyamide, carboxylic acid dimethylamide, acetamide, methanesulfonamido, methanesulfonyl, benzyloxy, trifluoromethyl, 2,2,2-trifluoroethoxy, thien-2-yl, cyclopropylmethoxy, cyclobutylmethoxy, morpholin-4-ylmethanone, pyridin-3-yl and 1-methyl-pyrazol-4-yl.

In certain embodiments of any of formulas III, IV, IVa, IVb, V, VI, VIa or VIb, m is 0, 1 or 2 and each $R^6$ is independently chloro, methoxy, isopropoxy, cyano or cyclopropylmethoxy.

In certain embodiments of any of formulas III, IV, IVa, IVb, V, VI, VIa or VIb, m is 0, 1 or 2 and each $R^6$ is independently halo, alkyl, alkoxy or cyano.

In certain embodiments of any of formulas III, IV, IVa, IVb, V, VI, VIa or VIb, m is 0.

In certain embodiments of any of formulas III, IV, IVa, IVb, V, VI, VIa or VIb, m is 1, and $R^6$ is located at the 4- or 7 position of the indole ring system.

In certain embodiments of any of formulas III, IV, IVa, IVb, V, VI, VIa or VIb, m is 1, and $R^6$ is halo, cyano or alkoxy at the 4- or 7 position of the indole ring system.

In certain embodiments of any of formulas III, IV, IVa, IVb, V, VI, VIa or VIb, m is 2, and $R^6$ is located at the 4- and 7 positions of the indole ring system.

In certain embodiments of any of formulas III, IV, IVa, IVb, V, VI, VIa or VIb, m is 2, and each $R^6$ is independently halo, cyano or alkoxy located at the 4- and 7 positions of the indole ring system.

In certain embodiments of formulas III, IV, IVa, IVb, V, VI, VIa or VIb, $R^4$ and $R^5$ are hydrogen.

In certain embodiments of any of formulas III, IV, IVa, IVb, V, VI, VIa or VIb, one of $R^4$ and $R^5$ is hydrogen and the other is alkyl, cyano, halo or alkoxy.

In certain embodiments of any of formulas III, IV, IVa, IVb, V, VI, VIa or VIb, m is 0, 1 or 2, $R^1$ is optionally substituted phenyl, and one of $R^2$ and $R^3$ is hydrogen and the other is alkyl, preferably methyl. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas III, IV, IVa, IVb, V, VI, VIa or VIb, m is 0, 1 or 2, $R^1$ is optionally substituted phenyl, one of $R^2$ and $R^3$ is hydrogen and the other is alkyl, preferably methyl, and $R^4$ and $R^5$ are hydrogen. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas III, IV, IVa, IVb, V, VI, VIa or VIb, m is 0, 1 or 2, $R^1$ is optionally substituted phenyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl. In specific embodiments m is 1 and $R^6$ is halo, cyano or alkoxy at the 4- or 7-position of the indole ring system. A preferred halo in such embodiments is chloro, and a preferred alkoxy in such embodiments is methoxy.

In certain embodiments of any of formulas III, IV, IVa, IVb, V, VI, VIa or VIb, m is 0, 1 or 2, $R^1$ is optionally substituted pyridinyl, and one of $R^2$ and $R^3$ is hydrogen and the other is alkyl, preferably methyl. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of formulas any of III, IV, IVa, IVb, V, VI, VIa or VIb, m is 0, 1 or 2, $R^1$ is optionally substituted pyridinyl, one of $R^2$ and $R^3$ is hydrogen and the other is alkyl, preferably methyl, and $R^4$ and $R^5$ are hydrogen. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas III, IV, IVa, IVb, V, VI, VIa or VIb, m is 0, 1 or 2, $R^1$ is optionally substituted pyridinyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In specific embodiments m is 1 and $R^6$ is halo, cyano or alkoxy at the 4- or 7-position of the indole ring system. A preferred halo in such embodiments is chloro, and a preferred alkoxy in such embodiments is methoxy. In such embodiments $R^1$ is preferably pyridin-3-yl or pyridin-2-yl.

In certain embodiments of formula VI, m is 1, $R^1$ is optionally substituted phenyl, one of $R^2$ and $R^3$ is hydrogen and the other is alkyl, preferably methyl, $R^4$ and $R^5$ are hydrogen, and $R^6$ is halo, cyano or alkoxy at the 7-position of the indole ring system. A preferred halo in such embodiments is chloro, and a preferred alkoxy in such embodiments is methoxy.

In certain embodiments of formula VIa, m is 1, $R^1$ is optionally substituted phenyl, one of $R^2$ and $R^3$ is hydrogen and the other is alkyl, preferably methyl, $R^4$ and $R^5$ are hydrogen, and $R^6$ is halo or alkoxy at the 7-position of the indole ring system. A preferred halo in such embodiments is chloro, and a preferred alkoxy in such embodiments is methoxy.

In certain embodiments of formula VI, m is 2, $R^1$ is optionally substituted phenyl, one of $R^2$ and $R^3$ is hydrogen and the other is alkyl, preferably methyl, $R^4$ and $R^5$ are hydrogen, and each $R^6$ is independently halo, cyano or alkoxy located at the 4- and 7-positions of the indole ring system. A preferred halo in such embodiments is chloro, and a preferred alkoxy in such embodiments is methoxy.

In certain embodiments of formula VIa, m is 1, $R^1$ is optionally substituted phenyl, one of $R^2$ and $R^3$ is hydrogen and the other is alkyl, preferably methyl, $R^4$ and $R^5$ are hydrogen, and $R^6$ is halo, cyano or alkoxy located at the 4- or 7-position of the indole ring system. A preferred halo in such embodiments is chloro, and a preferred alkoxy in such embodiments is methoxy.

In certain embodiments of formula VI, m is 1, $R^1$ is optionally substituted pyridinyl, one of $R^2$ and $R^3$ is hydrogen and the other is alkyl, preferably methyl, $R^4$ and $R^5$ are hydrogen, and $R^6$ is halo, cyano or alkoxy at the 7-position of the indole ring system. A preferred halo in such embodiments is chloro, and a preferred alkoxy in such embodiments is methoxy. In such embodiments $R^1$ is preferably optionally substituted pyridin-3-yl or pyridin-2-yl.

In certain embodiments of formula VIa, m is 1, $R^1$ is optionally substituted pyridinyl, one of $R^2$ and $R^3$ is hydrogen and the other is alkyl, preferably methyl, $R^4$ and $R^5$ are hydrogen, and $R^6$ is halo or alkoxy at the 7-position of the indole ring system. A preferred halo in such embodiments is chloro, and a preferred alkoxy in such embodiments is methoxy. In such embodiments $R^1$ is preferably optionally substituted pyridin-3-yl or pyridin-2-yl.

In certain embodiments of formula VI, m is 2, $R^1$ is optionally substituted pyridinyl, one of $R^2$ and $R^3$ is hydrogen and the other is alkyl, preferably methyl, $R^4$ and $R^5$ are hydrogen, and each $R^6$ is independently halo, cyano or alkoxy located at the 4- and 7-positions of the indole ring system. A preferred halo in such embodiments is chloro, and a preferred alkoxy in such embodiments is methoxy. In such embodiments $R^1$ is preferably optionally substituted pyridin-3-yl or pyridin-2-yl.

In certain embodiments of formula VIa, m is 1, $R^1$ is optionally substituted pyridinyl, one of $R^2$ and $R^3$ is hydrogen and the other is alkyl, preferably methyl, $R^4$ and $R^5$ are hydrogen, and $R^6$ is halo, cyano or alkoxy located at the 4- or 7-position of the indole ring system. A preferred halo in such embodiments is chloro, and a preferred alkoxy in such embodiments is methoxy. In such embodiments $R^1$ is preferably optionally substituted pyridin-3-yl or pyridin-2-yl.

In embodiments of the invention wherein Ar is optionally substituted indolyl, $R^1$ is optionally substituted phenyl and $R^3$ is hydrogen, the subject compounds may be represented by formula VII:

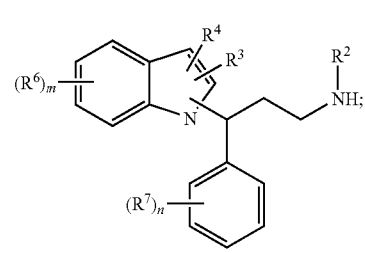

VII wherein:
n is from 0 to 4;
$R^2$ is alkyl, preferably methyl;
each $R^7$ independently is alkyl, alkoxy, cyano, halo, haloalkyl, haloalkoxy, alkoxyalkyl or hydroxyalkyl, or two of $R^7$ may form an alkylene dioxy; and
m, $R^4$, $R^5$, and $R^6$ are as defined herein.

In certain embodiments of formula VII, the compounds of the invention may more specifically be represented by formula VIII:

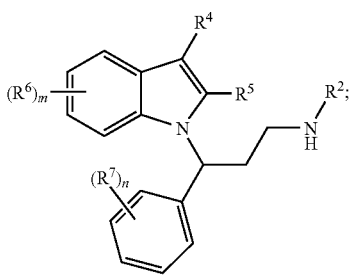

VIII wherein m, n, $R^1$, $R^2$, $R^4$, $R^5$, $R^6$ and $R^7$ are as defined herein.

In certain embodiments of formula VIII, the compounds of the invention may more specifically be represented by formula VIIIa or formula VIIIb:

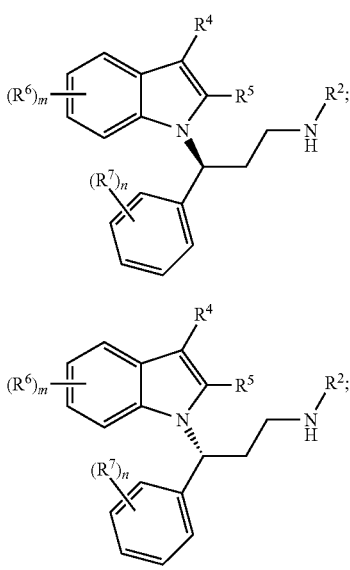

VIIIa

VIIIb wherein m, n, $R^1$, $R^2$, $R^4$, $R^5$, $R^6$ and $R^7$ are as defined herein. Preferably such compounds are of formula VIIIa.

In certain embodiments of formula VII, the compounds of the invention may more specifically be represented by formula IX:

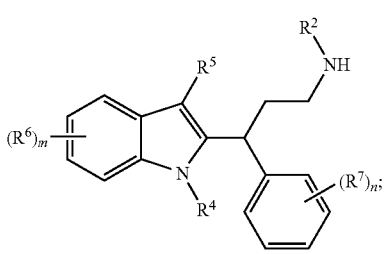

IX wherein m, n, $R^1$, $R^2$, $R^4$, $R^5$, $R^6$ and $R^7$ are as defined herein. In embodiments of formula IX, $R^4$ is preferably hydrogen.

In certain embodiments of formula VII, the compounds of the invention may more specifically be represented by formula X:

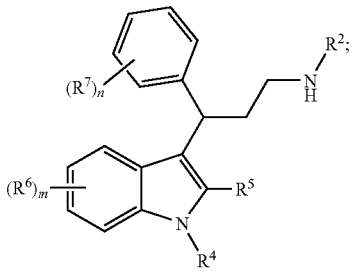

X wherein m, n, $R^1$, $R^2$, $R^4$, $R^5$, $R^6$ and $R^7$ are as defined herein. In embodiments of formula X, $R^4$ is preferably hydrogen.

In certain embodiments of formula X, the compounds of the invention may more specifically be represented by formula Xa or formula Xb:

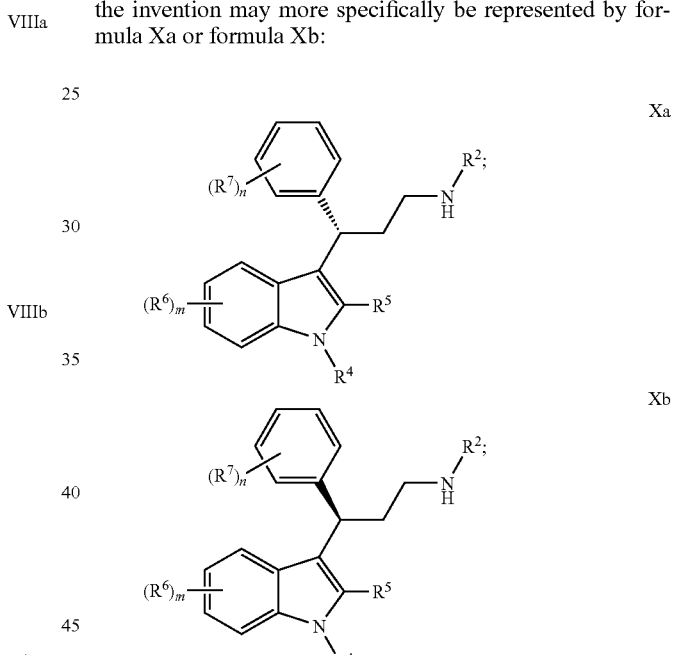

Xa

Xb wherein m, n, $R^1$, $R^2$, $R^4$, $R^5$, $R^6$ and $R^7$ are as defined herein. Preferably, in such embodiments the compounds are of formula Xa. In embodiments of formula Xa and Xb, $R^4$ is preferably hydrogen.

In certain embodiments of any of formulas VII, VIII, VIIIa, VIIIb, IX, X, Xa or Xb, $R^4$, $R^5$ and $R^6$ each independently is fluoro, chloro, bromo, methoxy, difluoromethoxy, cyano, ethoxy, isopropoxy, dimethylamino-oxo-acetamide, carboxylic acid methyl ester, carboxylic acid amide, carboxylic acid methyamide, carboxylic acid dimethylamide, acetamide, methanesulfonamido, methanesulfonyl, benzyloxy, trifluoromethyl, 2,2,2-trifluoroethoxy, thien-2-yl, cyclopropylmethoxy, cyclobutylmethoxy, morpholin-4-ylmethanone, pyridin-3-yl and 1-methyl-pyrazol-4-yl.

In certain embodiments of any of formulas VII, VIII, VIIIa, VIIIb, IX, X, Xa or Xb, m is 0, 1 or 2 and each $R^6$ is independently chloro, methoxy, isopropoxy, cyano or cyclopropylmethoxy.

In certain embodiments of any of formulas VII, VIII, VIIIa, VIIIb, IX, X, Xa or Xb, m is 0, 1 or 2 and each $R^6$ independently is halo, alkyl, alkoxy or cyano.

In certain embodiments of any of formulas VII, VIII, VIIIa, VIIIb, IX, X, Xa or Xb, m is 1, and $R^6$ is halo or alkoxy at the 4- or 7-position of the indole ring system.

In certain embodiments of any of formulas VII, VIII, VIIIa, VIIIb, IX, X, Xa or Xb, $R^4$ and $R^5$ are hydrogen.

In certain embodiments of any of formulas VII, VIII, VIIIa, VIIIb, IX, X, Xa or Xb, one of $R^4$ and $R^5$ is hydrogen and the other is alkyl, cyano, halo or alkoxy.

In certain embodiments of any of formulas VII, VIII, VIIIa, VIIIb, IX, X, Xa or Xb, $R^2$ is methyl.

In certain embodiments of any of formulas VII, VIII, VIIIa, VIIIb, IX, X, Xa or Xb, $R^2$ is methyl and $R^4$ and $R^5$ are hydrogen.

In certain embodiments of any of formulas VII, VIII, VIIIa, VIIIb, IX, X, Xa or Xb, $R^2$ is methyl, $R^4$ and $R^5$ are hydrogen, m is 0, 1 or 2 and n is 0, 1 or 2.

In certain embodiments of any of formulas VII, VIII, VIIIa, VIIIb, IX, X, Xa or Xb, $R^2$ is methyl, $R^4$ and $R^5$ are hydrogen, m is 0, 1 or 2, n is 0 or 2, and $R^6$ is halo or alkoxy.

In certain embodiments of any of formulas VII, VIII, VIIIa, VIIIb, IX, X, Xa or Xb, $R^2$ is methyl, $R^4$ and $R^5$ are hydrogen, m is 0, 1 or 2, n is 0, 1 or 2, and $R^6$ is halo, cyano or alkoxy located at the 4- or 7-position of the indole ring system. A preferred halo in such embodiments is chloro, and a preferred alkoxy in such embodiments is methoxy.

In certain embodiments of any of formulas VII, VIII, VIIIa, VIIIb, IX, X, Xa or Xb, $R^2$ is methyl, $R^4$ is hydrogen, m is 1, n is 0, 1 or 2, and $R^6$ is chloro or methoxy located at the 4- or 7-position of the indole ring system.

In certain embodiments of any of formulas X, Xa or Xb, $R^2$ is methyl, $R^4$ is hydrogen, m is 1, n is 0, 1 or 2, and $R^6$ is halo, cyano or alkoxy located at the 4-position of the indole ring system. A preferred halo in such embodiments is chloro, and a preferred alkoxy in such embodiments is methoxy.

In certain embodiments of any of formulas X, Xa or Xb, $R^2$ is methyl, $R^4$ is hydrogen, m is 2, n is 0, 1 or 2, and each $R^6$ independently is halo, cyano or alkoxy located at the 4- and 7-positions of the indole ring system. A preferred halo in such embodiments is chloro, and a preferred alkoxy in such embodiments is methoxy.

In compounds of formula II in which Ar is optionally substituted indazolyl, the subject compounds may be represented by formula XI:

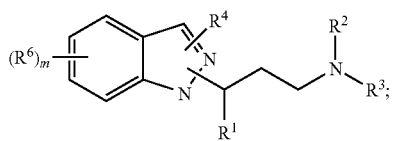

XI wherein:
m is from 0 to 4;
$R^4$ is: hydrogen; alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, morpholinocarbonyl, —$(CH_2)_q$—S(O)$_r R^f$; —$(CH_2)_q$—$NR^g R^h$; —$(CH_2)_q$—C(=O)—$NR^g R^h$; —$(CH_2)_q$—C(=O)—C(=O)—$NR^g R^h$; —$(CH_2)_q$—$SO_2$—$NR^g R^h$; —$(CH_2)_q$—N($R^f$)—C(=O)—$R^i$; —$(CH_2)_q$—C(=O)—$R^i$; or —$(CH_2)_q$—N($R^f$)—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy;

each $R^6$ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—S(O)$_r R^f$; —$(CH_2)_q$—$NR^g R^h$; —$(CH_2)_q$—C(=O)—$NR^g R^h$; —$(CH_2)_q$—C(=O)—C(=O)—$NR^g R^h$; —$(CH_2)_q$—$SO_2$—$NR^g R^h$; —$(CH_2)_q$—N($R^f$)—C(=O)—$R^i$; —$(CH_2)_q$—C(=O)—$R^i$; or —$(CH_2)_q$—N($R^f$)—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; and $R^1$, $R^2$ and $R^3$ are as defined herein.

In embodiments of formula II wherein Ar is optionally substituted indazol-3-yl, the compounds of the invention may be more specifically of formula XII:

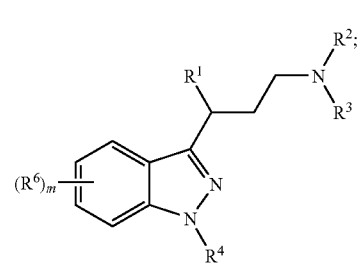

XII wherein m, $R^1$, $R^2$, $R^3$, $R^4$ and $R^6$ are as defined herein. In embodiments of formula XII, $R^4$ is preferably hydrogen.

In embodiments of formula II wherein Ar is optionally substituted indazol-2-yl, the compounds of the invention may be more specifically of formula XIII:

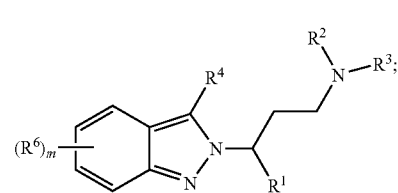

XIII wherein m, $R^1$, $R^2$, $R^3$, $R^4$ and $R^6$ are as defined herein.

In embodiments of formula II wherein Ar is optionally substituted indazol-1-yl, the compounds of the invention may be more specifically of formula XIV:

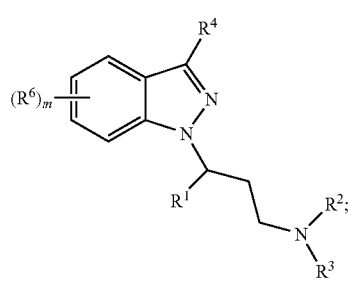

XIV wherein m, $R^1$, $R^2$, $R^3$, $R^4$ and $R^6$ are as defined herein.

In certain embodiments of formula XIV, the compounds of the invention may more specifically be represented by formula XIVa or formula XIVb:

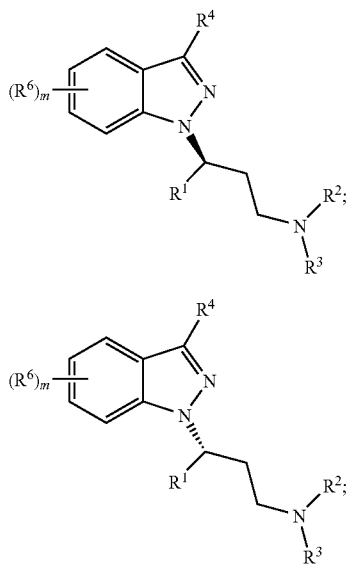

XIVa

XIVb wherein m, $R^1$, $R^2$, $R^3$, $R^4$ and $R^6$ are as defined herein. Preferably such compounds are of formula XIVa.

In certain embodiments of any of formulas XI, XII, XIII, XIV, XIVa or XIVb, one of $R^2$ and $R^3$ is hydrogen and the other is alkyl, preferably methyl.

In certain embodiments of any of formulas XI, XII, XIII, XIV, XIVa or XIVb, $R^1$ is optionally substituted aryl, preferably optionally substituted phenyl.

In certain embodiments of any of formulas XI, XII, XIII, XIV, XIVa or XIVb, $R^1$ is optionally substituted heteroaryl. In such embodiments $R^1$ may be pyridinyl, pyrimidinyl, pyridazinyl, pyrazinyl, thienyl or quinolinyl, each optionally substituted. Preferably, when $R^1$ is optionally substituted heteroaryl, $R^1$ is pyridinyl, pyrimidinyl, pyrazinyl or pyridazinyl, each optionally substituted. More preferably, $R^1$ may be pyridinyl or pyrimidinyl. Still more preferably, $R^1$ may be optionally substituted pyridinyl, such as optionally substituted pyridin-2-yl, optionally substituted pyridin-3-yl or optionally substituted pyridin-4-yl, and more specifically optionally substituted pyridin-2-yl or optionally substituted pyridine-3-yl.

In certain embodiments of any of formulas XI, XII, XIII, XIV, XIVa or XIVb, $R^1$ is optionally substituted phenyl or optionally substituted pyridyl.

In certain embodiments of any of formulas XI, XII, XIII, XIV, XIVa or XIVb, $R^1$ is optionally substituted phenyl In certain embodiments of any of formulas XI, XII, XIII, XIV, XIVa or XIVb, $R^1$ is optionally substituted pyridyl.

In certain embodiments of any of formulas XI, XII, XIII, XIV, XIVa or XIVb, $R^1$ is arylalkyl, preferably optionally substituted benzyl or optionally substituted phenylethyl.

In certain embodiments of any of formulas XI, XII, XIII, XIV, XIVa or XIVb, $R^1$ is heteroarylalkyl, preferably optionally substituted pyridinylmethyl.

In certain embodiments of any of formulas XI, XII, XIII, XIV, XIVa or XIVb, $R^1$ is cycloalkyl, preferably cyclohexyl.

In certain embodiments of any of formulas XI, XII, XIII, XIV, XIVa or XIVb, $R^1$ is branched alkyl such as isobutyl, tert-butyl or isopropyl.

In certain embodiments of formulas XI, XII, XIII, XIV, XIVa or XIVb, $R^1$ is optionally substituted pyridinylmethyl.

In certain embodiments of formulas XI, XII, XIII, XIV, XIVa or XIVb, $R^1$ is cycloalkylmethyl, preferably cyclohexylmethyl.

In certain embodiments of formula XI, XII, XIII, XIV, XIVa or XIVb, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chlorophenyl, 3-chloro-phenyl, 2-chloro-phenyl, naphthylene-1-yl, or naphthylene-2-yl.

In certain embodiments of formula XI, XII, XIII, XIV, XIVa or XIVb, $R^1$ is phenyl, 3,4-methylenedioxy-phenyl, 4-methoxy-phenyl, 3-methoxy-phenyl, 2-methoxy-phenyl, 4-fluoro-phenyl, 3-fluoro-phenyl, 2-fluoro-phenyl, 4-chlorophenyl, 3-chloro-phenyl, or 2-chloro-phenyl.

In certain embodiments of formula XI, XII, XIII, XIV, XIVa or XIVb, $R^1$ is thien-2-yl, thien-3-yl, pyridin-4-yl, pyridin-3-yl, pyridin-2-yl, pyrimidin-5-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of formula XI, XII, XIII, XIV, XIVa or XIVb, $R^1$ is pyridin-4-yl, pyridin-3-yl, pyridin-2-yl, 2-methoxy-pyridin-3-yl, quinolin-2-yl, 2-chloro-pyridin-3-yl, 6-fluoro-2-methyl-pyridin-3-yl, 2-chloro-5-fluoro-pyridin-3-yl, 5-chloro-4-methoxy-pyridin-3-yl, or 4-methoxy-pyridin-3-yl.

In certain embodiments of any of formulas XI, XII, XIII, XIV, XIVa or XIVb, each $R^6$ is independently is fluoro, chloro, bromo, methoxy, difluoromethoxy, cyano, ethoxy, isopropoxy, dimethylamino-oxo-acetamide, carboxylic acid methyl ester, carboxylic acid amide, carboxylic acid methyamide, carboxylic acid dimethylamide, acetamide, methanesulfonamido, methanesulfonyl, benzyloxy, trifluoromethyl, 2,2,2-trifluoroethoxy, thien-2-yl, cyclopropylmethoxy, cyclobutylmethoxy, morpholin-4-ylmethanone, pyridin-3-yl and 1-methyl-pyrazol-4-yl.

In certain embodiments of any of formulas XI, XII, XIII, XIV, XIVa or XIVb, m is 0, 1 or 2 and each $R^6$ independently is halo, alkyl, alkoxy or cyano.

In certain embodiments of any of formulas XI, XII, XIII, XIV, XIVa or XIVb, m is 0.

In certain embodiments of any of formulas XI, XII, XIII, XIV, XIVa or XIVb, m is 1, and $R^6$ is located at the 4- or 7 position of the indazole ring system.

In certain embodiments of any of formulas XI, XII, XIII, XIV, XIVa or XIVb, m is 1, and $R^6$ is halo, cyano or alkoxy located at the 4- or 7 position of the indazole ring system.

In certain embodiments of any of formulas XI, XII, XIII, XIV, XIVa or XIVb, m is 2, and $R^6$ is located at the 4- and 7 positions of the indazole ring system.

In certain embodiments of any of formulas XI, XII, XIII, XIV, XIVa or XIVb, m is 2, and each $R^6$ is independently halo, cyano or alkoxy located at the 4- and 7 positions of the indazole ring system.

In certain embodiments of any of formulas XI, XII, XIII, XIV, XIVa or XIVb, $R^4$ is hydrogen.

In certain embodiments of any of formulas XI, XII, XIII, XIV, XIVa or XIVb, $R^4$ is alkyl, cyano, halo or alkoxy.

In certain embodiments of any of formulas XI, XII, XIII, XIV, XIVa or XIVb, m is 0, 1 or 2, $R^1$ is optionally substituted phenyl, and one of $R^2$ and $R^3$ is hydrogen and the other is alkyl, preferably methyl. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas XI, XII, XIII, XIV, XIVa or XIVb, m is 0, 1 or 2, $R^1$ is optionally substituted phenyl, one of $R^2$ and $R^3$ is hydrogen and the other is alkyl, preferably methyl, and $R^4$ is hydrogen. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas XI, XII, XIII, XIV, XIVa or XIVb, m is 0, 1 or 2, $R^1$ is optionally substituted phenyl, one of $R^2$ and $R^3$ is hydrogen and the other is alkyl, preferably methyl, $R^4$ is hydrogen, and each $R^6$ is independently halo, cyano or alkoxy. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl. In specific embodiments m is 1 and $R^6$ is halo or alkoxy at the 4- or 7-position of the indazole ring system. A preferred halo in such embodiments is chloro, and a preferred alkoxy in such embodiments is methoxy.

In certain embodiments of any of formulas XI, XII, XIII, XIV, XIVa or XIVb, m is 0, 1 or 2, $R^1$ is optionally substituted pyridinyl, and one of $R^2$ and $R^3$ is hydrogen and the other is alkyl, preferably methyl. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably optionally substituted pyridin-3-yl or pyridin-2-yl.

In certain embodiments of any of formulas XI, XII, XIII, XIV, XIVa or XIVb, m is 0, 1 or 2, $R^1$ is optionally substituted pyridinyl, one of $R^2$ and $R^3$ is hydrogen and the other is alkyl, preferably methyl, and $R^4$ is hydrogen. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably optionally substituted pyridin-3-yl or pyridin-2-yl.

In certain embodiments of any of formulas XI, XII, XIII, XIV, XIVa or XIVb, m is 0, 1 or 2, $R^1$ is optionally substituted pyridinyl, one of $R^2$ and $R^3$ is hydrogen and the other is alkyl, preferably methyl, $R^4$ is hydrogen, and each $R^6$ is independently halo, cyano or alkoxy. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In specific embodiments m is 1 and $R^6$ is halo or alkoxy at the 4- or 7-position of the indazole ring system. A preferred halo in such embodiments is chloro, and a preferred alkoxy in such embodiments is methoxy. In such embodiments $R^1$ is preferably optionally substituted pyridin-3-yl or pyridin-2-yl.

In embodiments of the invention wherein Ar is optionally substituted indazolyl, $R^1$ is optionally substituted phenyl and $R^3$ is hydrogen, the subject compounds may be represented by formula XV:

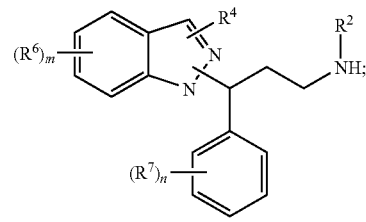

XV wherein:
n is from 0 to 4;
each $R^7$ independently is alkyl, alkoxy, cyano, halo, haloalkyl, haloalkoxy, alkoxyalkyl or hydroxyalkyl, or two of $R^7$ may form an alkylene dioxy; and
m, $R^2$, $R^4$ and $R^6$ are as defined herein.

In certain embodiments of formula XV, the compounds of the invention may more specifically be represented by formula XVI:

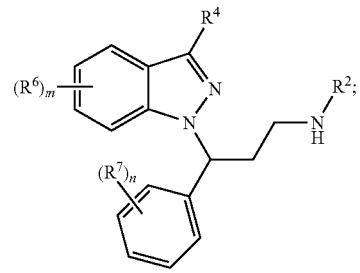

XVI wherein m, n, $R^1$, $R^2$, $R^4$, $R^6$ and $R^7$ are as defined herein.

In certain embodiments of formula XVI, the compounds of the invention may more specifically be represented by formula XIVa or formula XIVb:

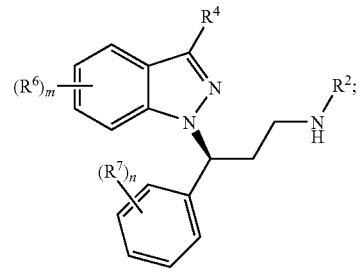

XVIa

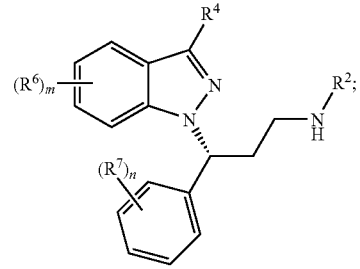

XVIb wherein m, n, $R^1$, $R^2$, $R^4$, $R^6$ and $R^7$ are as defined herein. Preferably such compounds are of formula XVIa.

In certain embodiments of formula VII, the compounds of the invention may more specifically be represented by formula XVII:

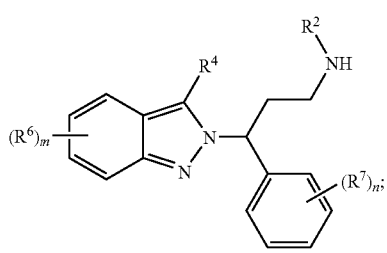

XVII wherein m, n, $R^1$, $R^2$, $R^4$, $R^6$ and $R^7$ are as defined herein.

In certain embodiments of formula VII, the compounds of the invention may more specifically be represented by formula XVIII:

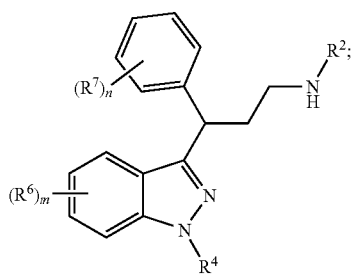

XVIII wherein m, n, $R^1$, $R^2$, $R^4$, $R^6$ and $R^7$ are as defined herein. In embodiments of formula XVIII, $R^4$ is preferably hydrogen.

In certain embodiments of any of formulas XV, XVI, XVIa, XVIb, XVII or XVIII, m is 0, 1 or 2 and each $R^6$ is independently halo, alkyl, alkoxy or cyano.

In certain embodiments of any of formulas XV, XVI, XVIa, XVIb, XVII or XVIII, m is 1, and $R^6$ is halo, cyano or alkoxy at the 4- or 7 position of the indazole ring system.

In certain embodiments of any of formulas XV, XVI, XVIa, XVIb, XVII or XVIII, $R^4$ is hydrogen.

In certain embodiments of any of formulas XV, XVI, XVIa, XVIb, XVII or XVIII, $R^4$ is alkyl, cyano, halo or alkoxy.

In certain embodiments of any of formulas XV, XVI, XVIa, XVIb, XVII or XVIII, $R^2$ is methyl.

In certain embodiments of any of formulas XV, XVI, XVIa, XVIb, XVII or XVIII, $R^2$ is methyl and $R^4$ is hydrogen.

In certain embodiments of any of formulas XV, XVI, XVIa, XVIb, XVII or XVIII, $R^2$ is methyl, $R^4$ is hydrogen, m is 0, 1 or 2 and n is 0, 1 or 2.

In certain embodiments of any of formulas XV, XVI, XVIa, XVIb, XVII or XVIII, $R^2$ is methyl, $R^4$ is hydrogen, m is 0, 1 or 2, n is 0 or 2, and $R^6$ is halo or alkoxy.

In certain embodiments of any of formulas XV, XVI, XVIa, XVIb, XVII or XVIII, $R^2$ is methyl, $R^4$ is hydrogen, m is 0, 1 or 2, n is 0, 1 or 2, and each $R^6$ is independently halo or alkoxy located at the 4- or 7-position of the indazole ring system.

In certain embodiments of any of formulas XV, XVI, XVIa, XVIb, XVII or XVIII, $R^2$ is methyl, $R^4$ is hydrogen, m is 1, n is 0, 1 or 2, and $R^6$ is chloro or methoxy located at the 4- or 7-position of the indazole ring system.

In compounds of formula II in which Ar is optionally substituted benzimidazolyl, the subject compounds may be represented by formula XIX:

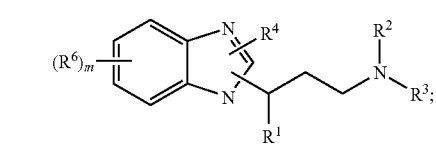

XIX wherein:
m is from 0 to 4;
$R^4$ is: hydrogen; alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)-SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy;

each $R^6$ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)-R^i$; $-(CH_2)_q-C(=O)-R^i$; or $-(CH_2)_q-N(R^f)-SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; and $R^1$, $R^2$ and $R^3$ are as defined herein.

In embodiments of formula II wherein Ar is optionally substituted benzimidazol-1-yl, the compounds of the invention may be more specifically of formula XX:

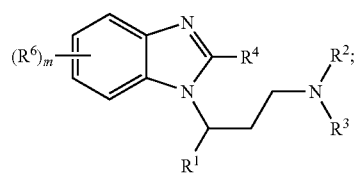

XX wherein m, $R^1$, $R^2$, $R^3$, $R^4$ and $R^6$ are as defined herein.

In embodiments of formula II wherein Ar is optionally substituted benzimidazol-2-yl, the compounds of the invention may be more specifically of formula V:

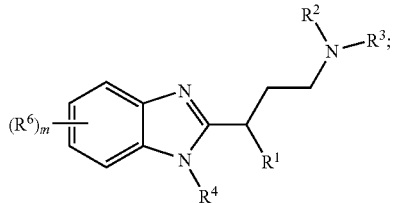

wherein m, $R^1$, $R^2$, $R^3$, $R^4$ and $R^6$ are as defined herein. In embodiments of formula XXI, $R^4$ is preferably hydrogen.

In compounds of formula II in which Ar is optionally substituted benzofuranyl, the subject compounds may be represented by formula XXII:

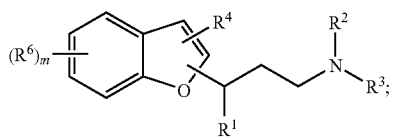

wherein:
m is from 0 to 4;
$R^4$ is: hydrogen; alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—$S(O)_rR^f$; —$(CH_2)_q$—$NR^gR^h$; —$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—$N(R^f)$—C(=O)—$R^i$; —$(CH_2)_q$—C(=O)—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy;

each $R^6$ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—$S(O)_rR^f$; —$(CH_2)_q$—$NR^gR^h$; —$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—$N(R^f)$—C(=O)—$R^i$; —$(CH_2)_q$—C(=O)—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; and $R^1$, $R^2$ and $R^3$ are as defined herein.

In embodiments of formula II wherein Ar is optionally substituted benzofuranyl, the compounds of the invention may be more specifically of formula XXIII:

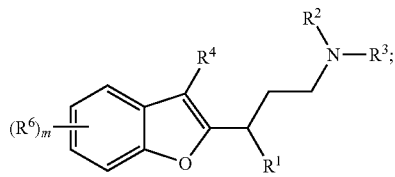

wherein m, $R^1$, $R^2$, $R^3$, $R^4$ and $R^6$ are as defined herein.

In embodiments of formula II wherein Ar is optionally substituted benzofuranyl, the compounds of the invention may be more specifically of formula XXIV:

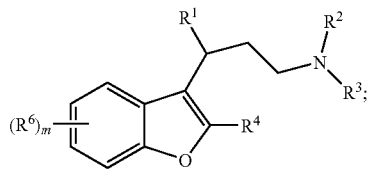

wherein m, $R^1$, $R^2$, $R^3$, $R^4$ and $R^6$ are as defined herein.

In compounds of formula II in which Ar is optionally substituted benzothiophenyl, the subject compounds may be represented by formula XXV:

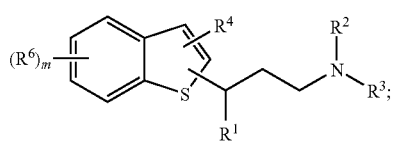

wherein:
m is from 0 to 4;
$R^4$ is: hydrogen; alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—$S(O)_rR^f$; —$(CH_2)_q$—$NR^gR^h$; —$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—$N(R^f)$—C(=O)—$R^i$; —$(CH_2)_q$—C(=O)—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy;

each $R^6$ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—$S(O)_rR^f$; —$(CH_2)_q$—$NR^gR^h$; —$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—$N(R^f)$—C(=O)—$R^i$; —$(CH_2)_q$—C(=O)—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; and $R^1$, $R^2$ and $R^3$ are as defined herein.

In embodiments of formula II wherein Ar is optionally substituted benzothiophenyl, the compounds of the invention may be more specifically of formula XXIII:

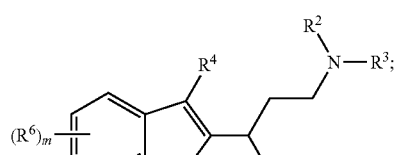

XXVI wherein m, $R^1$, $R^2$, $R^3$, $R^4$ and $R^6$ are as defined herein.

In embodiments of formula II wherein Ar is optionally substituted benzothiophenyl, the compounds of the invention may be more specifically of formula XXIV:

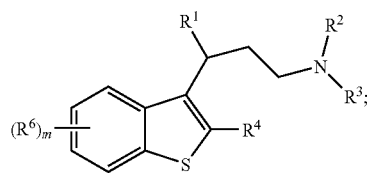

XXVII wherein m, $R^1$, $R^2$, $R^3$, $R^4$ and $R^6$ are as defined herein.

In embodiments of formula II wherein Ar is optionally substituted benzoxazol-2-yl, the compounds of the invention may be more specifically of formula V:

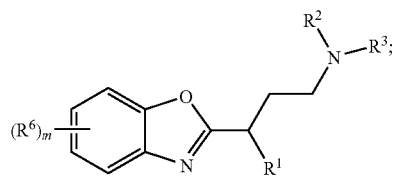

XXVIII wherein m, $R^1$, $R^2$, $R^3$ and $R^6$ are as defined herein.

In embodiments of formula II wherein Ar is optionally substituted benzothiazol-2-yl, the compounds of the invention may be more specifically of formula V:

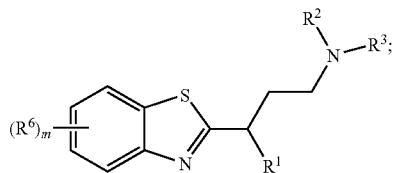

XXIX wherein m, $R^1$, $R^2$, $R^3$ and $R^6$ are as defined herein.

In compounds of formula II in which Ar is optionally substituted 2,3-dihydroindolyl, the subject compounds may be represented by formula XXX:

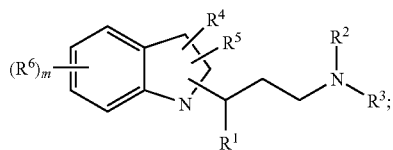

XXX wherein:

m is from 0 to 4;

$R^4$ and $R^5$ each independently is: hydrogen; alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—$S(O)_rR^f$; —$(CH_2)_q$—$NR^gR^h$; —$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—$N(R^f)$—C(=O)—$R^i$; —$(CH_2)_q$—C(=O)—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy;

each $R^6$ is independently: alkyl, alkoxy, halo, haloalkyl, haloalkoxy, cyano, nitro, hydroxyalkyl, heteroalkyl, alkoxyalkyl, benzyloxy, cycloalkoxy, cycloalkylalkoxy, optionally substituted thienyl, optionally substituted pyrazolyl, morpholinocarbonyl, —$(CH_2)_q$—$S(O)_rR^f$; —$(CH_2)_q$—$NR^gR^h$; —$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—$N(R^f)$—C(=O)—$R^i$; —$(CH_2)_q$—C(=O)—$R^i$; or —$(CH_2)_q$—$N(R^f)$—$SO_2$—$R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy; and $R^1$, $R^2$ and $R^3$ are as defined herein.

In embodiments of formula II wherein Ar is optionally substituted 2,3-dihydroindol-1-yl, the compounds of the invention may be more specifically of formula XXXI:

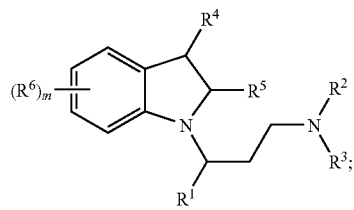

XXXI wherein m, $R^1$, $R^2$, $R^3$, $R^4$, $R^5$ and $R^6$ are as defined herein.

In embodiments of formula II wherein Ar is optionally substituted 2,3-dihydroindol-2-yl, the compounds of the invention may be more specifically of formula XXXII:

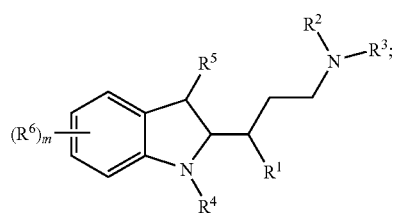

XXXII wherein m, $R^1$, $R^2$, $R^3$, $R^4$, $R^5$ and $R^6$ are as defined herein.

In embodiments of formula II wherein Ar is optionally substituted 2,3-dihydroindol-3-yl, the compounds of the invention may be more specifically of formula XXXIII:

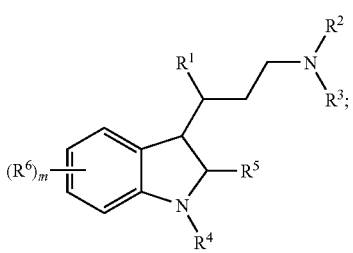

XXXIII wherein m, $R^1$, $R^2$, $R^3$, $R^4$, $R^5$ and $R^6$ are as defined herein.

Unless otherwise indicated, where any of $R^1$, $R^2$, $R^3$, $R^4$, $R^5$, $R^6$, $R^7$, $R^a$, $R^b$, $R^c$, $R^d$, $R^e$, $R^f$, $R^g$ or $R^h$ are alkyl or contain an alkyl moiety, such alkyl is preferably lower alkyl, i.e. $C_1$-$C_6$alkyl, and more preferably $C_1$-$C_4$alkyl.

Representative compounds in accordance with the methods of the invention are shown in Table 1.

TABLE 1

| # | Structure | Name | Example | MP or M + H |
|---|-----------|------|---------|-------------|
| 1 | 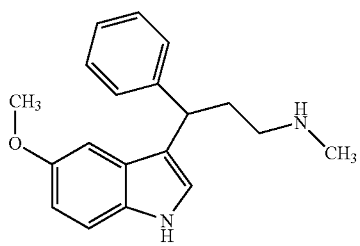 | [3-(5-Methoxy-1H-indol-3-yl)-3-phenyl-propyl]-methyl-amine | 1 | 295 |
| 2 | 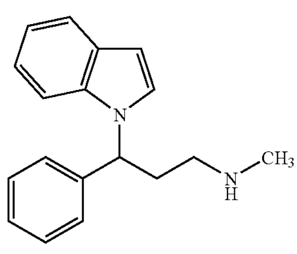 | (3-Indol-1-yl-3-phenyl-propyl)-methyl-amine | 3 | 265 |
| 3 | 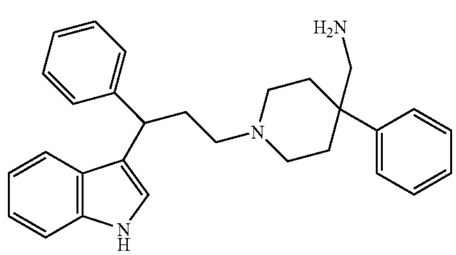 | C-{1-[3-(1H-Indol-3-yl)-3-phenyl-propyl]-4-phenyl-piperidin-4-yl}-methylamine | 1 | 424 |

TABLE 1-continued

| # | Structure | Name | Example | MP or M + H |
|---|-----------|------|---------|-------------|
| 4 | 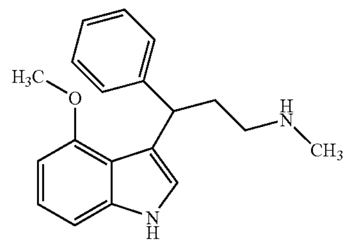 | [3-(4-Methoxy-1H-indol-3-yl)-3-phenyl-propyl]-methyl-amine | 1, 2 | 295 |
| 5 | 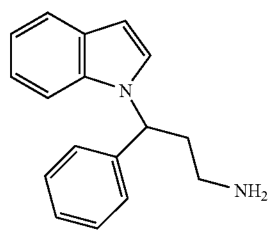 | 3-Indol-1-yl-3-phenyl-propylamine | 3 | 251 |
| 6 | 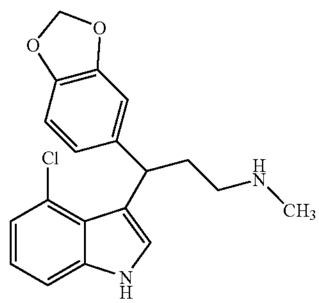 | [3-Benzo[1,3]dioxol-5-yl-3-(4-chloro-1H-indol-3-yl)-propyl]-methyl-amine | 1 | 344 |
| 7 | 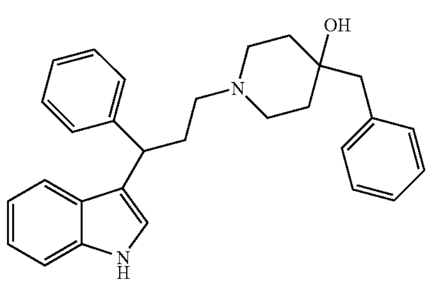 | 4-Benzyl-1-[3-(1H-indol-3-yl)-3-phenyl-propyl]-piperidin-4-ol | | 426 |
| 8 | 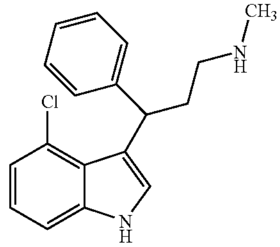 | [3-(4-Chloro-1H-indol-3-yl)-3-phenyl-propyl]-methyl-amine | 1, 2 | 300 |

TABLE 1-continued

| # | Structure | Name | Example | MP or M + H |
|---|---|---|---|---|
| 9 | 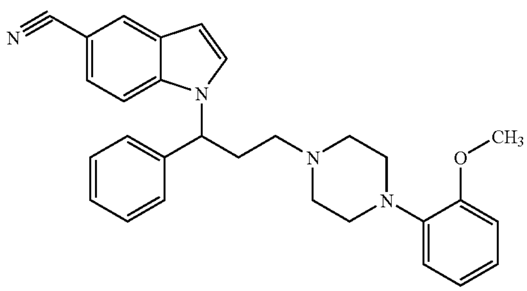 | 1-{3-[4-(2-Methoxy-phenyl)-piperazin-1-yl]-1-phenyl-propyl}-1H-indole-5-carbonitrile | 3 | 452 |
| 10 | 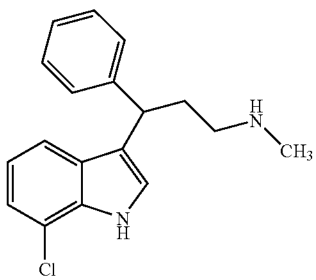 | [3-(7-Chloro-1H-indol-3-yl)-3-phenyl-propyl]-methyl-amine | 1 | 300 |
| 11 | 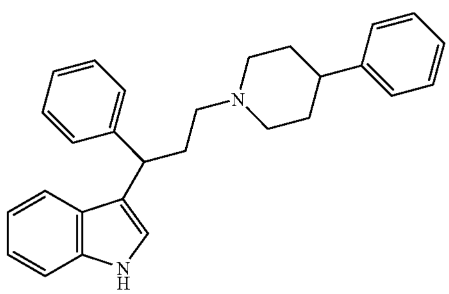 | 3-[1-Phenyl-3-(4-phenyl-piperidin-1-yl)-propyl]-1H-indole | 1 | 396 |
| 12 | 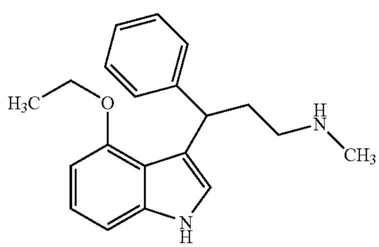 | [3-(4-Ethoxy-1H-indol-3-yl)-3-phenyl-propyl]-methyl-amine | 1 | 309 |
| 13 | 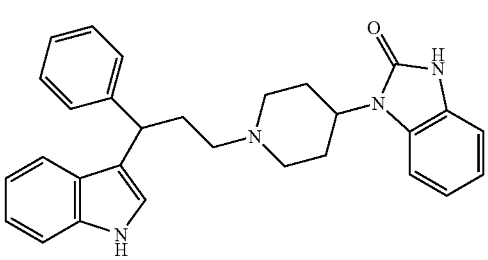 | 1-{1-[3-(1H-Indol-3-yl)-3-phenyl-propyl]-piperidin-4-yl}-1,3-dihydro-benzoimidazol-2-one | 1 | 452 |

TABLE 1-continued

| # | Structure | Name | Example | MP or M + H |
|---|---|---|---|---|
| 14 | 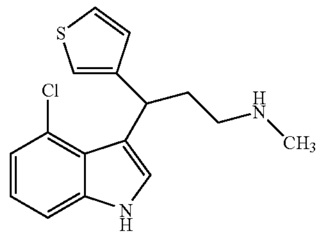 | [3-(4-Chloro-1H-indol-3-yl)-3-thiophen-3-yl-propyl]-methyl-amine | 1 | 306 |
| 15 | 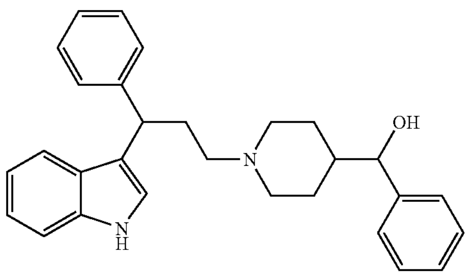 | {1-[3-(1H-Indol-3-yl)-3-phenyl-propyl]-piperidin-4-yl}-phenyl-methanol | 1 | 426 |
| 16 | 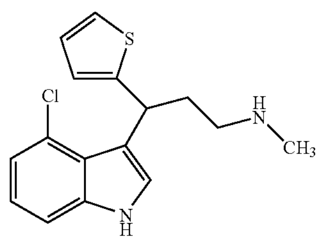 | [3-(4-Chloro-1H-indol-3-yl)-3-thiophen-2-yl-propyl]-methyl-amine | 1 | 306 |
| 17 | 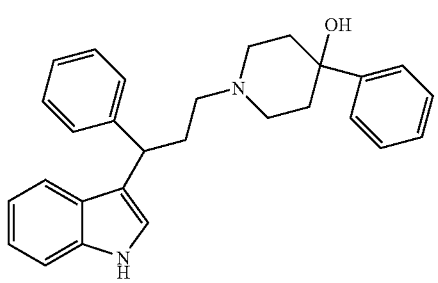 | 1-[3-(1H-Indol-3-yl)-3-phenyl-propyl]-4-phenyl-piperidin-4-ol | 1 | 412 |
| 18 | 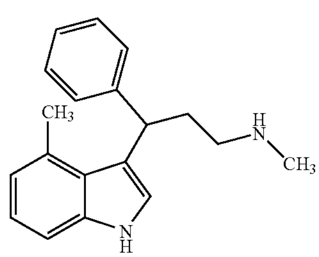 | Methyl-[3-(4-methyl-1H-indol-3-yl)-3-phenyl-propyl]-amine | 1 | 279 |
| 19 | 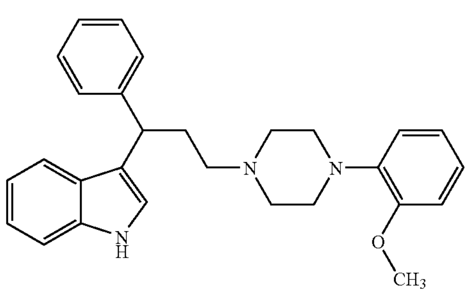 | 3-{3-[4-(2-Methoxy-phenyl)-piperazin-1-yl]-1-phenyl-propyl}-1H-indole | 1 | 427 |

TABLE 1-continued

| # | Structure | Name | Example | MP or M + H |
|---|---|---|---|---|
| 20 | 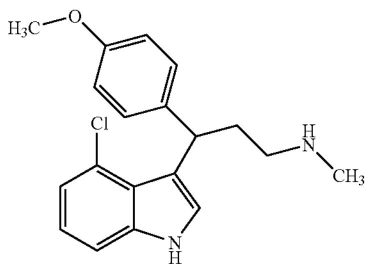 | 3-(4-Chloro-1H-indol-3-yl)-3-(4-methoxy-phenyl)-propyl]-methyl-amine | 1 | 330 |
| 21 | 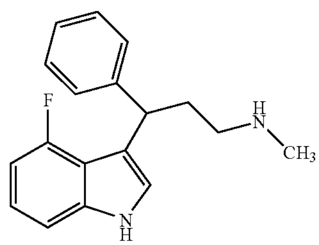 | [3-(4-Fluoro-1H-indol-3-yl)-3-phenyl-propyl]-methyl-amine | 1 | 283 |
| 22 | 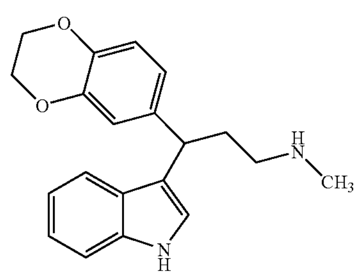 | [3-(2,3-Dihydro-benzo[1,4]dioxin-6-yl)-3-(1H-indol-3-yl)-propyl]-methyl-amine | 1 | 323 |
| 23 | 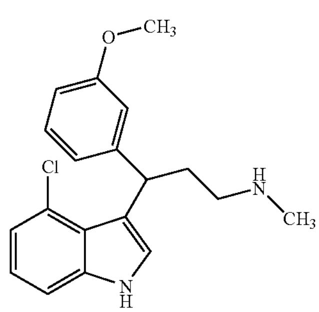 | [3-(4-Chloro-1H-indol-3-yl)-3-(3-methoxy-phenyl)-propyl]-methyl-amine | 1 | 330 |
| 24 | 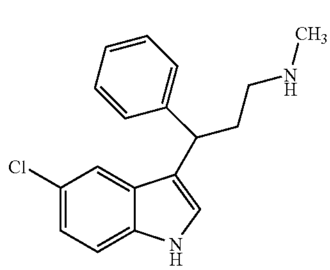 | [3-(5-Chloro-1H-indol-3-yl)-3-phenyl-propyl]-methyl-amine | 1, 2 | 300 |

TABLE 1-continued

| # | Structure | Name | Example | MP or M + H |
|---|---|---|---|---|
| 25 | 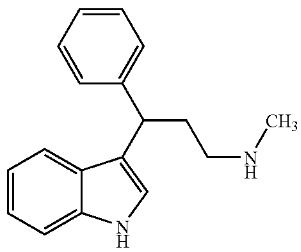 | [3-(1H-Indol-3-yl)-3-phenyl-propyl]-methyl-amine | 1, 2 | 265 |
| 26 | 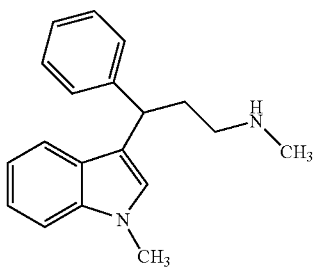 | Methyl-[3-(1-methyl-1H-indol-3-yl)-3-phenyl-propyl]-amine | 1 | 279 |
| 27 | 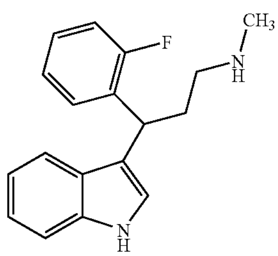 | [3-(2-Fluoro-phenyl)-3-(1H-indol-3-yl)-propyl]-methyl-amine | 1 | 283 |
| 28 | 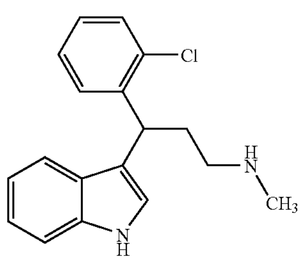 | [3-(2-Chloro-phenyl)-3-(1H-indol-3-yl)-propyl]-methyl-amine | 1 | 300 |
| 29 | 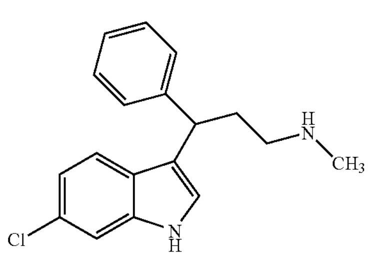 | [3-(6-Chloro-1H-indol-3-yl)-3-phenyl-propyl]-methyl-amine | 1 | 300 |

TABLE 1-continued

| # | Structure | Name | Example | MP or M + H |
|---|---|---|---|---|
| 30 | 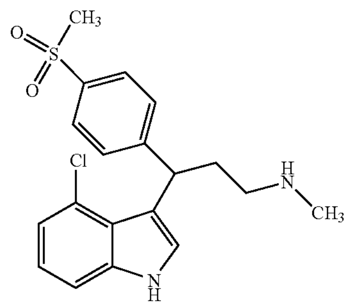 | [3-(4-Chloro-1H-indol-3-yl)-3-(4-methanesulfonyl-phenyl)-propyl]-methyl-amine | 1 | 378 |
| 31 | 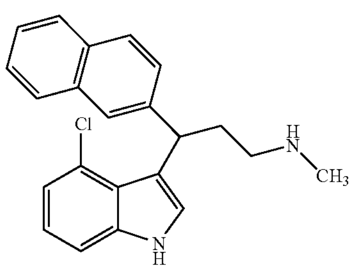 | [3-(4-Chloro-1H-indol-3-yl)-3-naphthalen-2-yl-propyl]-methyl-amine | 1 | 350 |
| 32 | 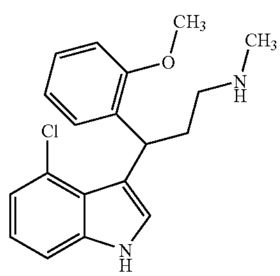 | [3-(4-Chloro-1H-indol-3-yl)-3-(2-methoxy-phenyl)-propyl]-methyl-amine | 1 | 330 |
| 33 | 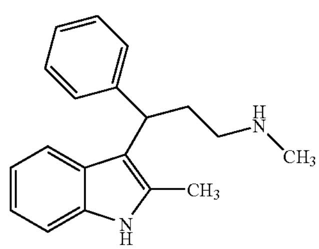 | Methyl-[3-(2-methyl-1H-indol-3-yl)-3-phenyl-propyl]-amine | 1 | 279 |
| 34 | 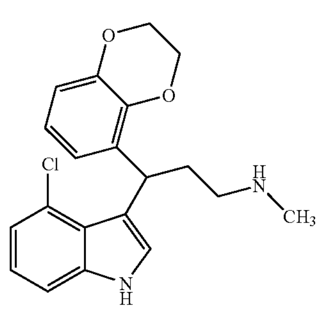 | [3-(4-Chloro-1H-indol-3-yl)-3-(2,3-methyl-amine | 1 | 358 |

TABLE 1-continued

| # | Structure | Name | Example | MP or M + H |
|---|---|---|---|---|
| 35 | 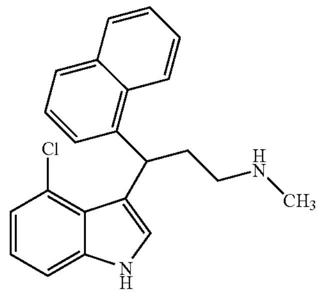 | [3-(4-Chloro-1H-indol-3-yl)-3-naphthalen-1-yl-propyl]-methyl-amine | 1 | 350 |
| 36 | 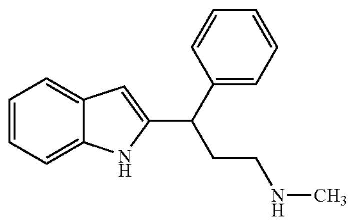 | [3-(1H-Indol-2-yl)-3-phenyl-propyl]-methyl-amine | 4 | 265 |
| 37 | 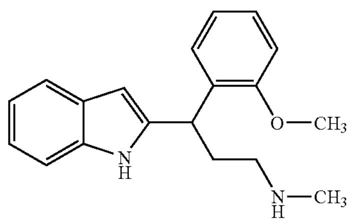 | [3-(1H-Indol-2-yl)-3-(2-methoxy-phenyl)-propyl]-methyl-amine | 4 | 295 |
| 38 | 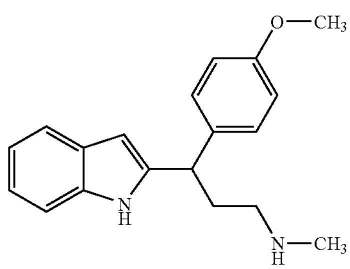 | [3-(1H-Indol-2-yl)-3-(4-methoxy-phenyl)-propyl]-methyl-amine | 4 | 295 |
| 39 | 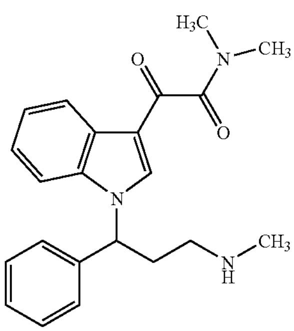 | N,N-Dimethyl-2-[1-(3-methylamino-1-phenyl-propyl)-1H-indol-3-yl]-2-oxo-acetamide | 3 | 364 |
| 40 | 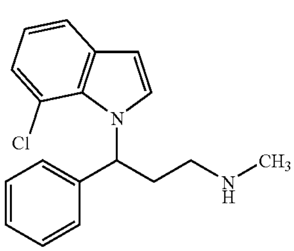 | [3-(7-Chloro-indol-1-yl)-3-phenyl-propyl]-methyl-amine | 3 | 299 |

TABLE 1-continued

| # | Structure | Name | Example | MP or M + H |
|---|---|---|---|---|
| 41 | 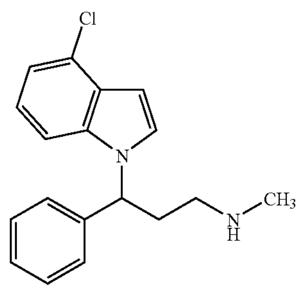 | [3-(4-Chloro-indol-1-yl)-3-phenyl-propyl]-methyl-amine | 3 | 299 |
| 42 | 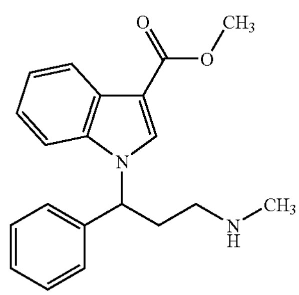 | 1-(3-Methylamino-1-phenyl-propyl)-1H-indole-3-carboxylic acid methyl ester | 3 | 323 |
| 43 | 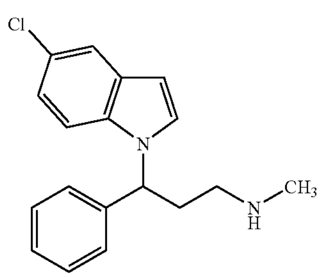 | [3-(5-Chloro-indol-1-yl)-3-phenyl-propyl]-methyl-amine | 3 | 299 |
| 44 | 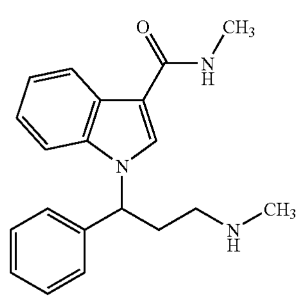 | 1-(3-Methylamino-1-phenyl-propyl)-1H-indole-3-carboxylic acid methylamide | 3 | 321 |
| 45 | 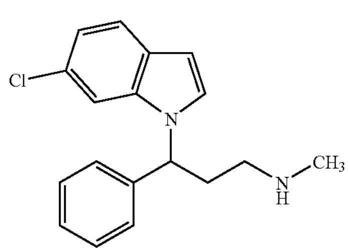 | [3-(6-Chloro-indol-1-yl)-3-phenyl-propyl]-methyl-amine | 3 | 299 |

TABLE 1-continued

| # | Structure | Name | Example | MP or M + H |
|---|---|---|---|---|
| 46 | 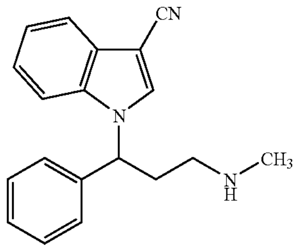 | 1-(3-Methylamino-1-phenyl-propyl)-1H-indole-3-carbonitrile | 3 | 290 |
| 47 | 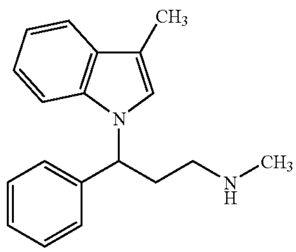 | Methyl-[3-(3-methyl-indol-1-yl)-3-phenyl-propyl]-amine | 3 | 279 |
| 48 | 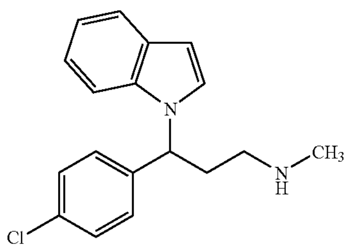 | [3-(4-Chloro-phenyl)-3-indol-1-yl-propyl]-methyl-amine | 3 | 299 |
| 49 | 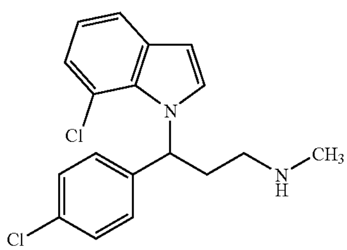 | [3-(7-Chloro-indol-1-yl)-3-(4-chloro-phenyl)-propyl]-methyl-amine | 3 | 333 |
| 50 | 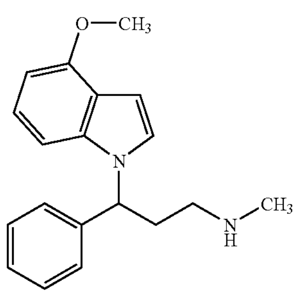 | [3-(4-Methoxy-indol-1-yl)-3-phenyl-propyl]-methyl-amine | 3 | 295 |
| 51 | 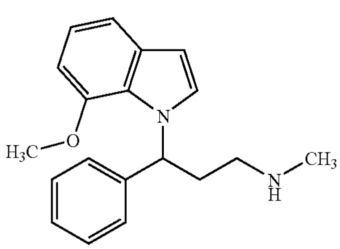 | [3-(7-Methoxy-indol-1-yl)-3-phenyl-propyl]-methyl-amine | 3 | 295 |

TABLE 1-continued

| # | Structure | Name | Example | MP or M + H |
|---|-----------|------|---------|-------------|
| 52 | 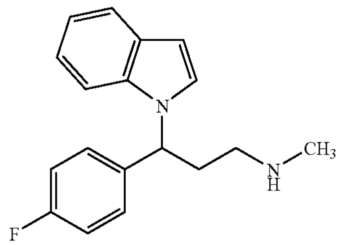 | [3-(4-Fluoro-phenyl)-3-indol-1-yl-propyl]-methyl-amine | 3 | 283 |
| 53 | 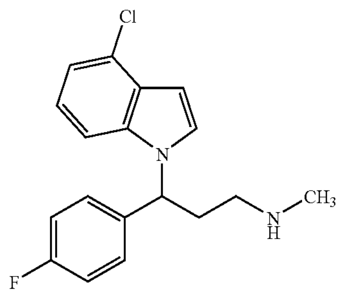 | [3-(4-Chloro-indol-1-yl)-3-(4-fluoro-phenyl)-propyl]-methyl-amine | 3 | 318 |
| 54 | 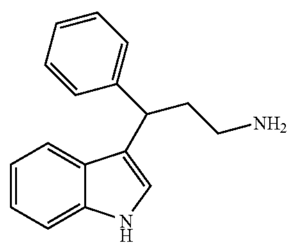 | 3-(1H-Indol-3-yl)-3-phenyl-propylamine | 1 | 251 |
| 55 | 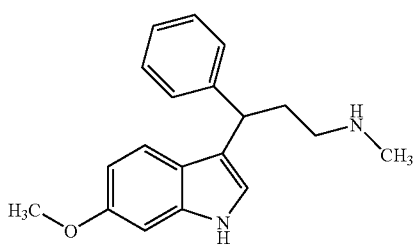 | [3-(6-Ethoxy-1H-indol-3-yl)-3-phenyl-propyl]-methyl-amine | 1 | 295 |
| 56 | 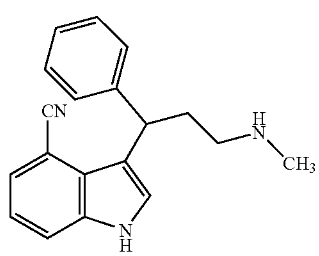 | 3-(3-Methylamino-1-phenyl-propyl)-1H-indole-4-carbonitrile | 2 | 290 |
| 57 | 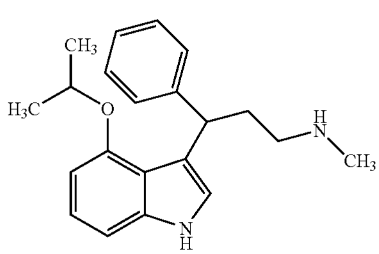 | [3-(4-Isopropoxy-1H-indol-3-yl)-3-phenyl-propyl]-methyl-amine | 1 | 323 |

TABLE 1-continued

| # | Structure | Name | Example | MP or M + H |
|---|---|---|---|---|
| 58 | 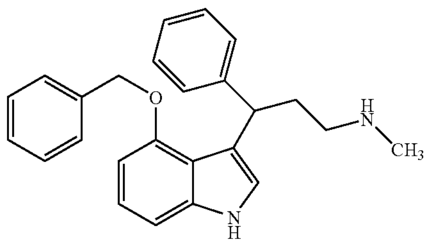 | [3-(4-Benzyloxy-1H-indol-3-yl)-3-phenyl-propyl]-methyl-amine | 1 | 371 |
| 59 | 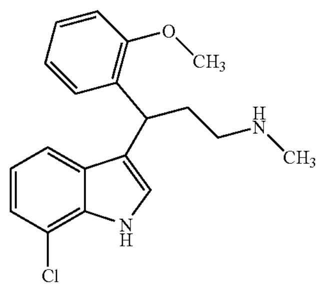 | [3-(7-Chloro-1H-indol-3-yl)-3-(2-methoxy-phenyl)-propyl]-methyl-amine | 1 | 330 |
| 60 | 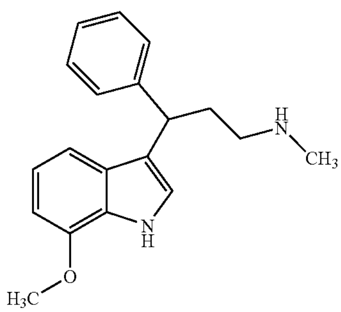 | [3-(7-Methoxy-1H-indol-3-yl)-3-phenyl-propyl]-methyl-amine | 1 | 295 |
| 61 | 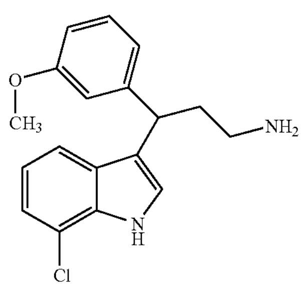 | 3-(7-Chloro-1H-indol-3-yl)-3-(3-methoxy-phenyl)-propylamine | 1 | 316 |
| 62 | 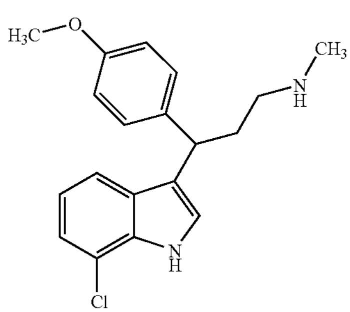 | [3-(7-Chloro-1H-indol-3-yl)-3-(4-methoxy-phenyl)-propyl]-methyl-amine | 1 | 330 |

TABLE 1-continued

| # | Structure | Name | Example | MP or M + H |
|---|---|---|---|---|
| 63 | 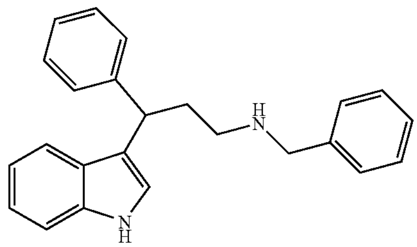 | (2-Ethylidene-hexa-3,5-dienyl)-[3-(1H-indol-3-yl)-3-phenyl-propyl]-amine | 1 | 341 |
| 64 | 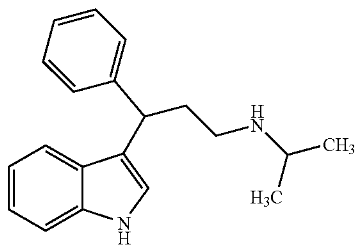 | [3-(1H-Indol-3-yl)-3-phenyl-propyl]-isopropyl-amine | 1 | 293 |
| 65 | 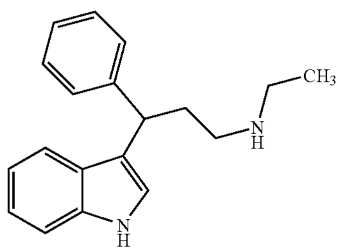 | Ethyl-[3-(1H-indol-3-yl)-3-phenyl-propyl]-amine | 1 | 279 |
| 66 | 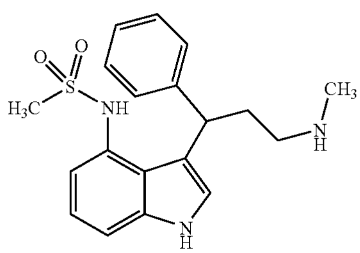 | N-[3-(3-Methylamino-1-phenyl-propyl)-1H-indol-4-yl]-methanesulfonamide | 2 | 358 |
| 67 | 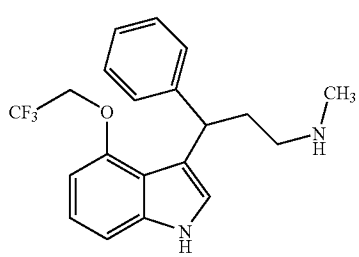 | Methyl-{3-phenyl-3-[4-(2,2,2-trifluoro-ethoxy)-1H-indol-3-yl]-propyl}-amine | 1 | 309 |
| 68 | 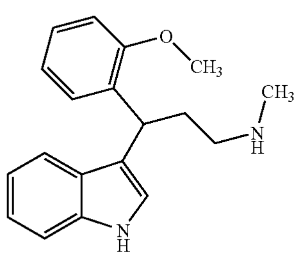 | [3-(1H-Indol-3-yl)-3-(2-methoxy-phenyl)-propyl]-methyl-amine | 1 | 295 |

TABLE 1-continued

| # | Structure | Name | Example | MP or M + H |
|---|---|---|---|---|
| 69 | 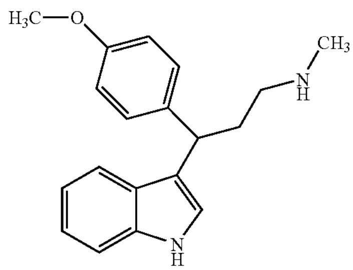 | [3-(1H-Indol-3-yl)-3-(4-methoxy-phenyl)-propyl]-methyl-amine | 1 | |
| 70 | 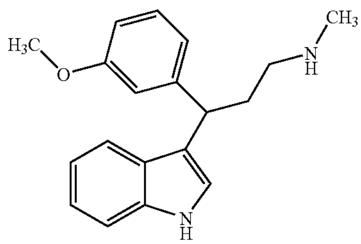 | [3-(1H-Indol-3-yl)-3-(3-methoxy-phenyl)-propyl]-methyl-amine | 1 | 295 |
| 71 | 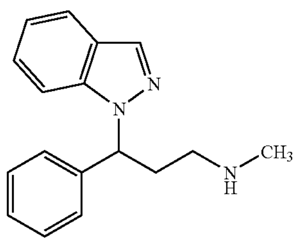 | (3-Indazol-1-yl-3-phenyl-propyl)-methyl-amine | 3 | 266 |
| 72 | 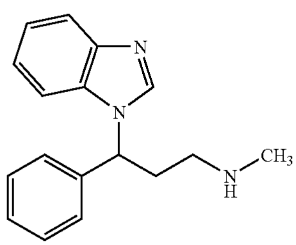 | (3-Benzoimidazol-1-yl-3-phenyl-propyl)-methyl-amine | 3 | 266 |
| 73 | 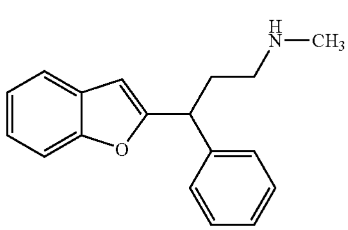 | (3-Benzofuran-2-yl-3-phenyl-propyl)-methyl-amine | 5 | 266 |
| 74 | 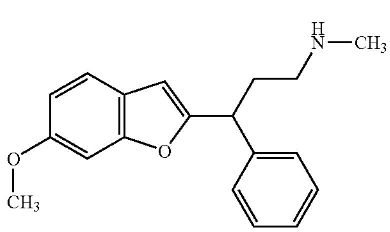 | [3-(6-Methoxy-benzofuran-2-yl)-3-phenyl-propyl]-methyl-amine | 5 | 296 |

TABLE 1-continued

| # | Structure | Name | Example | MP or M + H |
|---|---|---|---|---|
| 75 | 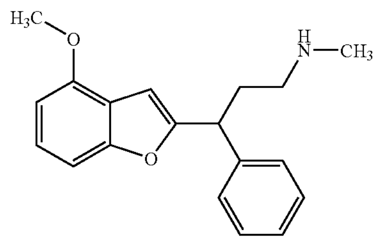 | [3-(4-Methoxy-benzofuran-2-yl)-3-phenyl-propyl]-methyl-amine | 5 | 296 |
| 76 | 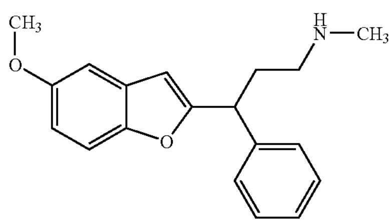 | [3-(5-Methoxy-benzofuran-2-yl)-3-phenyl-propyl]-methyl-amine | 5 | 296 |
| 77 | 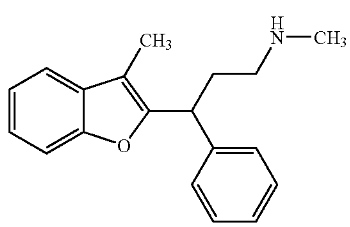 | Methyl-[3-(3-methyl-benzofuran-2-yl)-3-phenyl-propyl]-amine | 5 | 280 |
| 78 | 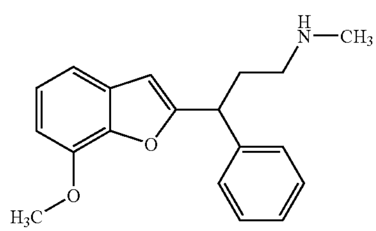 | [3-(7-Methoxy-benzofuran-2-yl)-3-phenyl-propyl]-methyl-amine | 5 | 296 |
| 79 | 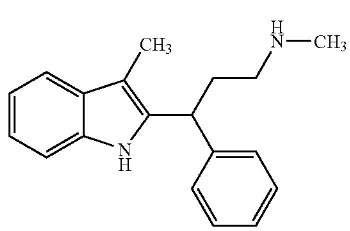 | Methyl-[3-(3-methyl-1H-indol-2-yl)-3-phenyl-propyl]-amine | 4 | 279 |
| 80 | 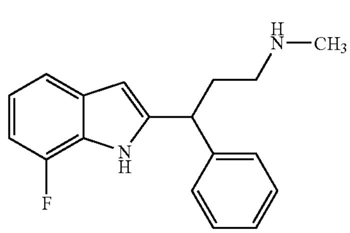 | [3-(7-Fluoro-1H-indol-2-yl)-3-phenyl-propyl]-methyl-amine | 4 | 283 |

TABLE 1-continued

| # | Structure | Name | Example | MP or M + H |
|---|-----------|------|---------|-------------|
| 81 | 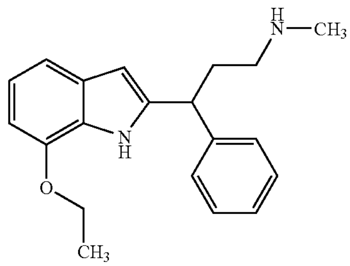 | [3-(7-Ethoxy-1H-indol-2-yl)-3-phenyl-propyl]-methyl-amine | 4 | 309 |
| 82 | 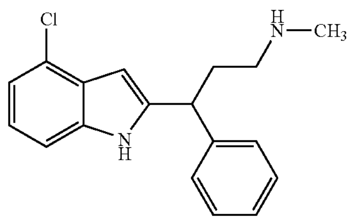 | [3-(4-Chloro-1H-indol-2-yl)-3-phenyl-propyl]-methyl-amine | 4 | 300 |
| 83 | 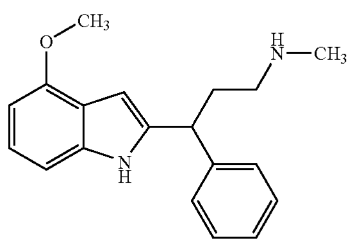 | [3-(4-Methoxy-1H-indol-2-yl)-3-phenyl-propyl]-methyl-amine | 4 | 295 |
| 84 | 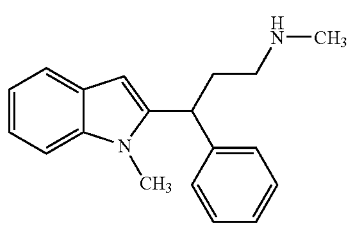 | Methyl-[3-(1-methyl-1H-indol-2-yl)-3-phenyl-propyl]-amine | 4 | 279 |
| 85 | 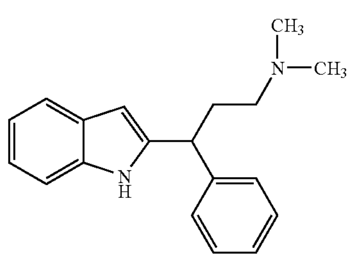 | [3-(1H-Indol-2-yl)-3-phenyl-propyl]-dimethyl-amine | 4 | 279 |
| 86 | 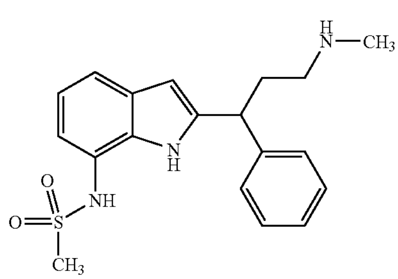 | N-[2-(3-Methylamino-1-phenyl-propyl)-1H-indol-7-yl]-methanesulfonamide | 4 | 358 |

TABLE 1-continued

| # | Structure | Name | Example | MP or M + H |
|---|---|---|---|---|
| 87 | 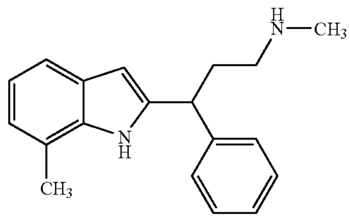 | Methyl-[3-(7-methyl-1H-indol-2-yl)-3-phenyl-propyl]-amine | 4 | 279 |
| 88 | 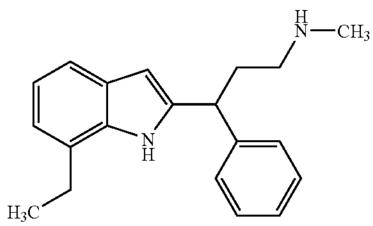 | [3-(7-Ethyl-1H-indol-2-yl)-3-phenyl-propyl]-methyl-amine | 4 | 293 |
| 89 | 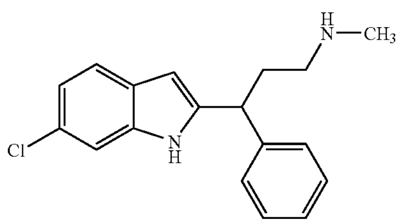 | [3-(6-Chloro-1H-indol-2-yl)-3-phenyl-propyl]-methyl-amine | 4 | 300 |
| 90 | 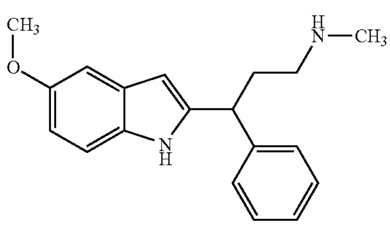 | [3-(5-Methoxy-1H-indol-2-yl)-3-phenyl-propyl]-methyl-amine | 4 | 295 |
| 91 | 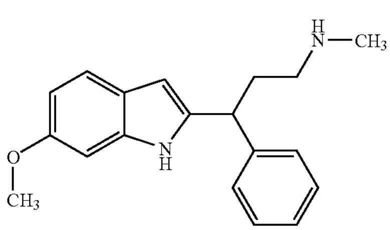 | [3-(6-Methoxy-1H-indol-2-yl)-3-phenyl-propyl]-methyl-amine | 4 | 295 |
| 92 | 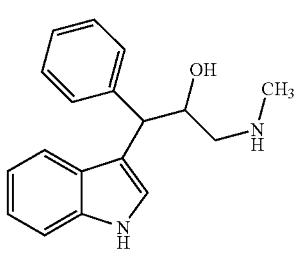 | 1-(1H-Indol-3-yl)-3-methylamino-1-phenyl-propan-2-ol | 1 | 281 |

TABLE 1-continued

| # | Structure | Name | Example | MP or M + H |
|---|---|---|---|---|
| 93 | 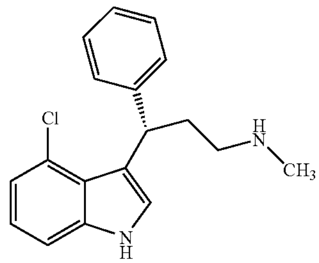 | (S)-[3-(4-Chloro-1H-indol-3-yl)-3-phenyl-propyl]-methyl-amine | 1, 9 | 300 |
| 94 | 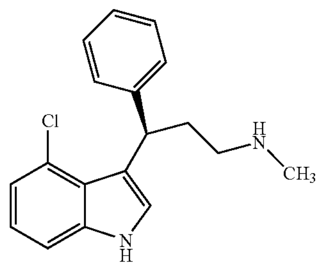 | (R)-[3-(4-Chloro-1H-indol-3-yl)-3-phenyl-propyl]-methyl-amine | 1, 9 | 300 |
| 95 | 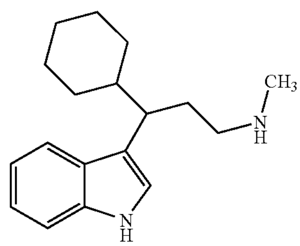 | [3-Cyclohexyl-3-(1H-indol-3-yl)-propyl]-methyl-amine | 10 | 271 |
| 96 | 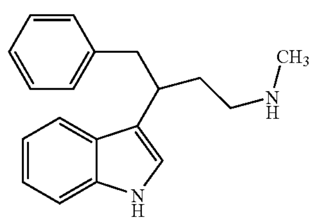 | [3-(1H-Indol-3-yl)-4-phenyl-butyl]-methyl-amine | 10 | 279 |
| 97 | 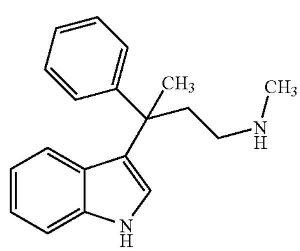 | [3-(1H-Indol-3-yl)-3-phenyl-butyl]-methyl-amine | 1 | 289 |
| 98 | 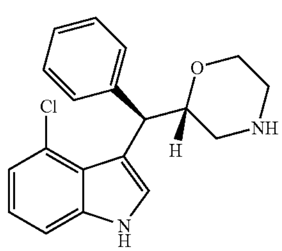 | 4-Chloro-3-(morpholin-2-yl-phenyl-methyl)-1H-indole | 1 | 328 |

TABLE 1-continued

| # | Structure | Name | Example | MP or M + H |
|---|---|---|---|---|
| 99 | 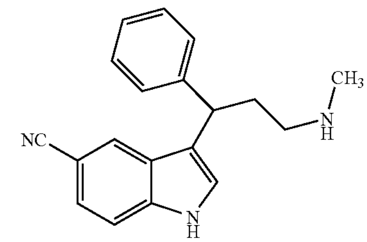 | 3-(3-Methylamino-1-phenyl-propyl)-1H-indole-5-carbonitrile | 1 | 290 |
| 100 | 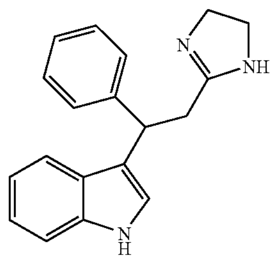 | 3-[2-(4,5-Dihydro-1H-imidazol-2-yl)-1-phenyl-ethyl]-1H-indole | 1 | 290 |
| 101 | 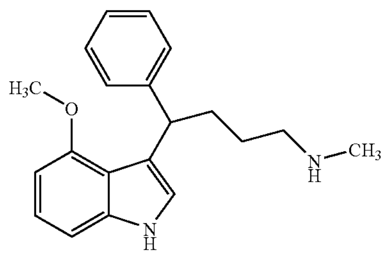 | [4-(4-Methoxy-1H-indol-3-yl)-4-phenyl-butyl]-methyl-amine | 2 | 309 |
| 102 | 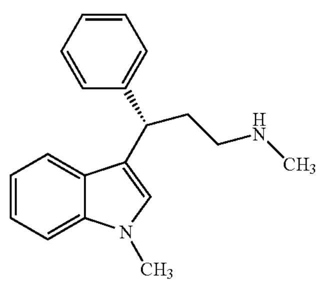 | (S)-Methyl-[3-(1-methyl-1H-indol-3-yl)-3-phenyl-propyl]-amine | 1, 9 | 279 |
| 103 | 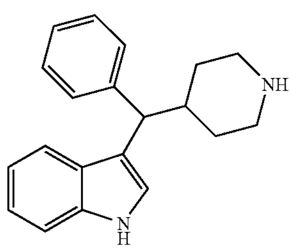 | 3-(Phenyl-piperidin-4-yl-methyl)-1H-indole | 2 | 291 |
| 104 | 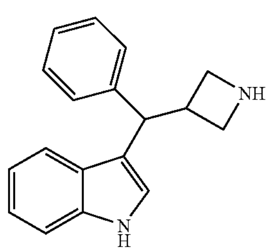 | 3-(Azetidin-3-yl-phenyl-methyl)-1H-indole | 2 | 263 |

TABLE 1-continued

| # | Structure | Name | Example | MP or M + H |
|---|---|---|---|---|
| 105 | 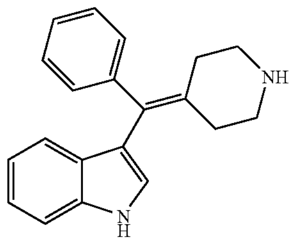 | 3-(Phenyl-piperidin-4-ylidene-methyl)-1H-indole | 2 | 289 |
| 106 | 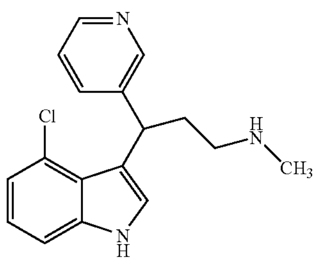 | [3-(4-Chloro-1H-indol-3-yl)-3-pyridin-3-yl-propyl]-methyl-amine | 1 | 301 |
| 107 | 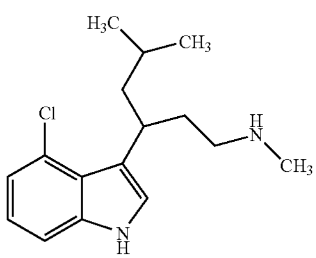 | [3-(4-Chloro-1H-indol-3-yl)-5-methyl-hexyl]-methyl-amine | 10 | 280 |
| 108 | 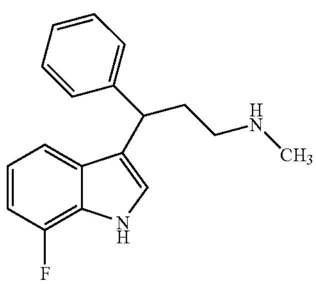 | [3-(7-Fluoro-1H-indol-3-yl)-3-phenyl-propyl]-methyl-amine | 1 | 283 |
| 109 | 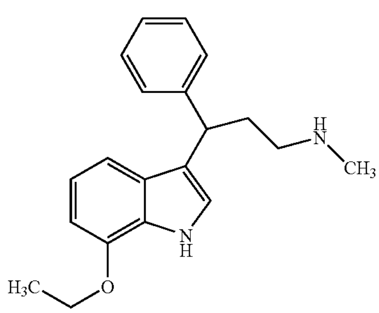 | [3-(7-Ethoxy-1H-indol-3-yl)-3-phenyl-propyl]-methyl-amine | 1 | 309 |

TABLE 1-continued

| # | Structure | Name | Example | MP or M + H |
|---|---|---|---|---|
| 110 | 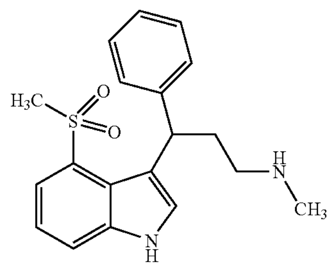 | [3-(4-Methanesulfonyl-1H-indol-3-yl)-3-phenyl-propyl]-methyl-amine | 1 | 343 |
| 111 | 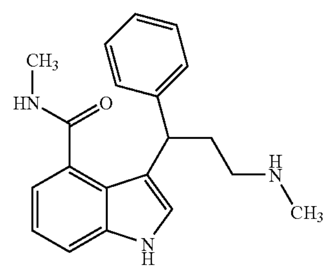 | 3-(3-Methylamino-1-phenyl-propyl)-1H-indole-4-carboxylic acid methylamide | 1 | 322 |
| 112 | 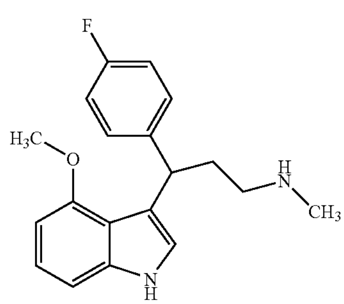 | [3-(4-Fluoro-phenyl)-3-(4-methoxy-1H-indol-3-yl)-propyl]-methyl-amine | 1 | 313 |
| 113 | 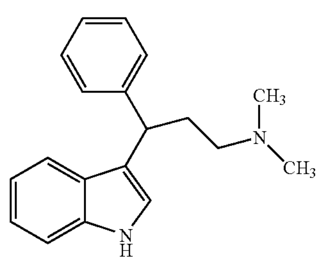 | [3-(1H-Indol-3-yl)-3-phenyl-propyl]-dimethyl-amine | 1 | 279 |
| 114 | 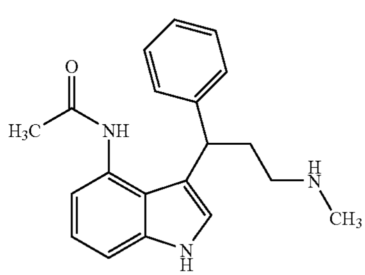 | N-[3-(3-Methylamino-1-phenyl-propyl)-1H-indol-4-yl]-acetamide | 1 | 322 |

TABLE 1-continued

| # | Structure | Name | Example | MP or M + H |
|---|---|---|---|---|
| 115 | 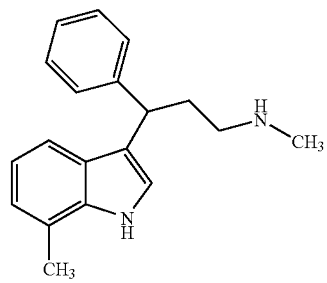 | Methyl-[3-(7-methyl-1H-indol-3-yl)-3-phenyl-propyl]-amine | 1 | 279 |
| 116 | 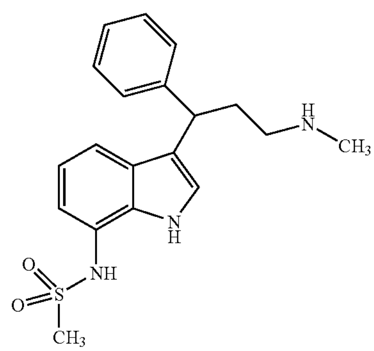 | N-[3-(3-Methylamino-1-phenyl-propyl)-1H-indol-7-yl]-methanesulfonamide | 1 | 358 |
| 117 | 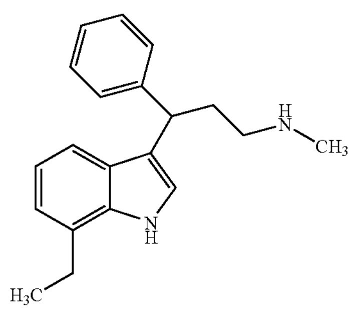 | [3-(7-Ethyl-1H-indol-3-yl)-3-phenyl-propyl]-methyl-amide | 1 | 293 |
| 118 | 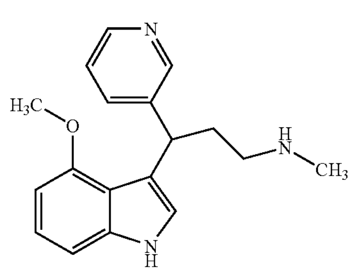 | [3-(4-Methoxy-1H-indol-3-yl)-3-pyridin-3-yl-propyl]-methyl-amine | 1 | 296 |
| 119 | 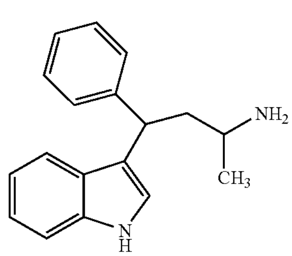 | 3-(1H-Indol-3-yl)-1-methyl-3-phenyl-propylamine | 1 | 265 |

TABLE 1-continued

| # | Structure | Name | Example | MP or M + H |
|---|---|---|---|---|
| 120 | 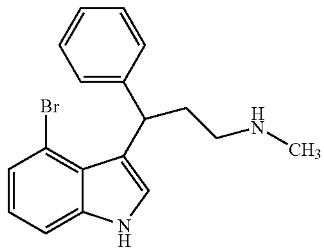 | [3-(4-Bromo-1H-indol-3-yl)-3-phenyl-propyl]-methyl-amine | 1 | 244 |
| 121 | 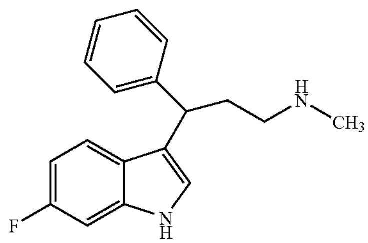 | [3-(6-Fluoro-1H-indol-3-yl)-3-phenyl-propyl]-methyl-amine | 1 | 283 |
| 122 | 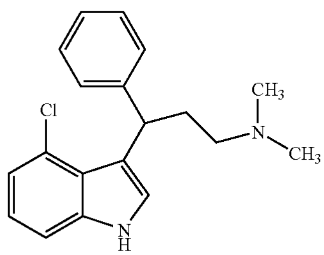 | [3-(4-Chloro-1H-indol-3-yl)-3-phenyl-propyl]-dimethyl-amine | 1 | 314 |
| 123 | 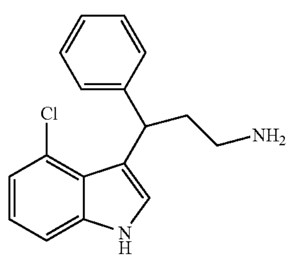 | 3-(4-Chloro-1H-indol-3-yl)-3-phenyl-propylamine | 1 | 286 |
| 124 | 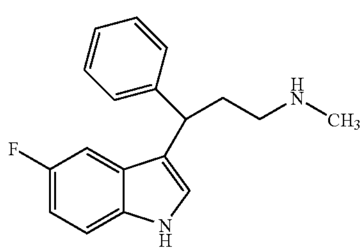 | [3-(4-Fluoro-1H-indol-3-yl)-3-phenyl-propyl]-methyl-amine | 1 | 283 |
| 125 | 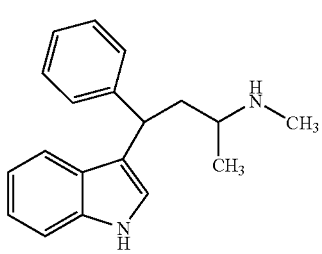 | [3-(1H-Indol-3-yl)-1-methyl-3-phenyl-propyl]-methyl-amine | 1 | 279 |

TABLE 1-continued

| # | Structure | Name | Example | MP or M + H |
|---|---|---|---|---|
| 126 | 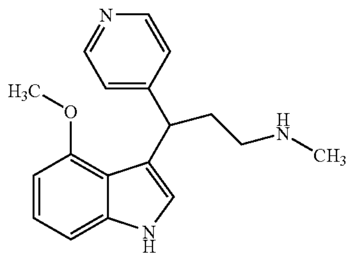 | [3-(4-Methoxy-1H-indol-3-yl)-3-pyridin-4-yl-propyl]-methyl-amine | 6 | 296 |
| 127 | 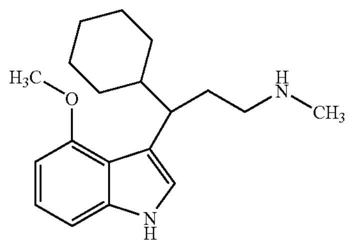 | [3-Cyclohexyl-3-(4-methoxy-1H-indol-3-yl)-propyl]-methyl-amine | 10 | 301 |
| 128 | 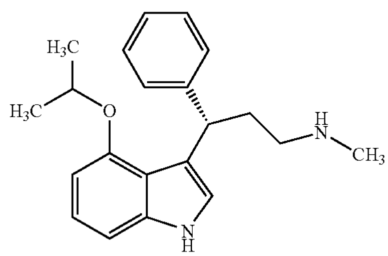 | (S)-[3-(4-Isopropoxy-1H-indol-3-yl)-3-phenyl-propyl]-methyl-amine | 1, 9 | 323 |
| 129 | 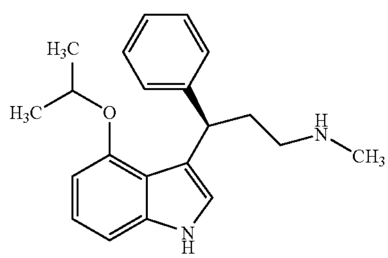 | (R)-[3-(4-Isopropoxy-1H-indol-3-yl)-3-phenyl-propyl]-methyl-amine | 1, 9 | 323 |
| 130 | 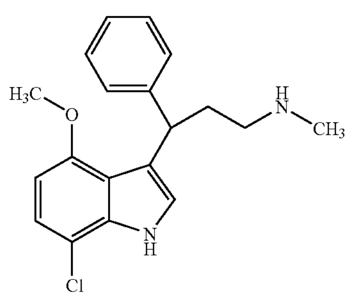 | [3-(7-Chloro-4-methoxy-1H-indol-3-yl)-3-phenyl-propyl]-methyl-amine | 1 | 330 |
| 131 | 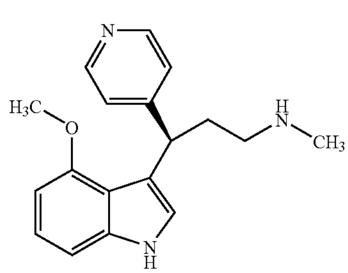 | (R)-[3-(4-Methoxy-1H-indol-3-yl)-3-pyridin-4-yl-propyl]-methyl-amine | 6 | 296 |

TABLE 1-continued

| # | Structure | Name | Example | MP or M + H |
|---|---|---|---|---|
| 132 | 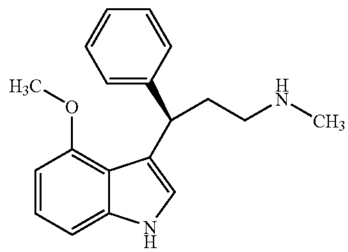 | (R)-[3-(4-Methoxy-1H-indol-3-yl)-3-phenyl-propyl]-methyl-amine | 1, 9 | 295 |
| 133 | 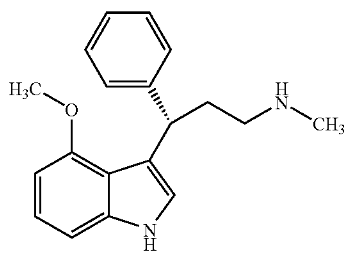 | (S)-[3-(4-Methoxy-1H-indol-3-yl)-3-phenyl-propyl]-methyl-amine | 1, 9 | 295 |
| 134 | 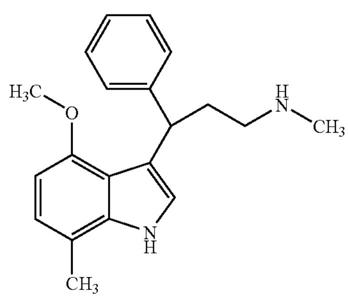 | [3-(4-Methoxy-7-methyl-1H-indol-3-yl)-3-phenyl-propyl]-methyl-amine | 1 | 309 |
| 135 | 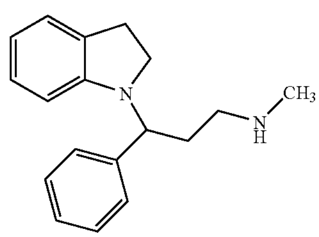 | [3-(2,3-Dihydro-indol-1-yl)-3-phenyl-propyl]-methyl-amine | 7 | 267 |
| 136 | 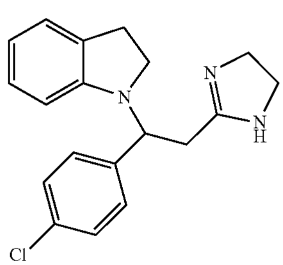 | 1-[1-(4-Chloro-phenyl)-2-(4,5-dihydro-1H-imidazol-2-yl)-ethyl]-2,3-dihydro-1H-indole | 7 | 327 |
| 137 | 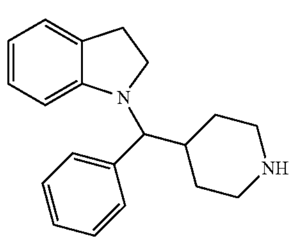 | 1-(Phenyl-piperidin-4-yl-methyl)-2,3-dihydro-1H-indole | 7 | 293 |

TABLE 1-continued

| # | Structure | Name | Example | MP or M + H |
|---|-----------|------|---------|-------------|
| 138 | 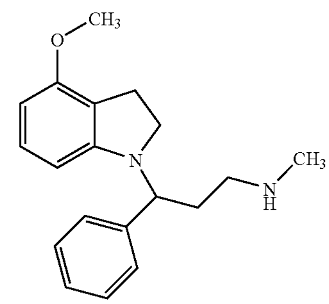 | [3-(4-Methoxy-2,3-dihydro-indol-1-yl)-3-phenyl-propyl]-methyl-amine | 7 | 297 |
| 139 | 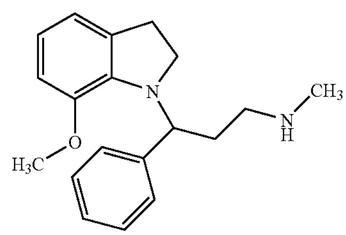 | [3-(7-Methoxy-2,3-dihydro-indol-1-yl)-3-phenyl-propyl]-methyl-amine | 7 | 297 |
| 140 | 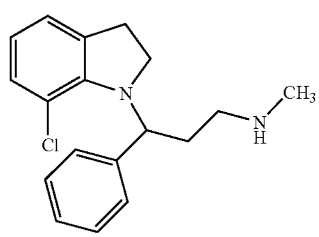 | [3-(7-Chloro-2,3-dihydro-indol-1-yl)-3-phenyl-propyl]-methyl-amine | 7 | 302 |
| 141 | 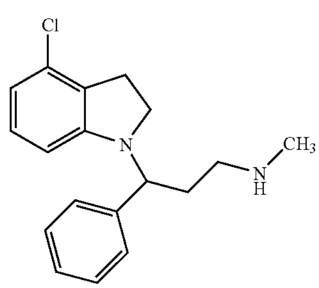 | [3-(4-Chloro-2,3-dihydro-indol-1-yl)-3-phenyl-propyl]-methyl-amine | 7 | 302 |
| 142 | 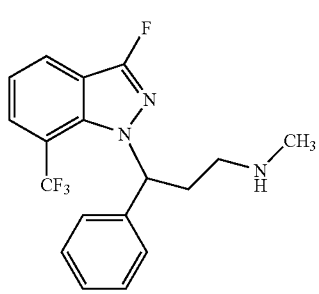 | [3-(3-Fluoro-7-trifluoromethyl-indazol-1-yl)-3-phenyl-propyl]-methyl-amine | 11 | 298 |

TABLE 1-continued

| # | Structure | Name | Example | MP or M + H |
|---|---|---|---|---|
| 143 | 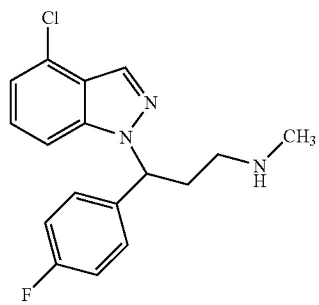 | [3-(4-Chloro-indazol-1-yl)-3-(4-fluoro-phenyl)-propyl]-methyl-amine | 11 | 319 |
| 144 | 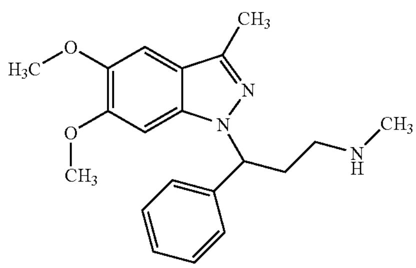 | [3-(5,6-Dimethoxy-3-methyl-indazol-1-yl)-3-phenyl-propyl]-methyl-amine | 11 | 340 |
| 145 | 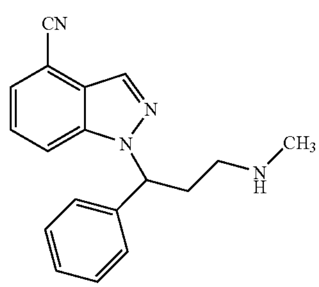 | 1-(3-Methylamino-1-phenyl-propyl)-1H-indazole-4-carbonitrile | 11 | 291 |
| 146 | 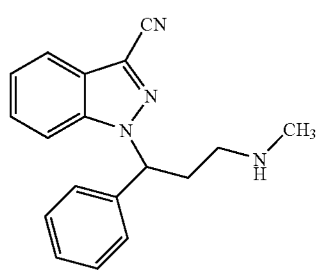 | 1-(3-Methylamino-1-phenyl-propyl)-1H-indazole-3-carbonitrile | 11 | 291 |
| 147 | 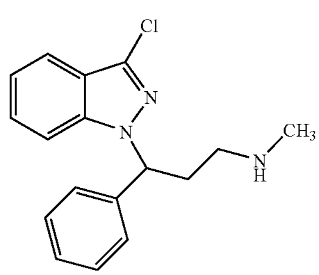 | [3-(3-Chloro-indazol-1-yl)-3-phenyl-propyl]-methyl-amine | 11 | 301 |

TABLE 1-continued
| # | Structure | Name | Example | MP or M + H |
|---|---|---|---|---|
| 148 | 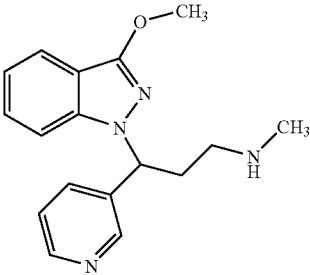 | [3-(3-Methoxy-indazol-1-yl)-3-pyridin-3-yl-propyl]-methyl-amine | 11 | 297 |
| 149 | 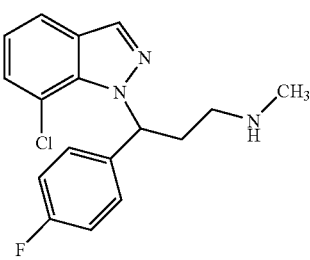 | [3-(7-Chloro-indazol-1-yl)-3-(4-fluoro-phenyl)-propyl]-methyl-amine | 11 | 319 |
| 150 | 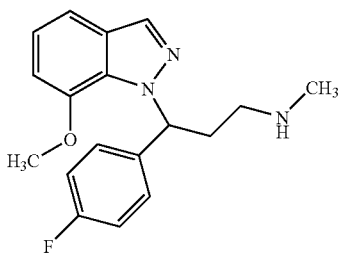 | [3-(4-Fluoro-phenyl)-3-(7-methoxy-indazol-1-yl)-propyl]-methyl-amine | 11 | 314 |
| 151 | 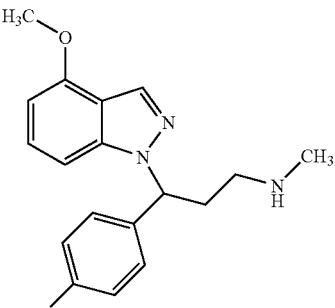 | [3-(4-Fluoro-phenyl)-3-(4-methoxy-indazol-1-yl)-propyl]-methyl-amine | 11 | 314 |
| 152 | 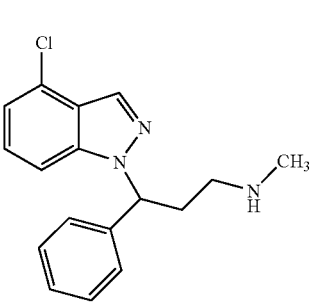 | [3-(4-Chloro-indazol-1-yl)-3-phenyl-propyl]-methyl-amine | 11 | 301 |

TABLE 1-continued

| # | Structure | Name | Example | MP or M + H |
|---|-----------|------|---------|-------------|
| 153 | 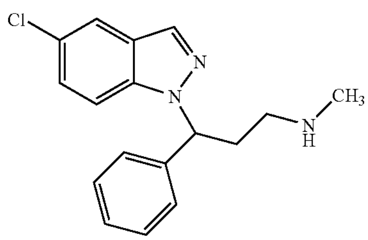 | [3-(5-Chloro-indazol-1-yl)-3-phenyl-propyl]-methyl-amine | 11 | 301 |
| 154 | 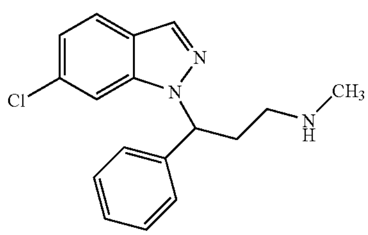 | [3-(6-Chloro-indazol-1-yl)-3-phenyl-propyl]-methyl-amine | 11 | 301 |
| 155 | 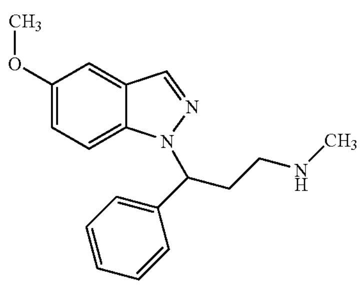 | [3-(5-Methoxy-indazol-1-yl)-3-phenyl-propyl]-methyl-amine | 11 | 296 |
| 156 | 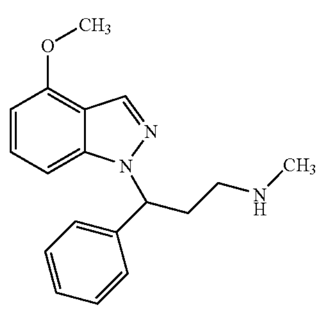 | [3-(4-Methoxy-indazol-1-yl)-3-phenyl-propyl]-methyl-amine | 11 | 296 |
| 157 | 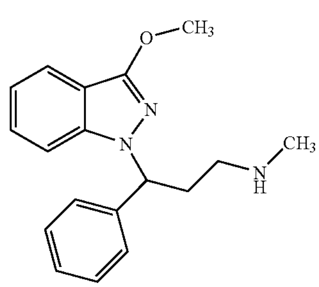 | [3-(3-Methoxy-indazol-1-yl)-3-phenyl-propyl]-methyl-amine | 11 | 296 |
| 158 | 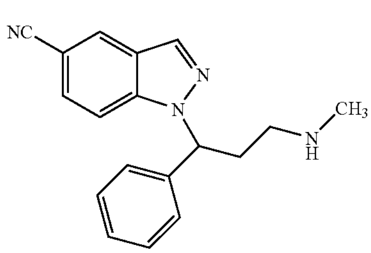 | 1-(3-Methylamino-1-phenyl-propyl)-1H-indazole-5-carbonitrile | 11 | 291 |

TABLE 1-continued

| # | Structure | Name | Example | MP or M + H |
|---|---|---|---|---|
| 159 | 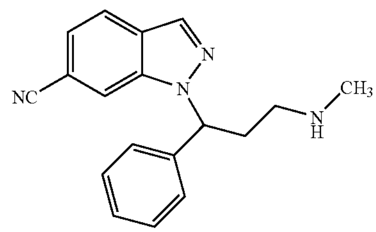 | 1-(3-Methylamino-1-phenyl-propyl)-1H-indazole-6-carbonitrile | 11 | 291 |
| 160 | 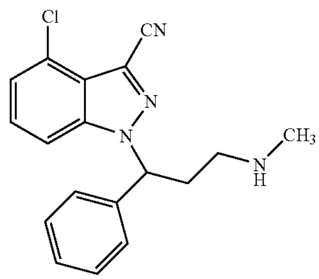 | 4-Chloro-1-(3-methylamino-1-phenyl-propyl)-1H-indole-3-carbonitrile | 12 | 325 |
| 161 | 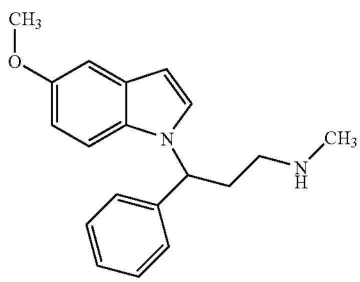 | [3-(5-Methoxy-indol-1-yl)-3-phenyl-propyl]-methyl-amine | 12 | 295 |
| 162 | 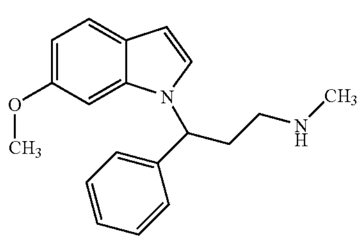 | [3-(6-Methoxy-indol-1-yl)-3-phenyl-propyl]-methyl-amine | 12 | 295 |
| 163 | 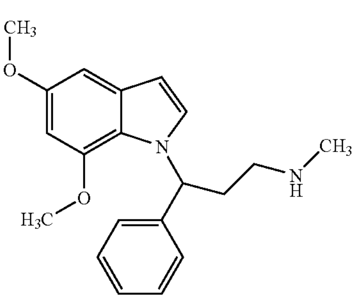 | [3-(5,7-Dimethoxy-indol-1-yl)-3-phenyl-propyl]-methyl-amine | 12 | 325 |

TABLE 1-continued

| # | Structure | Name | Example | MP or M + H |
|---|---|---|---|---|
| 164 | 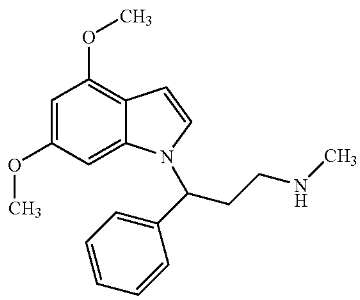 | [3-(4,6-Dimethoxy-indol-1-yl)-3-phenyl-propyl]-methyl-amine | 12 | 325 |
| 165 | 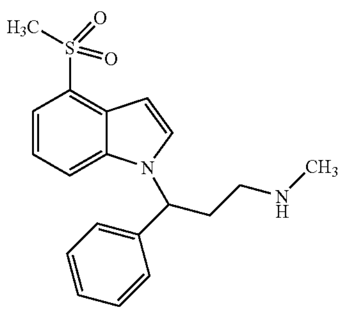 | [3-(4-Methanesulfonyl-indol-1-yl)-3-phenyl-propyl]-methyl-amine | 12 | 343 |
| 166 | 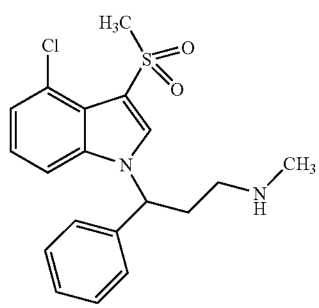 | [3-(4-Chloro-3-methanesulfonyl-indol-1-yl)-3-phenyl-propyl]-methyl-amine | 12 | 378 |
| 167 | 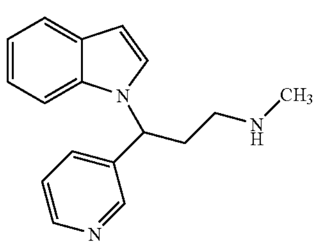 | (3-Indol-1-yl-3-pyridin-3-yl-propyl)-methyl-amine | 12 | 266 |
| 168 | 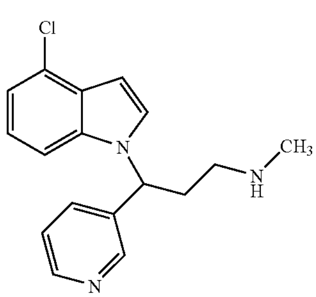 | [3-(4-Chloro-indol-1-yl)-3-pyridin-3-yl-propyl]-methyl-amine | 12 | 301 |

TABLE 1-continued

| # | Structure | Name | Example | MP or M + H |
|---|-----------|------|---------|-------------|
| 169 | 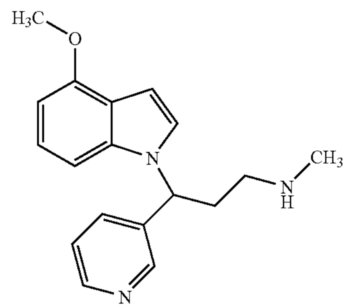 | [3-(4-Methoxy-indol-1-yl)-3-pyridin-3-yl-propyl]-methyl-amine | 12 | 296 |
| 170 | 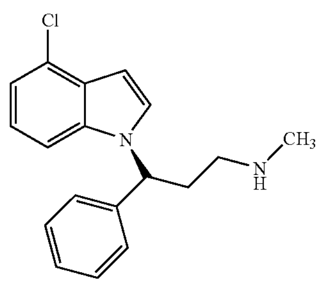 | (S)-[3-(4-Chloro-indol-1-yl)-3-phenyl-propyl]-methyl-amine | 12 | 300 |
| 171 | 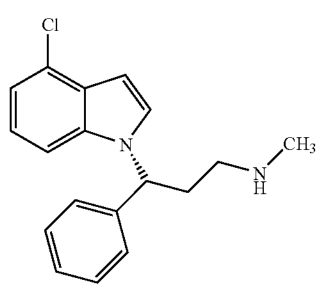 | (R)-[3-(4-Chloro-indol-1-yl)-3-phenyl-propyl]-methyl-amine | 12 | 300 |
| 172 | 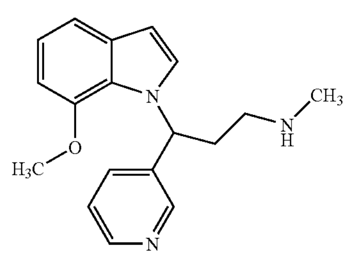 | [3-(7-Methoxy-indol-1-yl)-3-pyridin-3-yl-propyl]-methyl-amine | 12 | 296 |
| 173 | 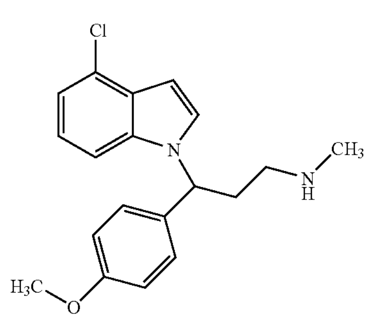 | [3-(4-Chloro-indol-1-yl)-3-(4-methoxy-phenyl)-propyl]-methyl-amine | 12 | 330 |

TABLE 1-continued

| # | Structure | Name | Example | MP or M + H |
|---|-----------|------|---------|-------------|
| 174 | 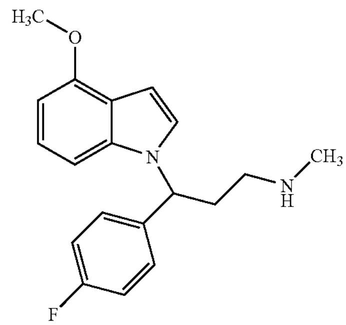 | [3-(4-Fluoro-phenyl)-3-(4-methoxy-indol-1-yl)-propyl]-methyl-amine | 12 | 313 |
| 175 | 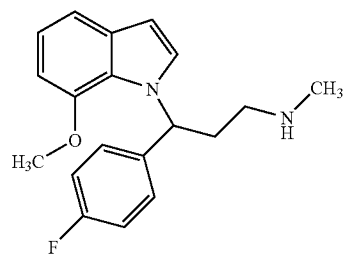 | [3-(4-Fluoro-phenyl)-3-(7-methoxy-indol-1-yl)-propyl]-methyl-amine | 12 | 313 |
| 176 | 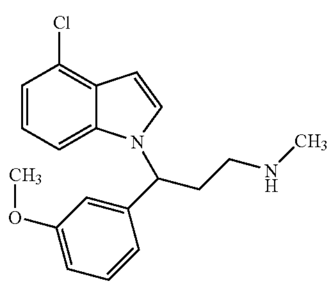 | [3-(4-Chloro-indol-1-yl)-3-(3-methoxy-phenyl)-propyl]-methyl-amine | 12 | 330 |
| 177 | 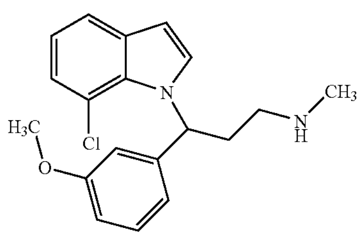 | [3-(7-Chloro-indol-1-yl)-3-(3-methoxy-phenyl)-propyl]-methyl-amine | 12 | 330 |
| 178 | 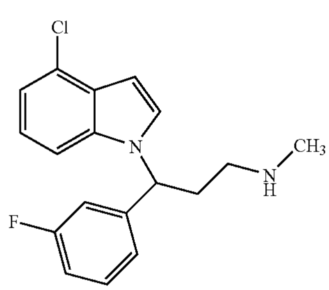 | [3-(4-Chloro-indol-1-yl)-3-(3-fluoro-phenyl)-propyl]-methyl-amine | 12 | 318 |

TABLE 1-continued

| # | Structure | Name | Example | MP or M + H |
|---|---|---|---|---|
| 179 | 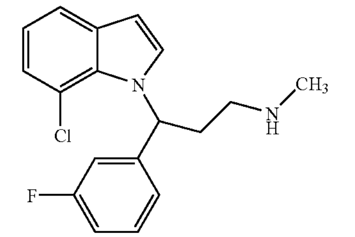 | [3-(7-Chloro-indol-1-yl)-3-(3-fluoro-phenyl)-propyl]-methyl-amine | 12 | 318 |
| 180 | 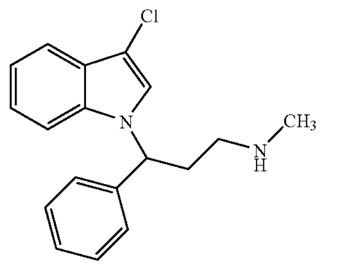 | [3-(3-Chloro-indol-1-yl)-3-phenyl-propyl]-methyl-amine | 12 | 300 |
| 181 | 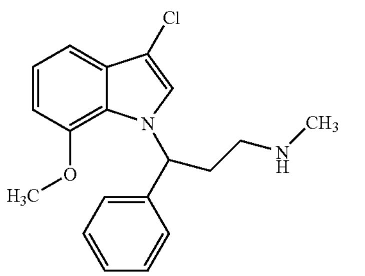 | [3-(3-Chloro-7-methoxy-indol-1-yl)-3-phenyl-propyl]-methyl-amine | 12 | 330 |
| 182 | 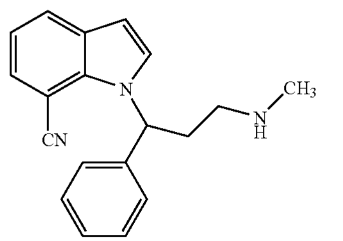 | 1-(3-Methylamino-1-phenyl-propyl)-1H-indole-7-carbonitrile | 12 | 299 |
| 183 | 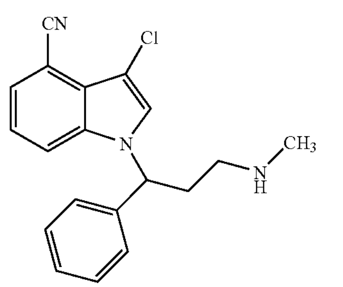 | 3-Chloro-1-(3-methylamino-1-phenyl-propyl)-1H-indole-4-carbonitrile | 12 | 325 |
| 184 | 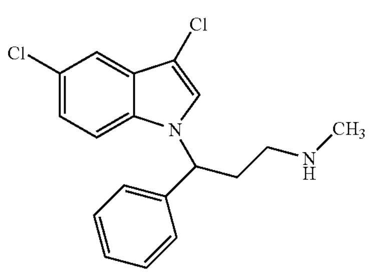 | [3-(3,5-Dichloro-indol-1-yl)-3-phenyl-propyl]-methyl-amine | 12 | 334 |

TABLE 1-continued

| # | Structure | Name | Example | MP or M + H |
|---|---|---|---|---|
| 185 | 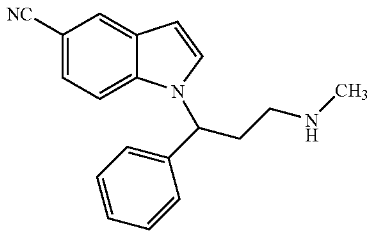 | 1-(3-Methylamino-1-phenyl-propyl)-1H-indole-5-carbonitrile | 12 | 299 |
| 186 | 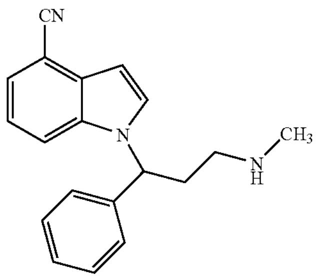 | 1-(3-Methylamino-1-phenyl-propyl)-1H-indole-4-carbonitrile | 12 | 299 |
| 187 | 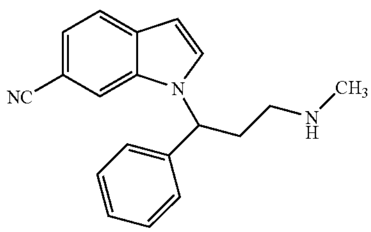 | 1-(3-Methylamino-1-phenyl-propyl)-1H-indole-6-carbonitrile | 12 | 299 |
| 188 | 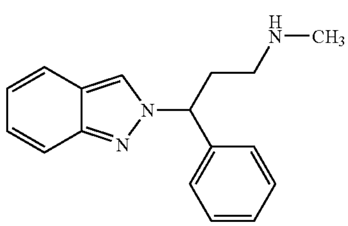 | (3-Indazol-2-yl-3-phenyl-propyl)-methyl-amine | 8 | 266 |
| 189 | 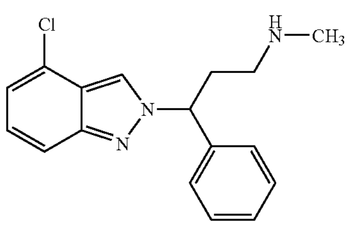 | [3-(4-Chloro-indazol-2-yl)-3-phenyl-propyl]-methyl-amine | 8 | 301 |
| 190 | 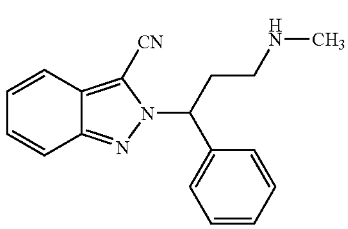 | 2-(3-Methylamino-1-phenyl-propyl)-2H-indazole-4-carbonitrile | 8 | 291 |

TABLE 1-continued

| # | Structure | Name | Example | MP or M + H |
|---|---|---|---|---|
| 191 | 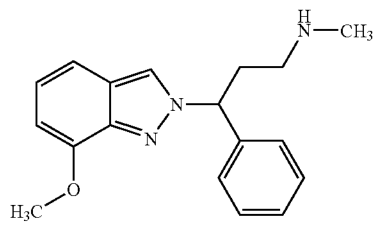 | 2-(3-Methylamino-1-phenyl-propyl)-2H-indazole-3-carbonitrile | 8 | 291 |
| 192 | 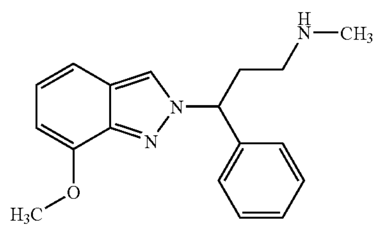 | [3-(7-Methoxy-indazol-2-yl)-3-phenyl-propyl]-methyl-amine | 8 | 296 |
| 193 | 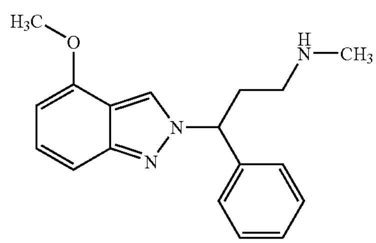 | [3-(4-Methoxy-indazol-2-yl)-3-phenyl-propyl]-methyl-amine | 8 | 296 |
| 194 | 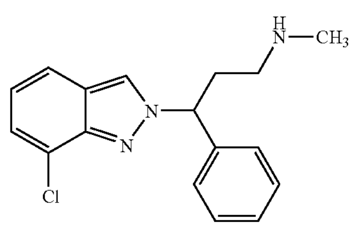 | [3-(7-Chloro-indazol-2-yl)-3-phenyl-propyl]-methyl-amine | 8 | 301 |
| 195 | 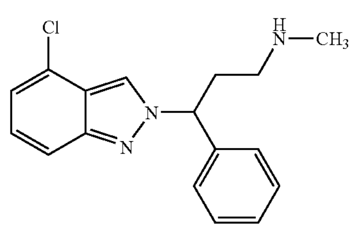 | [3-(4-Chloro-indazol-2-yl)-3-phenyl-propyl]-methyl-amine | 8 | 301 |
| 196 | 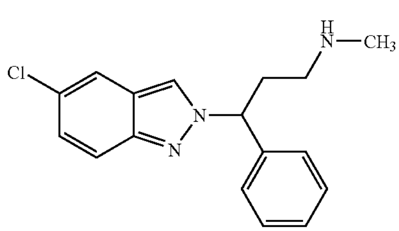 | [3-(5-Chloro-indazol-2-yl)-3-phenyl-propyl]-methyl-amine | 8 | 301 |

TABLE 1-continued

| # | Structure | Name | Example | MP or M + H |
|---|-----------|------|---------|-------------|
| 197 | 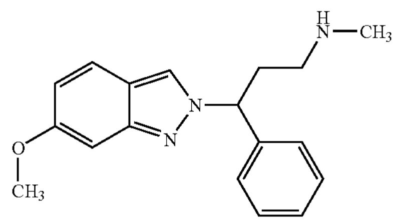 | [3-(6-Methoxy-indazol-2-yl)-3-phenyl-propyl]-methyl-amine | 8 | 296 |
| 198 | 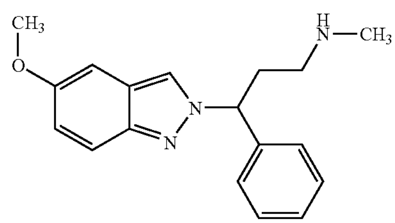 | [3-(5-Methoxy-indazol-2-yl)-3-phenyl-propyl]-methyl-amine | 8 | 301 |
| 199 | 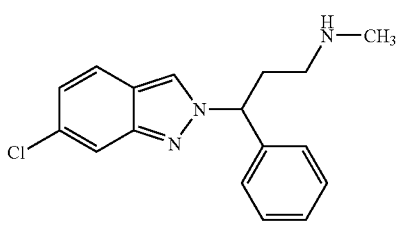 | [3-(6-Chloro-indazol-2-yl)-3-phenyl-propyl]-methyl-amine | 8 | 296 |
| 200 | 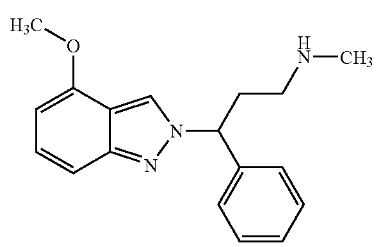 | [3-(4-Methoxy-indazol-2-yl)-3-phenyl-propyl]-methyl-amine | 8 | 301 |
| 201 | 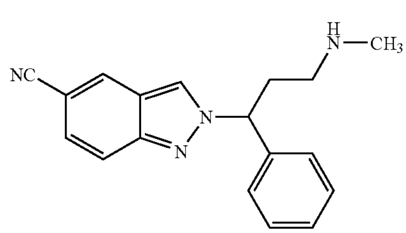 | 2-(3-Methylamino-1-phenyl-propyl)-2H-indazole-5-carbonitrile | 8 | 291 |
| 202 | 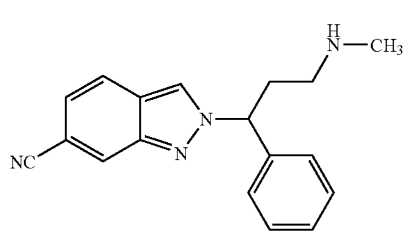 | 2-(3-Methylamino-1-phenyl-propyl)-2H-indazole-6-carbonitrile | 8 | 291 |

TABLE 1-continued

| # | Structure | Name | Example | MP or M + H |
|---|---|---|---|---|
| 203 | 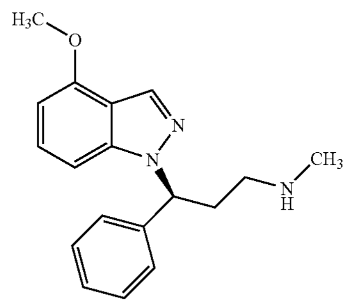 | (S)-[3-(4-Methoxy-indazol-1-yl)-3-phenyl-propyl]-methyl-amine | 11 | 296 |
| 204 | 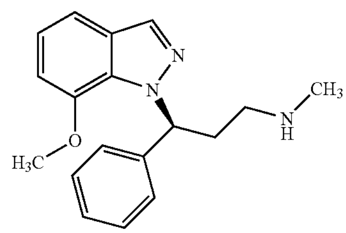 | (S)-[3-(7-Methoxy-indazol-1-yl)-3-phenyl-propyl]-methyl-amine | 11 | 296 |
| 205 | 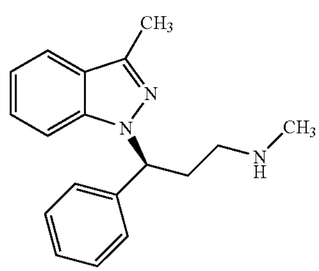 | (S)-Methyl-[3-(3-methyl-indazol-1-yl)-3-phenyl-propyl]-amine | 11 | 280 |
| 206 | 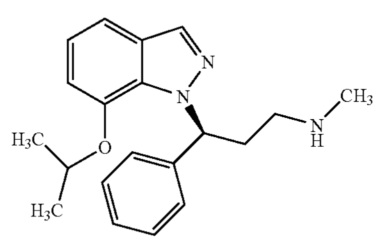 | (S)-[3-(7-Isopropoxy-indazol-1-yl)-3-phenyl-propyl]-methyl-amine | 11 | 324 |
| 207 | 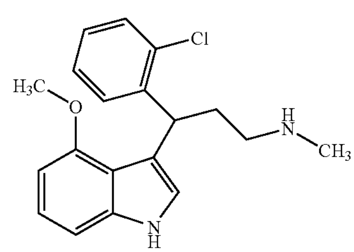 | [3-(2-Chloro-phenyl)-3-(4-methoxy-1H-indol-3-yl)-propyl]-methyl-amine | 1 | 330 |

TABLE 1-continued

| # | Structure | Name | Example | MP or M + H |
|---|---|---|---|---|
| 208 | 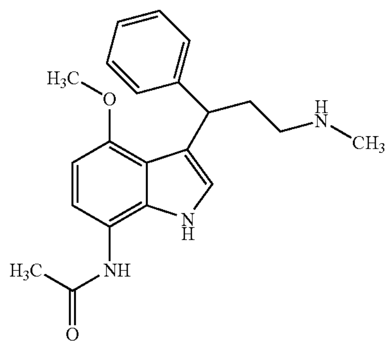 | N-[4-Methoxy-3-(3-methylamino-1-phenyl-propyl)-1H-indol-7-yl]-acetamide | 1 | 352 |
| 209 | 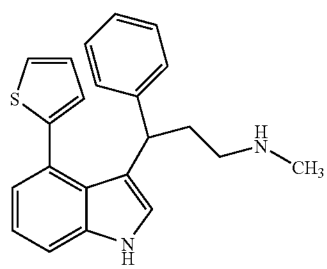 | Methyl-[3-phenyl-3-(4-thiophen-2-yl-1H-indol-3-yl)-propyl]-amine | 1 | 347 |
| 210 | 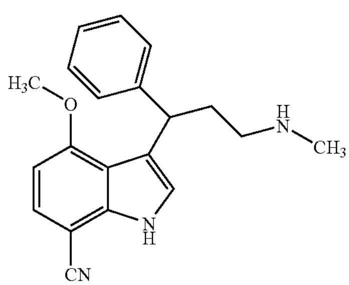 | 4-Methoxy-3-(3-methylamino-1-phenyl-propyl)-1H-indole-7-carbonitrile | 1 | 320 |
| 211 | 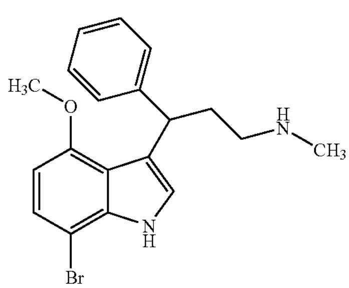 | [3-(7-Bromo-4-methoxy-1H-indol-3-yl)-3-phenyl-propyl]-methyl-amine | 1 | 374 |
| 212 | 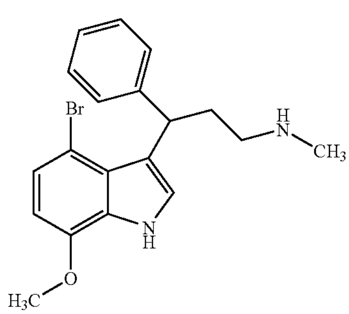 | [3-(4-Bromo-7-methoxy-1H-indol-3-yl)-3-phenyl-propyl]-methyl-amine | 1 | 374 |

TABLE 1-continued

| # | Structure | Name | Example | MP or M + H |
|---|---|---|---|---|
| 213 | 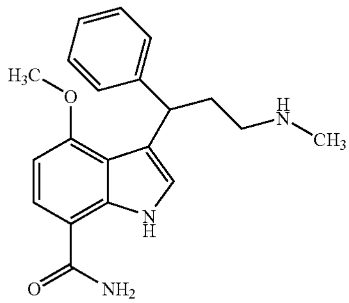 | 4-Methoxy-3-(3-methylamino-1-phenyl-propyl)-1H-indole-7-carboxylic acid amide | 1 | 338 |
| 214 | 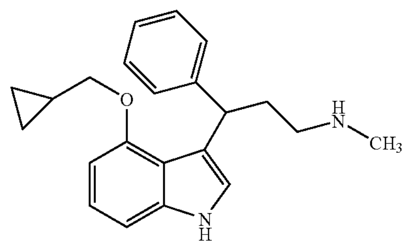 | [3-(4-Cyclopropylmethoxy-1H-indol-3-yl)-3-phenyl-propyl]-methyl-amine | 1 | 335 |
| 215 | 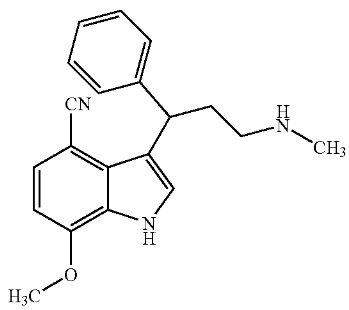 | 7-Methoxy-3-(3-methylamino-1-phenyl-propyl)-1H-indole-4-carbonitrile | 1 | 320 |
| 216 | 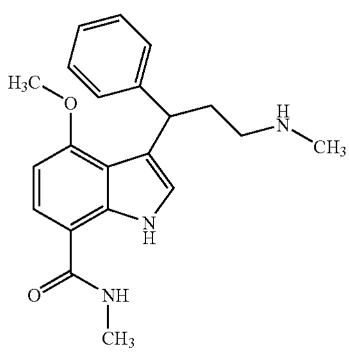 | 4-Methoxy-3-(3-methylamino-1-phenyl-propyl)-1H-indole-7-carboxylic acid methylamide | 1 | 352 |
| 217 | 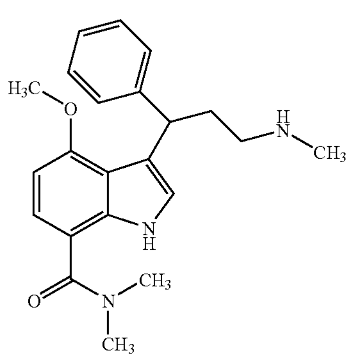 | 4-Methoxy-3-(3-methylamino-1-phenyl-propyl)-1H-indole-7-carboxylic acid dimethylamide | 1 | 366 |

TABLE 1-continued

| # | Structure | Name | Example | MP or M + H |
|---|-----------|------|---------|-------------|
| 218 | 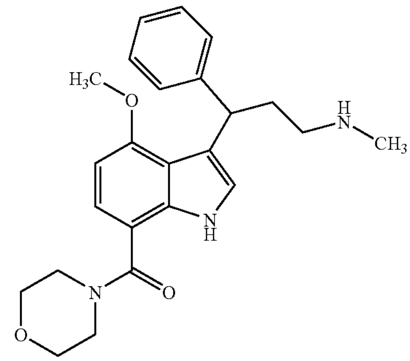 | [4-Methoxy-3-(3-methylamino-1-phenyl-propyl)-1H-indol-7-yl]-morpholin-4-yl-methanone | 1 | 409 |
| 219 | 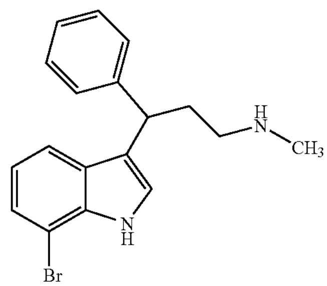 | [3-(4-Bromo-1H-indol-3-yl)-3-phenyl-propyl]-methyl-amine | 1 | 344 |
| 220 | 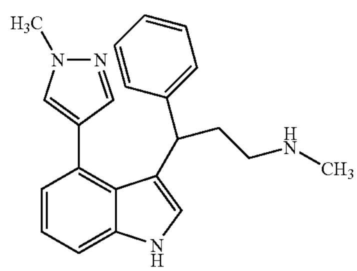 | Methyl-{3-[4-(1-methyl-1H-pyrazol-4-yl)-1H-indol-3-yl]-3-phenyl-propyl}-amine | 1 | 345 |
| 221 | 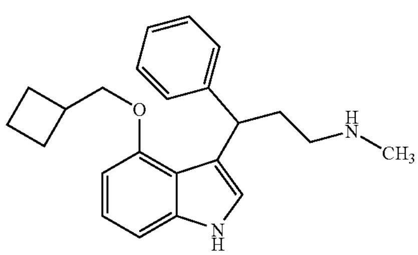 | [3-(4-Cyclobutylmethoxy-1H-indol-3-yl)-3-phenyl-propyl]-methyl-amine | 1 | 349 |
| 222 | 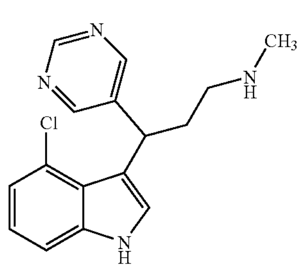 | [3-(4-Chloro-1H-indol-3-yl)-3-pyrimidin-5-yl-propyl]-methyl-amine | 1 | 302 |

TABLE 1-continued

| # | Structure | Name | Example | MP or M + H |
|---|---|---|---|---|
| 223 | 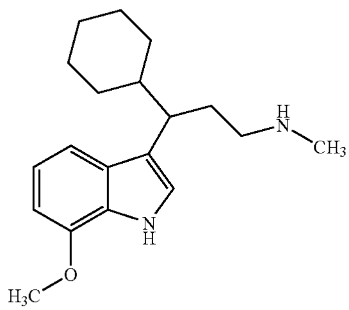 | [3-Cyclohexyl-3-(7-methoxy-1H-indol-3-yl)-propyl]-methyl-amine | 1 | 301 |
| 224 | 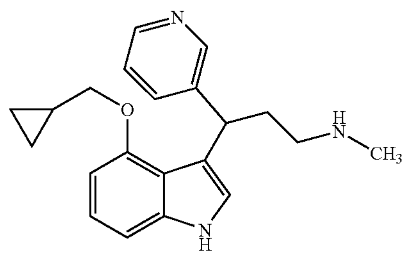 | [3-(4-Cyclopropylmethoxy-1H-indol-3-yl)-3-pyridin-3-yl-propyl]-methyl-amine | 1 | 336 |
| 225 | 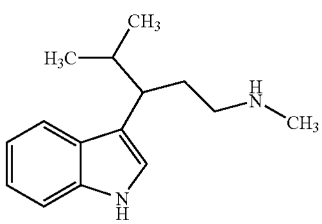 | [3-(1H-Indol-3-yl)-4-methyl-pentyl]-methyl-amine | 1 | 231 |
| 226 | 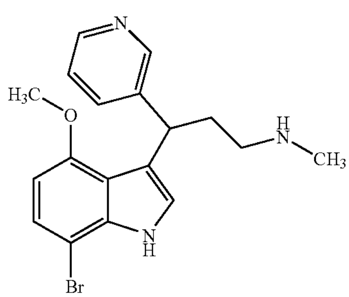 | [3-(7-Bromo-4-methoxy-1H-indol-3-yl)-3-pyridin-3-yl-propyl]-methyl-amine | 1 | 375 |
| 227 | 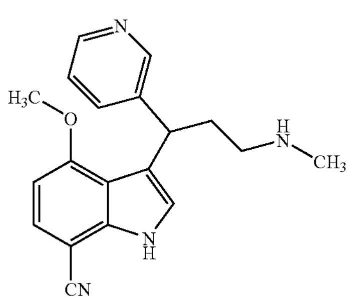 | 4-Methoxy-3-(3-methylamino-1-pyridin-3-yl-propyl)-1H-indole-7-carbonitrile | 1 | 310 |

TABLE 1-continued

| # | Structure | Name | Example | MP or M + H |
|---|---|---|---|---|
| 228 | 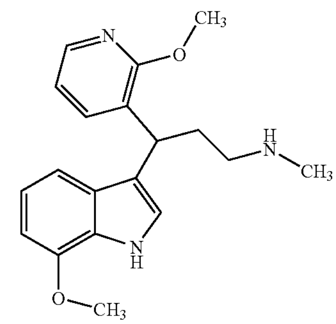 | [3-(7-Methoxy-1H-indol-3-yl)-3-(2-methoxy-pyridin-3-yl)-propyl]-methyl-amine | 1 | 326 |
| 229 | 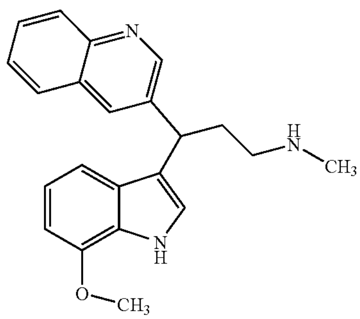 | [3-(7-Methoxy-1H-indol-3-yl)-3-quinolin-3-yl-propyl]-methyl-amine | 1 | 346 |
| 230 | 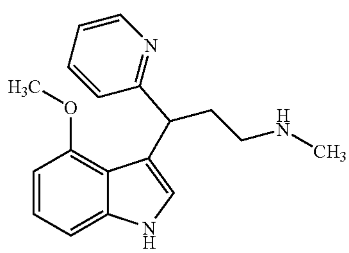 | [3-(4-Methoxy-1H-indol-3-yl)-3-pyridin-2-yl-propyl]-methyl-amine | 1 | 296 |
| 231 | 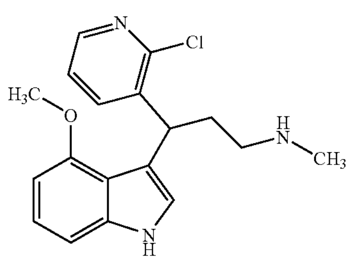 | [3-(2-Chloro-pyridin-3-yl)-3-(4-methoxy-1H-indol-3-yl)-propyl]-methyl-amine | 1 | 331 |
| 232 | 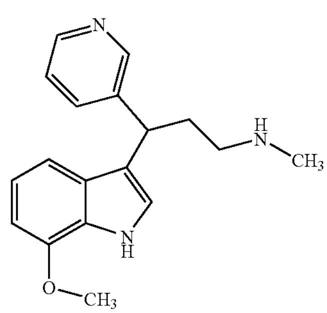 | [3-(7-Methoxy-1H-indol-3-yl)-3-pyridin-3-yl-propyl]-methyl-amine | 1 | 296 |

TABLE 1-continued

| # | Structure | Name | Example | MP or M + H |
|---|-----------|------|---------|-------------|
| 233 | 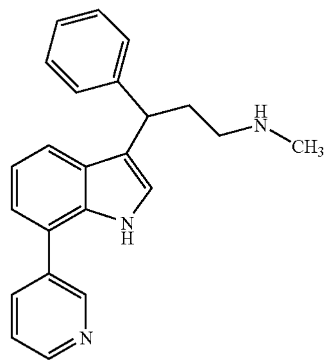 | Methyl-[3-phenyl-3-(7-pyridin-3-yl-1H-indol-3-yl)-propyl]-amine | 1 | 342 |
| 234 | 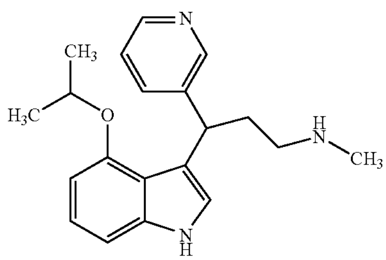 | [3-(4-Isopropoxy-1H-indol-3-yl)-3-pyridin-3-yl-propyl]-methyl-amine | 1 | 324 |
| 235 | 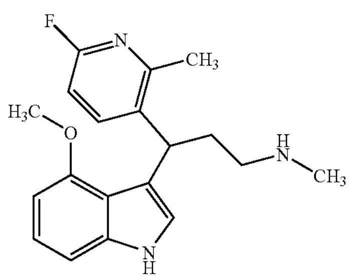 | [3-(6-Fluoro-2-methyl-pyridin-3-yl)-3-(4-methoxy-1H-indol-3-yl)-propyl]-methyl-amine | 1 | 328 |
| 236 | 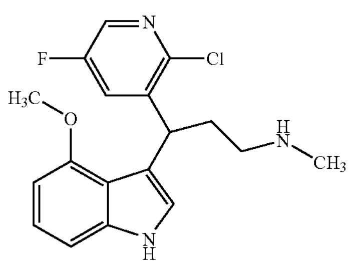 | [3-(2-Chloro-5-fluoro-pyridin-3-yl)-3-(4-methoxy-1H-indol-3-yl)-propyl]-methyl-amine | 1 | 349 |
| 237 | 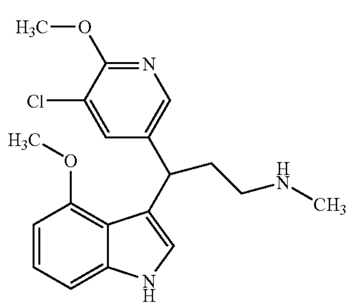 | [3-(5-Chloro-6-methoxy-pyridin-3-yl)-3-(4-methoxy-1H-indol-3-yl)-propyl]-methyl-amine | 1 | 360 |

TABLE 1-continued

| # | Structure | Name | Example | MP or M + H |
|---|---|---|---|---|
| 238 | 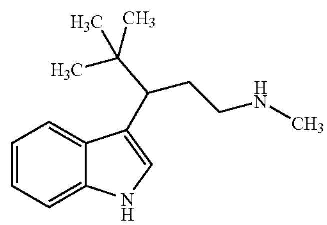 | [3-(1H-Indol-3-yl)-4,4-dimethyl-pentyl]-methyl-amine | 10 | 245 |
| 239 | 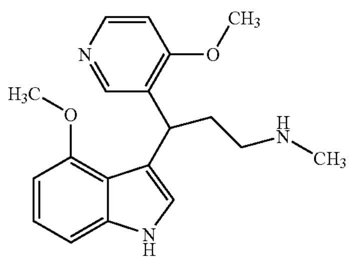 | [3-(4-Methoxy-1H-indol-3-yl)-3-(4-methoxy-pyridin-3-yl)-propyl]-methyl-amine | 1 | 326 |
| 240 | 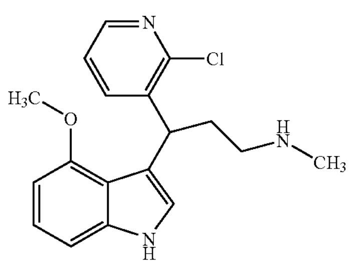 | [3-(2-Chloro-pyridin-3-yl)-3-(4-methoxy-1H-indol-3-yl)-propyl]-methyl-amine | 1 | 331 |
| 241 | 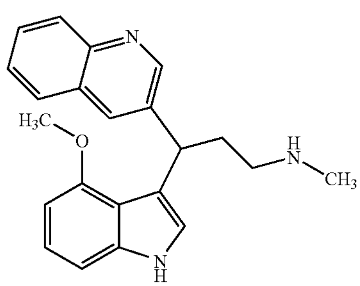 | [3-(4-Methoxy-1H-indol-3-yl)-3-quinolin-3-yl-propyl]-methyl-amine | 1 | 345 |
| 242 | 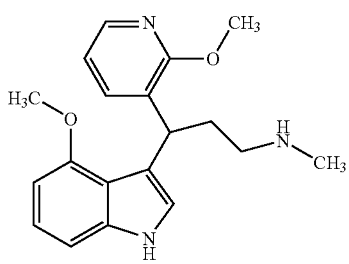 | [3-(4-Methoxy-1H-indol-3-yl)-3-(2-methoxy-pyridin-3-yl)-propyl]-methyl-amine | 1 | 326 |

TABLE 1-continued

| # | Structure | Name | Example | MP or M + H |
|---|---|---|---|---|
| 243 | 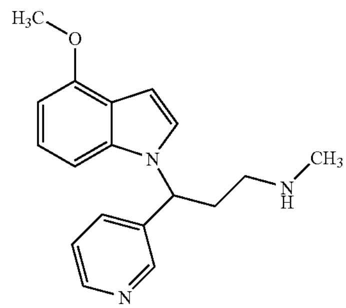 | [3-(4-Methoxy-indol-1-yl)-3-pyridin-3-yl-propyl]-methyl-amine | 13 | 296 |
| 244 | 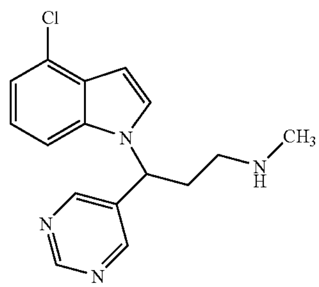 | [3-(4-Chloro-indol-1-yl)-3-pyrimidin-5-yl-propyl]-methyl-amine | 12 | 302 |
| 245 | 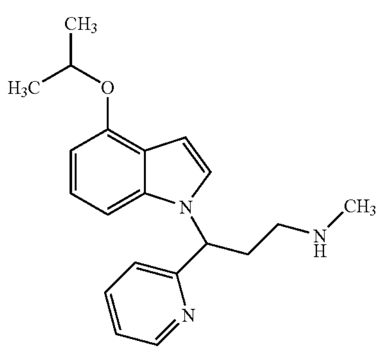 | [3-(4-Isopropoxy-indol-1-yl)-3-pyridin-2-yl-propyl]-methyl-amine | 13 | 324 |
| 246 | 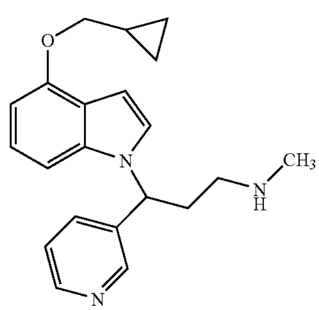 | [3-(4-Cyclopropylmethoxy-indol-1-yl)-3-pyridin-3-yl-propyl]-methyl-amine | 13 | 336 |
| 247 | 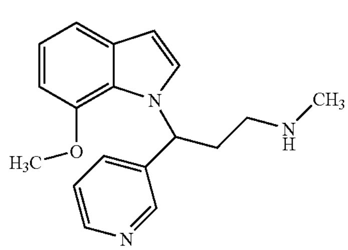 | [3-(7-Methoxy-indol-1-yl)-3-pyridin-3-yl-propyl]-methyl-amine | 13 | 296 |

TABLE 1-continued
| # | Structure | Name | Example | MP or M + H |
|---|---|---|---|---|
| 248 | 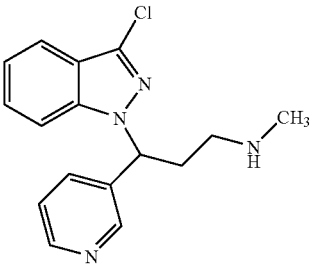 | [3-(3-Chloro-indazol-1-yl)-3-pyridin-3-yl-propyl]-methyl-amine | 13 | 302 |
| 249 | 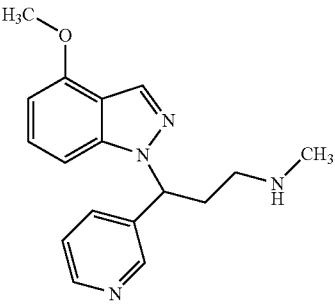 | [3-(4-Methoxy-indazol-1-yl)-3-pyridin-3-yl-propyl]-methyl-amine | 13 | 297 |
| 250 | 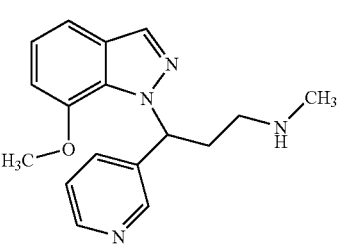 | [3-(7-Methoxy-indazol-1-yl)-3-pyridin-3-yl-propyl]-methyl-amine | 13 | 297 |
| 251 | 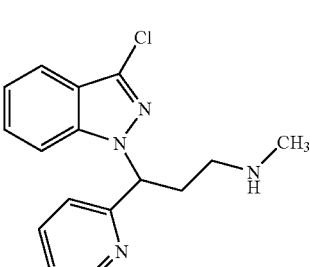 | [3-(3-Chloro-indazol-1-yl)-3-pyridin-2-1-propyl]-methyl-amine | 13 | 302 |
| 252 | 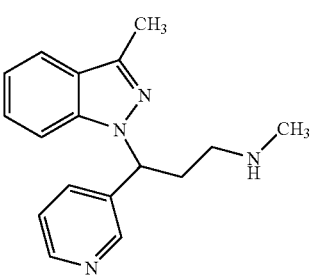 | Methyl-[3-(3-methyl-indazol-1-yl)-3-pyridin-3-yl-propyl]-amine | 13 | 281 |

TABLE 1-continued

| # | Structure | Name | Example | MP or M + H |
|---|-----------|------|---------|-------------|
| 253 | 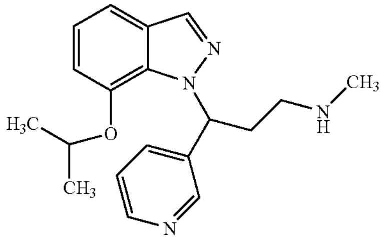 | [3-(7-Isopropoxy-indazol-1-yl)-3-pyridin-3-yl-propyl]-methyl-amine | 13 | 325 |
| 254 | 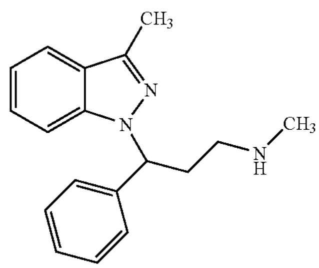 | Methyl-[3-(3-methyl-indazol-1-yl)-3-phenyl-propyl]-amine | 11 | 281 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein m, $R^1$, $R^2$, $R^3$, $R^4$, $R^5$ and $R^6$ are as defined herein.

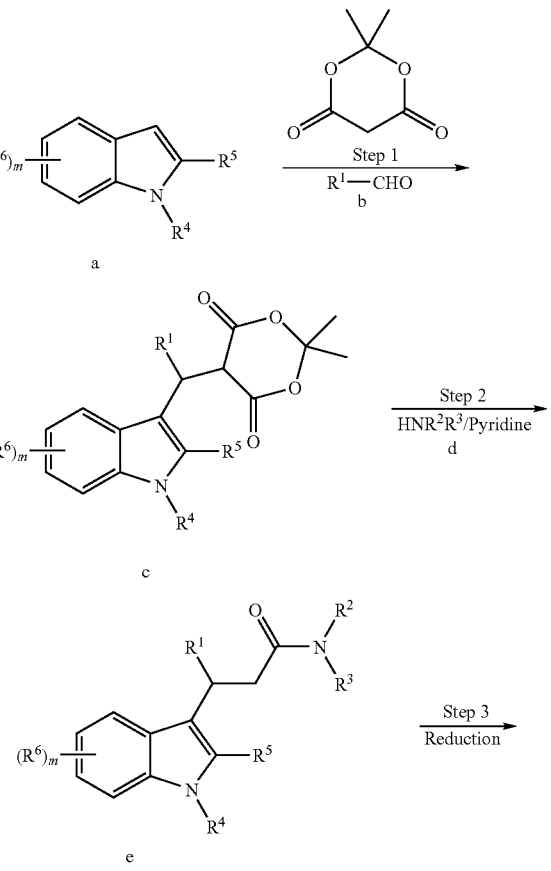

SCHEME A

-continued

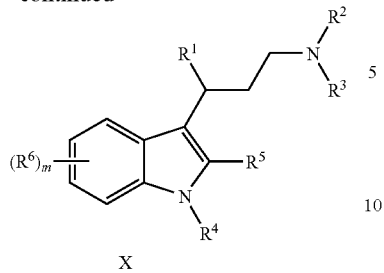

X

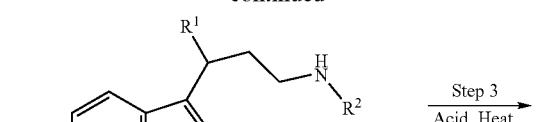

i

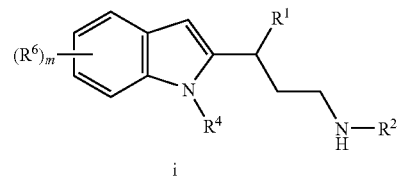

j

In Step 1 of Scheme A, indole a is treated with 2,2-dimethyl-[1,3]dioxane-4,6-dione and an aldehyde b, using the procedure of Tetrahedron 56 (2000) 5479-5492, to provide dione compound c. Aldehyde b may comprise, for example, an aryl aldehyde such as benzaldehyde or naphthaldehyde, a heteroaryl aldehyde such as a thiophene carbaldehyde, pyridine carbaldehyde, furan carbaldehyde, a cycloalkyl carbaldehyde such as cyclohexanecarbaldehyde, a branched $C_4$-$C_7$-alkyl carbaldehyde, or the like, each of which may be optionally substituted as defined herein. Numerous substituted aryl, heteroaryl, and cycloalkyl aldehydes b are commercially available or are readily prepared by techniques well known to those skilled in the art.

In step 2, the dione compound c is reacted with an amine d in the presence of pyridine or other catalytic amine to afford an indole propionamide compound e. Amine d may comprise, for example, a monoalkyl amine, a dialkyl amine, or a cyclic amine. Exemplary amines of this sort include ammonia, methylamine, ethylamine, isopropylamine, aniline, benzylamine, phenylethylamine, cyclopropylamine, dimethylamine, aziridine, pyrrolidine, piperidine and piperazine.

Reduction of propionamide compound e in step 3 provides a 3-aminopropyl indole compound of formula X in accordance with the invention. This reduction may be achieved using lithium aluminum hydride, borane or borane complex, or other strong reducing agent.

Scheme B below illustrates another synthetic procedure that may be used in preparation of compounds of the invention, wherein m, $R^1$, $R^2$, $R^3$, $R^4$, $R^5$ and $R^6$ are as defined herein.

In step 1 of Scheme B, a 3-amino-propanol compound f is treated with trifluoroacetic anhydride to afford a trifluoroacetylated propyl compound g. In step 2, the trifluoroacetylated compound g, is then heated in the presence of indole h, and the resulting residue treated with base such as sodium hydroxide to provide a 3-aminopropyl indole compound i. Compound i is a compound of formula X in accordance with the invention, wherein $R^3$ is hydrogen.

A third step may then be carried out, wherein thermal rearrangement of compound i in the presence of strong acid such as polyphosphoric acid, using the procedure of Kost et al. (1975), Moskovskogo Universiteta, Seria 2: Khimia, 16(4), 467-71, provides a compound j. Compound j is a 2-aminopropyl indole compound of formula XI in accordance with the invention, wherein $R^3$ is hydrogen.

Scheme C below illustrates another synthetic procedure usable to prepare specific compounds of the invention, wherein m, $R^1$, $R^2$, $R^3$, $R^4$, $R^5$ and $R^6$ are as defined herein.

SCHEME B

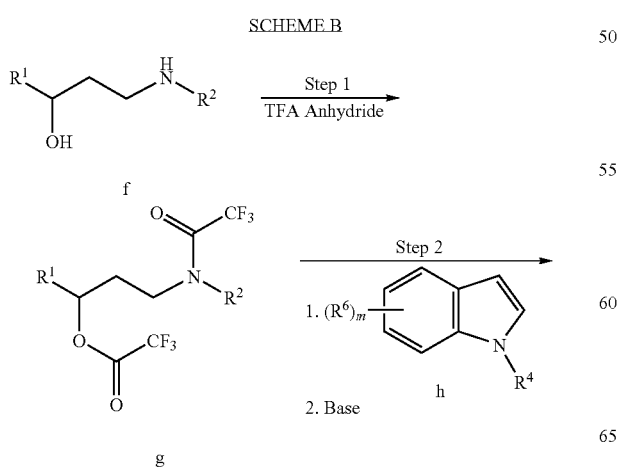

SCHEME C

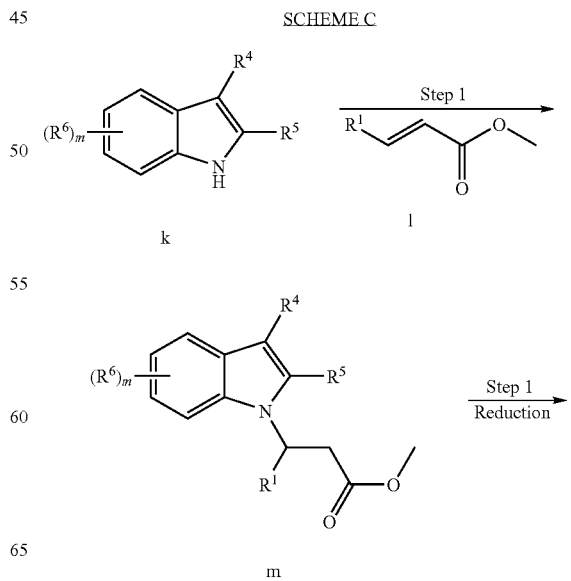

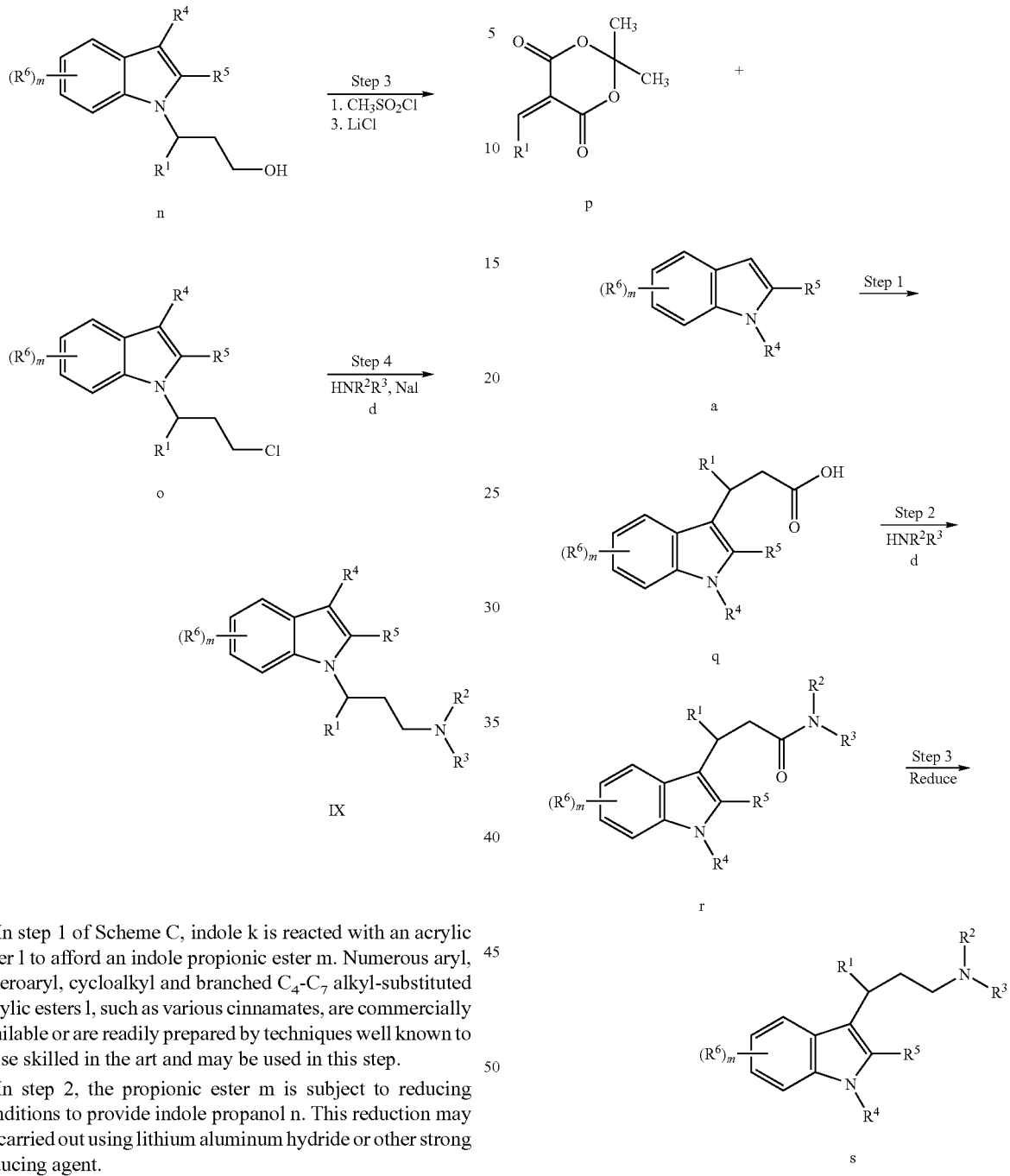

SCHEME D

In step 1 of Scheme C, indole k is reacted with an acrylic ester l to afford an indole propionic ester m. Numerous aryl, heteroaryl, cycloalkyl and branched $C_4$-$C_7$ alkyl-substituted acrylic esters l, such as various cinnamates, are commercially available or are readily prepared by techniques well known to those skilled in the art and may be used in this step.

In step 2, the propionic ester m is subject to reducing conditions to provide indole propanol n. This reduction may be carried out using lithium aluminum hydride or other strong reducing agent.

The indole propanol n is treated with methane sulfonyl chloride in step 3, followed by lithium chloride, to provide indole propyl chloride o. Thionyl chloride, acyl chloride, or other chloride source may alternatively be used in this step.

In step 4, indole propyl chloride is reacted with amine d to yield a 3-aminopropyl indole compound of formula IX in accordance with the invention. Various amines may be used in this step as noted above in regard to Scheme A.

In Scheme D another synthetic route to the compounds of the invention is illustrated, wherein m, $R^1$, $R^2$, $R^3$, $R^4$, $R^5$ and $R^6$ are as defined herein.

In Step 1 of Scheme D, substituted alkylidine Meldrum's acid compound p is reacted with indole a to afford indole acid q. Indole acid q is treated with amine d in Step 2 to form indole amide r. In Step 3, indole amide r is reduced to yield aminopropyl indole compound s, which is a compound of formula I in accordance with the invention.

Scheme E shows another procedure for preparation of the subject compounds wherein X and Y are leaving group and may be the same or different, and m, $R^1$, $R^2$, $R^3$, $R^4$, $R^5$, and $R^6$ are as defined herein.

SCHEME E

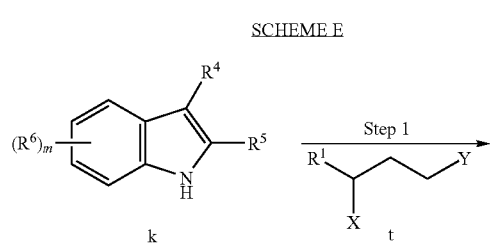

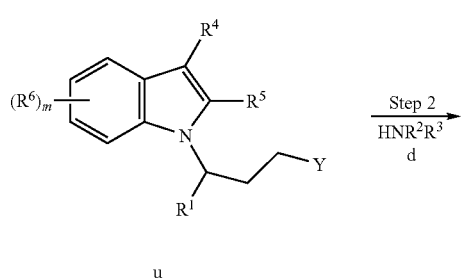

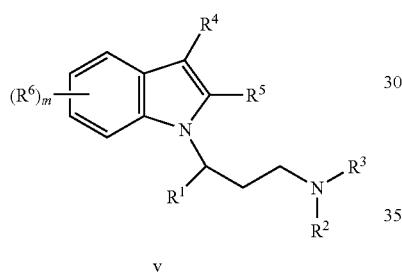

In step 1 of Scheme E, indole k is reacted with alkylating agent t to afford N-alkylated indole u. Compound u is then treated with amine d to yield aminopropyl indole v, which is a compound of formula I in accordance with the invention.

Another route to the compounds of the invention is shown in Scheme F, wherein m, $R^1$, $R^2$, $R^3$, $R^4$, $R^5$ and $R^6$ are as defined herein.

SCHEME F

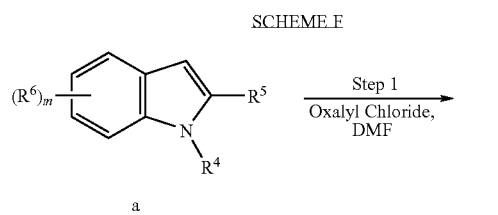

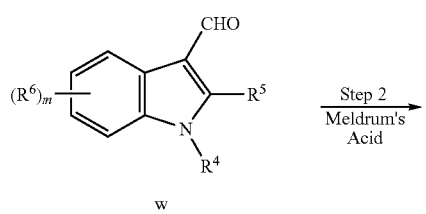

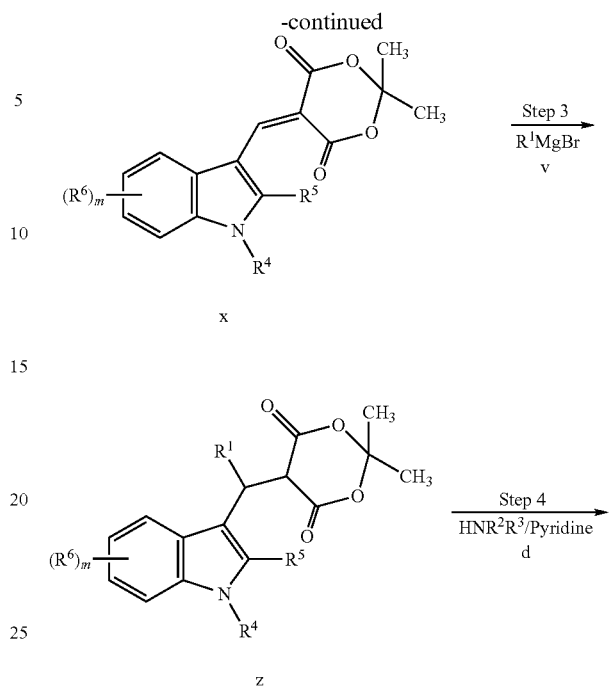

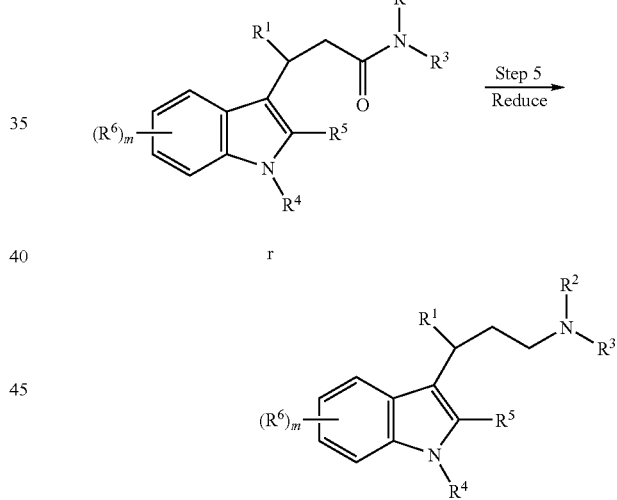

In Step 1 of Scheme F, indole compound a is treated with the Vilsmeier reagent formed by mixing oxalyl chloride with dimethyl formamide to form indole aldehyde w, which in turn is reacted with Meldrum's acid in Step 2 to yield indole compound x. Indole x is then treated with Grignard reagent y in Step 3 to afford indole compound z. In Step 4 compound z is reacted with amine d in the presence of pyridine to give indole amide r, which is then reduced in Step 5 to provide aminopropyl indole compound s. Compound s is a compound of formula I in accordance with the invention.

Scheme G illustrates yet another synthetic approach to the compounds of the invention, herein m, $R^1$, $R^2$, $R^3$, $R^4$, $R^5$ and $R^6$ are as defined herein.

SCHEME G

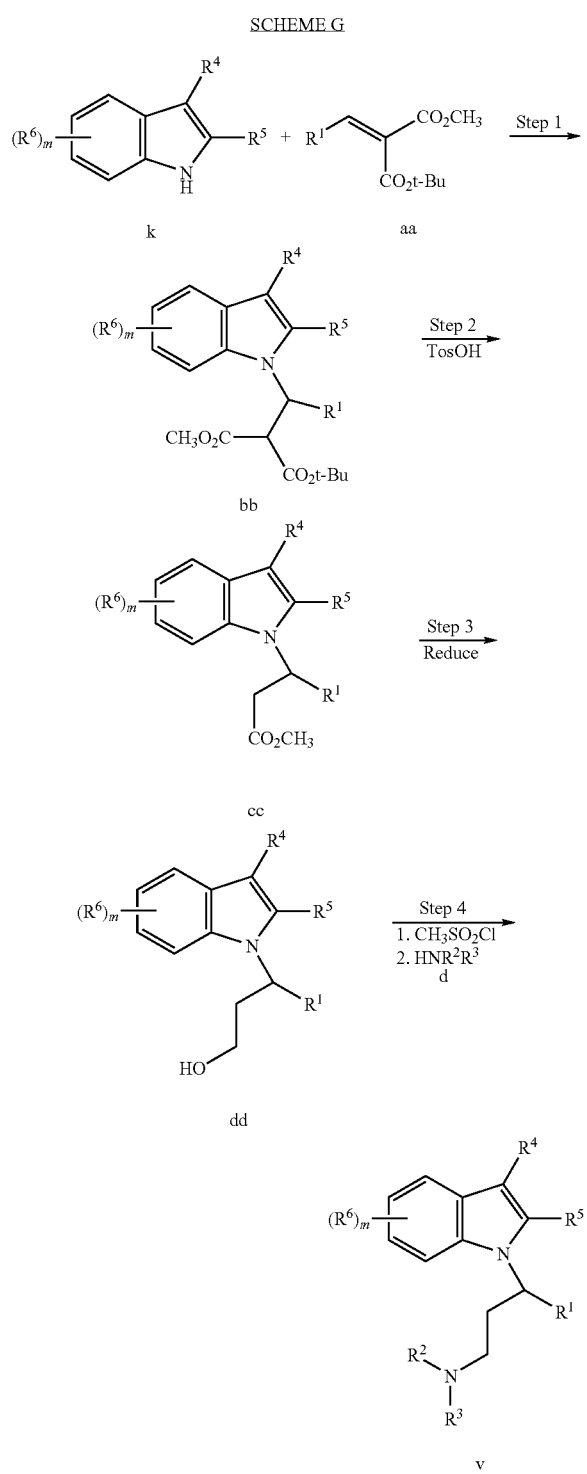

In Step 1 of Scheme G, indole k is reacted with mixed ester compound aa to form indole diester bb. Compound bb is treated with toluene sulfonic acid or like acid in Step 2 to afford indole ester compound cc. In Step 3 compound cc is reduced to give hydroxypropyl indole dd. Compound dd is then treated with methanesulfonyl chloride, followed by amine d, to afford aminopropyl indole v, which is a compound of formula I in accordance with the invention.

Numerous variations on the procedures of Schemes A through G are possible and will be readily apparent to those skilled in the art. For example, indoles a and k may be replaced by corresponding indazoles or dihydroindoles, or indole k may be replaced with the corresponding benzimidazole, to provide 3-aminopropyl indazoles or benzimidazoles in accordance with the invention. The procedure of step 3 of Scheme B may be carried out on compound X of Scheme A in embodiments where $R^3$ is hydrogen. The acrylic ester l used in step 1 is shown as a methyl ester. It should be readily apparent, however, that ethyl, isopropyl or other alkyl esters may be used in place thereof. Similarly, the methanesulfonyl chloride utilized in step 3 may be replaced with other alkyl-sulfonyl or aryl sulfonyl halides.

Specific details for producing compounds of the invention are described in the Examples section below.

Utility

The compounds of the invention are usable for the treatment of diseases or conditions associated with serotonin neurotransmission and/or norepinephrine neurotransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The compounds of the invention are also usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The compounds of the invention also possess anti-inflammatory and/or analgesic properties in vivo, and accordingly, are expected to find utility in the treatment of disease states associated with pain conditions from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Example 1

[3-(1H-Indol-3-yl)-3-phenyl-propyl]-methyl-amine

The synthetic procedure of Example 1 is outlined in Scheme H below.

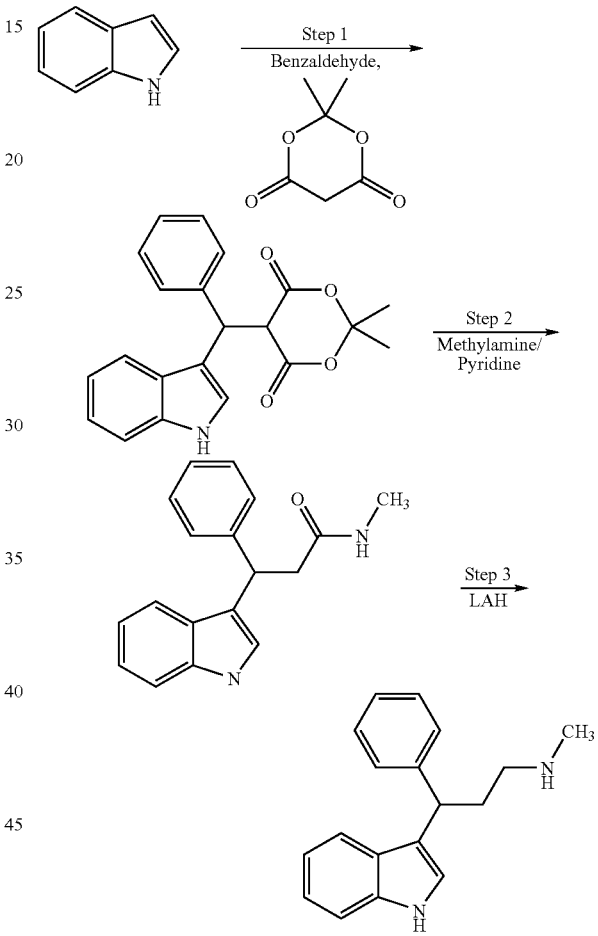

Step 1

5-[(1H-Indol-3-yl)-phenyl-methyl]-2,2-dimethyl-[1,3]dioxane-4,6-dione

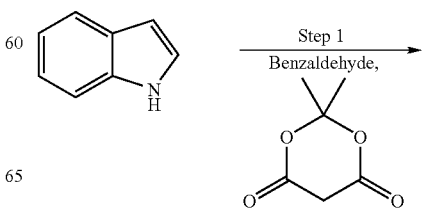

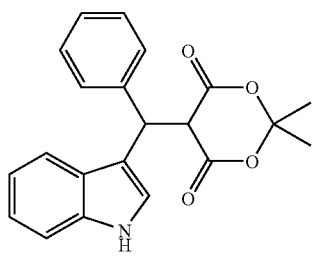

Using the procedure described in Tetrahedron 56 (2000) 5479-5492, indole (5.0 g, 42.7 mmole) and 2,2-dimethyl-[1,3]dioxane-4,6-dione (6.15 g, 42.7 mmole) were mixed in acetonitrile (50 ml). To this mixture was added benzaldehyde (9.06 g, 85.4 mmole) and d,l-proline (0.25 g). The mixture was stirred at room temperature for 18 hours after which time much of the reaction mixture had turned solid. The solvent was evaporated at reduced pressure and the residue was triturated with ether and filtered. The filter cake was washed with several portions of ether to afford pure 5-[(1H-indol-3-yl)-phenyl-methyl]-2,2-dimethyl-[1,3]dioxane-4,6-dione, 11.83 g, as a light pink solid (MS (M−H)=348) which was used without further purification in the next step.

Step 2

3-(1H-Indol-3-yl)-N-methyl-3-phenyl-propionamide

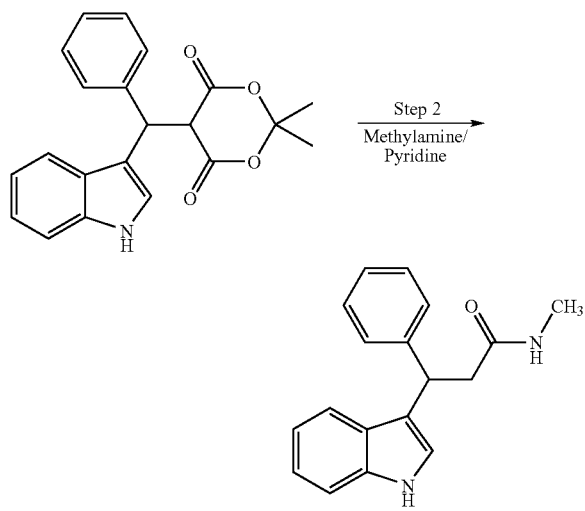

5-[(1H-Indol-3-yl)-phenyl-methyl]-2,2-dimethyl-[1,3]dioxane-4,6-dione (0.500 g) was dissolved in dry pyridine (5 ml) in a sealable test tube. To this solution was added methyl amine (2.0 ml, 2M in THF) and the tube was sealed and immersed in an oil bath which had been preheated to 120° C. The tube was heated at this temperature for 2 hours, after which time it was cooled and diluted with ice water. The product was extracted into ethyl acetate, washed with dilute HCl, dried (MgSO₄) and evaporated to dryness to afford 0.338 g of 3-(1H-indol-3-yl)-N-methyl-3-phenyl-propionamide, (85%, MS (M+H)=279), which was used in the following step without further purification.

Step 3

[3-(1H-Indol-3-yl)-3-phenyl-propyl]-methyl-amine

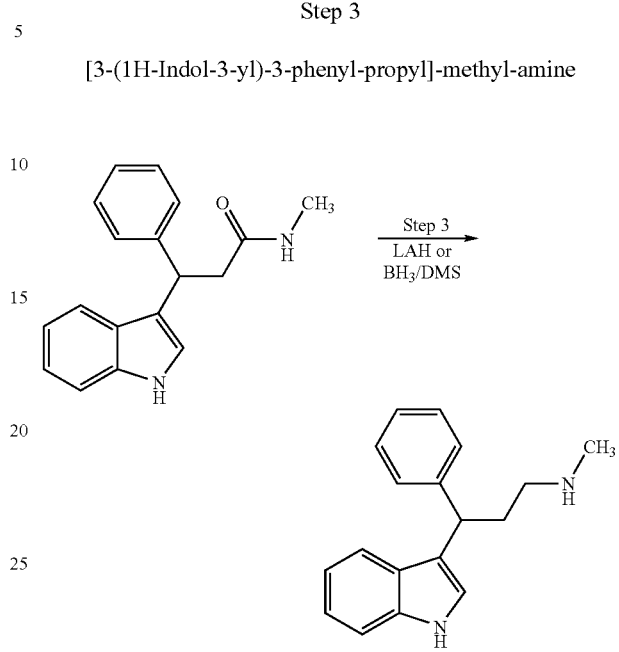

3-(1H-Indol-3-yl)-N-methyl-3-phenyl-propionamide (0.400 g) was dissolved in THF (20 ml) and treated with a solution of lithium aluminum hydride (3 ml 1 M in THF) at reflux for 4 hours at which time 2 ml of additional lithium aluminum hydride was added. After a total of 6 hours, the reaction mixture was cooled and sodium sulfate decahydrate (5 g) was cautiously added. The heterogeneous system was stirred for 15 minutes, filtered, and the filter cake was washed well with ethyl acetate. The filtrate was concentrated, and the product was isolated by chromatography on silica gel using methylene chloride (130): methanol (10): ammonium hydroxide (1), thus affording pure [3-(1H-Indol-3-yl)-3-phenyl-propyl]-methyl-amine (0.235 g amorphous solid, MS (M+H=265).

Similarly prepared, using the appropriate substituted indoles as starting materials, were:

[3-(4-Methoxy-1H-indol-3-yl)-3-phenyl-propyl]-methyl-amine, MS (M+H=295);

[3-(4-Chloro-1H-indol-3-yl)-3-phenyl-propyl]-methyl-amine, MS (M+H=300); and

[3-(4-methoxy-1H-indol-3-yl)-3-pyridin-3-yl-propyl]-methyl-amine, MS (M+H=296);

In an alternate procedure, 3-(1H-Indol-3-yl)-N-methyl-3-phenyl-propionamide (0.400 g) was reduced by refluxing overnight in THF (20 ml) with excess borane-dimethylsulfide to yield [3-(1H-Indol-3-yl)-3-phenyl-propyl]-methyl-amine, which was converted to an oxalate salt (mp 123.7-134.1° C.).

Additional compounds made using the above procedure, using various substituted indoles and substituted benzaldehydes in step 1, are shown in Table 1 above. In certain instances, the addition of one or more equivalents of triethylamine to the reaction mixture of step 1 resulted in improved yields of the desired product.

Example 2

[3-(1H-Indol-3-yl)-3-phenyl-propyl]-methyl-amine

Alternate Procedure

The synthetic procedure of Example 2 is outlined in Scheme I below.

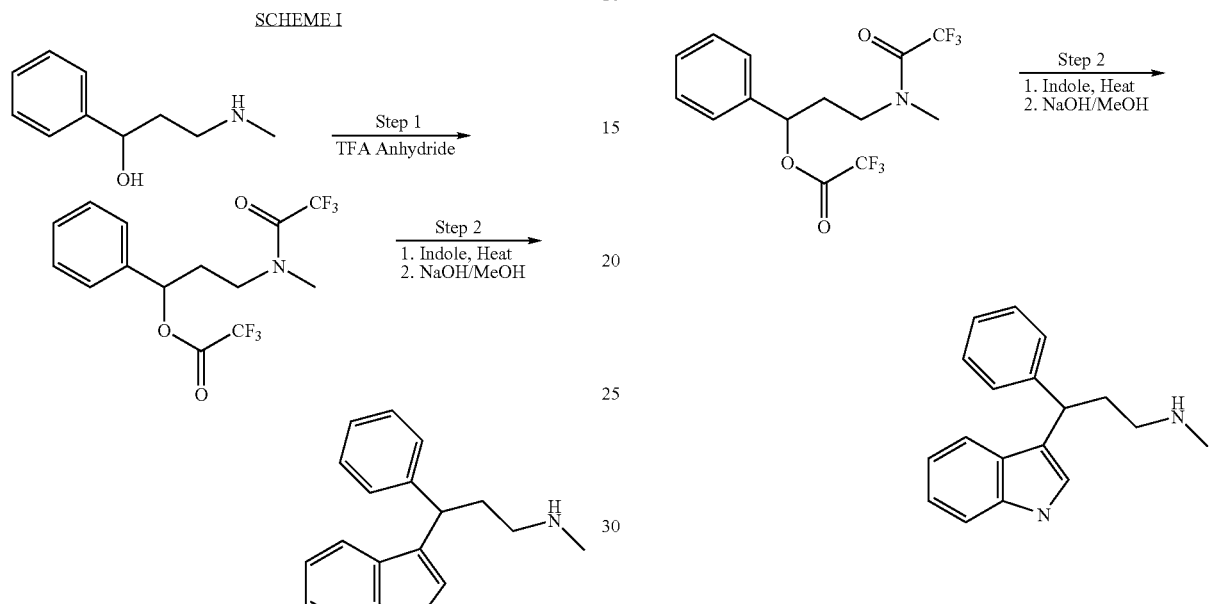

Step 1

Trifluoro-acetic acid 3-[methyl-(2,2,2-trifluoro-acetyl)-amino]-1-phenyl-propyl ester

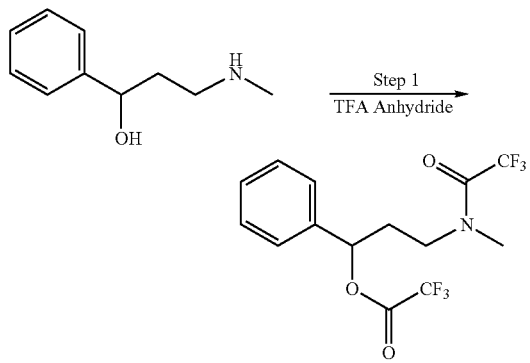

3-Methylamino-1-phenyl-propan-1-ol (1.65 g, 10 mmole) was dissolved in methylene chloride (5 ml), and trifluoroacetic anhydride (5 g, 23.8 mmole) was added in portions. Following the brief exotherm which caused the solvent to boil, the mixture was evaporated to dryness and azeotroped twice with methylene chloride and once with toluene to remove any excess anhydride. The residue was taken up in methylene chloride, applied to a short silica gel column, and eluted with 3:7 ethyl acetate:hexane. The product thus isolated was pumped dry to afford trifluoro-acetic acid 3-[methyl-(2,2,2-trifluoro-acetyl)-amino]-1-phenyl-propyl ester, which was used in the following step without further purification.

Step 2

[3-(1H-Indol-3-yl)-3-phenyl-propyl]-methyl-amine

Trifluoro-acetic acid 3-[methyl-(2,2,2-trifluoro-acetyl)-amino]-1-phenyl-propyl ester from step 1 was taken up in a minimum amount of methylene chloride and transferred to a sealable test tube. Indole (1.17 g, 10 mmole) was added to the solution and the solvent was removed under reduced pressure. A small stirring bar was added, and the tube was sealed with a Teflon-lined cap and placed in a reaction block preheated to 110° C. The reaction was stirred for 30 minutes and then cooled.

Methanol (45 ml) was added to the reaction, followed by sodium hydroxide solution (5 ml, 2N) (where base-sensitive substituents were present, sodium carbonate or bicarbonate was used instead of sodium hydroxide, with longer reaction times). The mixture was allowed to stir at room temperature overnight. Most of the methanol was removed under reduced pressure and the reaction mixture was partitioned between ethyl acetate and water. The layers were separated and the organic layer was evaporated to dryness to give 2.06 g of product as a foam. The crude product was taken up in methylene chloride and purified by chromatography on silica gel. After initial elution with methylene chloride and ethyl acetate, the product was eluted with methylene chloride (130):methanol (10):ammonium hydroxide (1) and isolated as an oil which eventually solidified (0.48 g). (M+H)$^+$=265.3.

Similarly prepared, using the appropriate substituted indoles in step 2, were:

[3-(4-Methoxy-1H-indol-3-yl)-3-phenyl-propyl]-methyl-amine, MS (M+H=295); and

[3-(4-Chloro-1H-indol-3-yl)-3-phenyl-propyl]-methyl-amine, MS (M+H=300).

Additional compounds made using the above procedure, using various substituted indoles in step 2, are shown in Table 1 above.

Example 3

(3-Indol-1-yl-3-phenyl-propyl)-methyl-amine

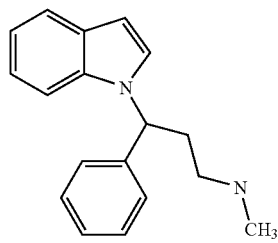

The synthetic procedure of Example 3 is outlined in Scheme J below.

SCHEME J

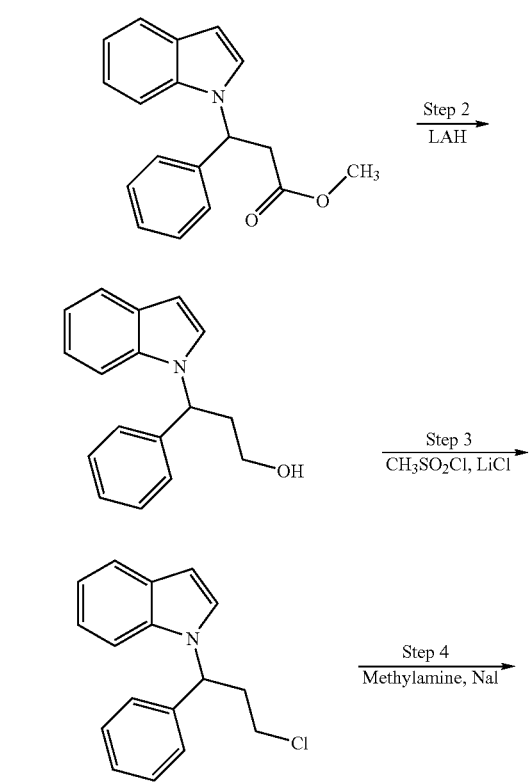

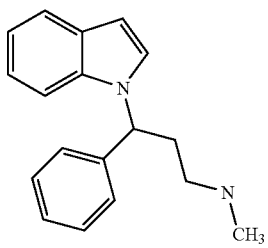

Step 1

3-Indol-1-yl-3-phenyl-propionic acid methyl ester

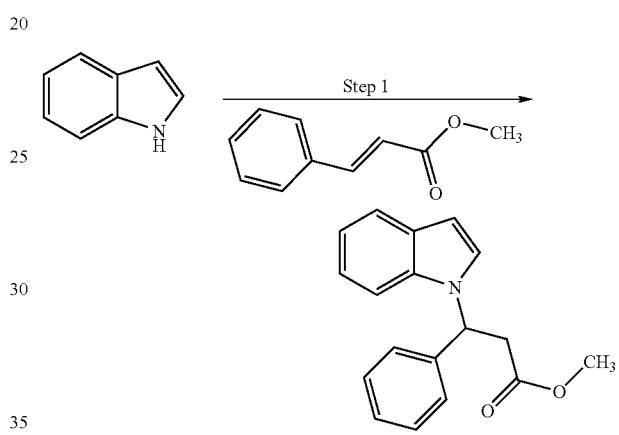

To a solution of indole (2.88 g, 25 mmol) and methyl trans-cinnamate (3.98 g, 25 mmol) in anhydrous DMF (50 mL) was added a suspension of 60% NaH (0.29 g, 7 mmol) at room temperature. The reaction mixture was allowed to stir for 6 hours at room temperature. The reaction mixture was poured into water (300 mL) and product was extracted with EtOAc (2×200 mL). The combined organic extracts were washed with water (5×200 ml), dried over $Na_2SO_4$ and evaporated under vacuum. Purification by chromatography ($SiO_2$, benzene-hexane, 1:9) afforded 1.51 g (22% yield) of 3-indol-1-yl-3-phenyl-propionic acid methyl ester as a white powder: MS 280 (M+H)$^+$.

Step 2

3-Indol-1-yl-3-phenyl-propan-1-ol

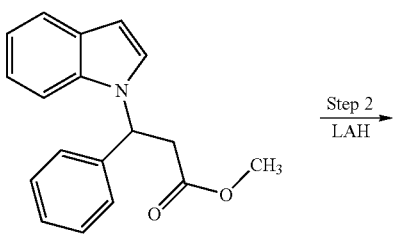

-continued

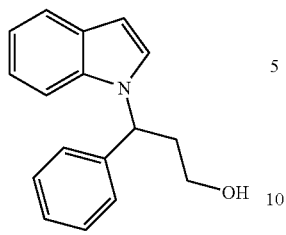

To a solution of 3-indol-1-yl-3-phenyl-propionic acid methyl ester (0.2 g, 0.71 mmol) in THF (5 mL) at 0° C. was added 1M LiAlH₄ in THF (0.71 mL), and the mixture was stirred for 0.5 hours at room temperature. The reaction mixture was quenched by the cautious addition of Na₂SO₄.10H₂O and the reaction mixture was stirred for another 1 h at room temperature. The mixture was filtered and the solvent was removed under vacuum. 3-Indol-1-yl-3-phenyl-propan-1-ol was obtained as a clear oil (0.166 g, 92% yield).

Step 3

1-(3-Chloro-1-phenyl-propyl)-1H-indole

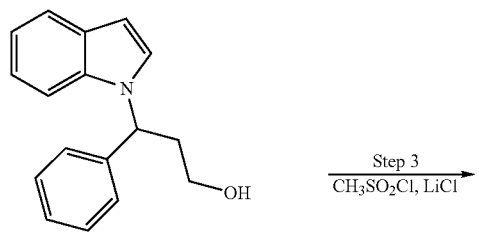

To a solution of 3-indol-1-yl-3-phenyl-propan-1-ol (0.166 g, 0.66 mmol) in CH₂Cl₂ (20 mL) and triethylamine (0.087 g, 0.85 mmol) at 0° C. was added methanesulfonyl chloride (0.083 g, 0.72 mmol), and the mixture was stirred for 1 hour at room temperature. The reaction mixture was poured into an aqueous saturated solution of NaHCO₃ (50 mL) and extracted with CH₂Cl₂ (2×50 mL). The organic layer was dried over Na₂SO₄, and the solvent was removed under vacuum. The residue was diluted in MeCN (50 mL) and treated with LiCl (0.084 g, 1.98 mmol), and the reaction mixture was heated to reflux temperature for 24 hours. The solvent was removed under vacuum and the crude product was chromatographed (SiO₂, Hexanes/EtOAc, 9:1) to afford 0.145 g (81% yield) of 1-(3-chloro-1-phenyl-propyl)-1H-indole as an oil.

Step 4

(3-Indol-1-yl-3-phenyl-propyl)-methyl-amine

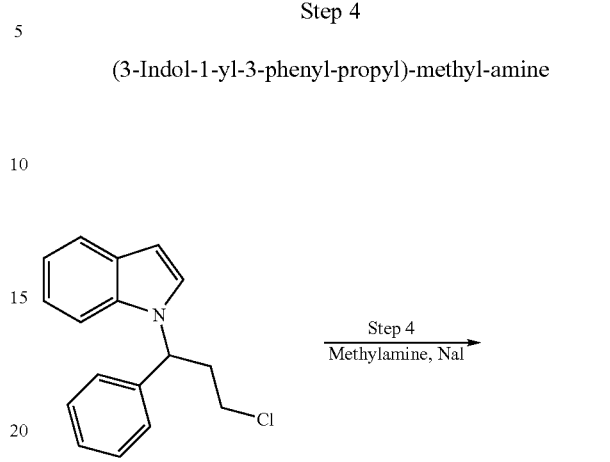

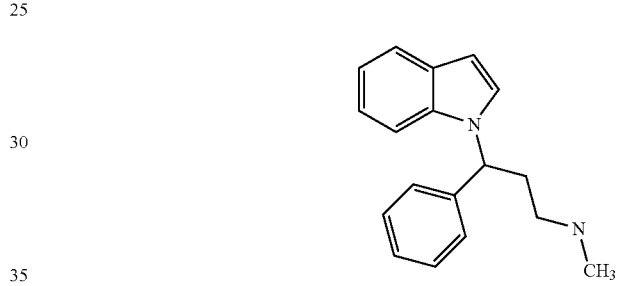

A suspension of NaI (0.235 g, 1.56 mmol) and 1-(3-chloro-1-phenyl-propyl)-1H-indole (0.141 mg, 0.52 mmol) in ethanolic methylamine solution (33%, 2 mL) was heated at 100° C. for 1 hour under microwave irradiation (sealed tube). The reaction mixture was poured into water (30 mL) and extracted with CH₂Cl₂ (3×25 mL). The combined organic layers were dried (Na₂SO₄), and evaporated under vacuum. Purification by chromatography (SiO₂, CH₂Cl₂-MeOH—NH₄OH, 18:1: 0.1) gave 0.125 g (90% yield) of pure (3-indol-1-yl-3-phenyl-propyl)-methyl-amine as an oil. Treatment of this amino compound with an ethereal solution of HCl (2M, 0.26 mL) gave the corresponding hydrochloride salt (0.127 g) as a white powder: mp=218-219° C.; $^1$H NMR (DMSO) δ 2.53 (s, 3H), 2.60-2.89 (m, 4H), 5.86-5.91 (m, 1H), 6.585 (d, 1H, J=3.22 Hz), 6.98-7.12 (m, 2H), 7.20-7.34 (m, 5H), 7.52-7.54 (m, 2H), 7.71 (d, 1H, J=3.22 Hz), 9.0 (broad s, 1H); MS (EI) m/z 265 (M+H)⁺.

Additional compounds made using the above procedure, using various substituted indoles and/or substituted acrylic esters in step 1 are shown in Table 1 above.

Using the above procedure, but replacing indole with indazole or benzimidazole in step 1, afforded corresponding indazole and benzimidazole compounds in accordance with the invention, representative compounds of which are shown in Table 1.

Example 4

[3-(1H-Indol-2-yl)-3-phenyl-propyl]-methyl-amine

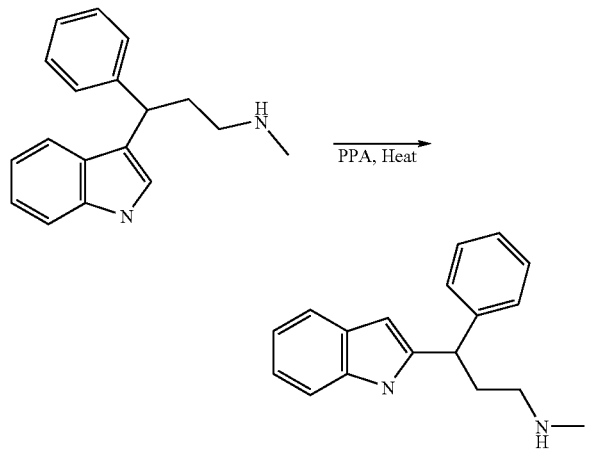

Using the procedure of Kost et al, Vestnik Moskovskogo Universiteta, Seriya 2: Khimiya (1975), 16(4), 467-71, [3-(1H-Indol-3-yl)-3-phenyl-propyl]-methyl-amine (0.477 g, 1.8 mmole) was placed in a tube with 10 g of polyphosphoric acid and a stirring bar. The tube was sealed and placed in a reaction heating block at 100° C. After 90 minutes, the reaction mixture was diluted with water (ca. 50 ml) and carefully basified by the slow addition of 2N NaOH. The basified solution was extracted with ethyl acetate, and a small amount of colored polymer was filtered and discarded. The residue obtained by evaporation of the solvent was purified by chromatography on silica gel using a mixture of methylene chloride (130):methanol (10):ammonium hydroxide (1) for elution, to yield [3-(1H-indol-2-yl)-3-phenyl-propyl]-methyl-amine as an oil (0.265 g), 265 $(M+H)^+$.

Example 5

[3-(5-Methoxy-benzofuran-2-yl)-3-phenyl-propyl]-methyl-amine

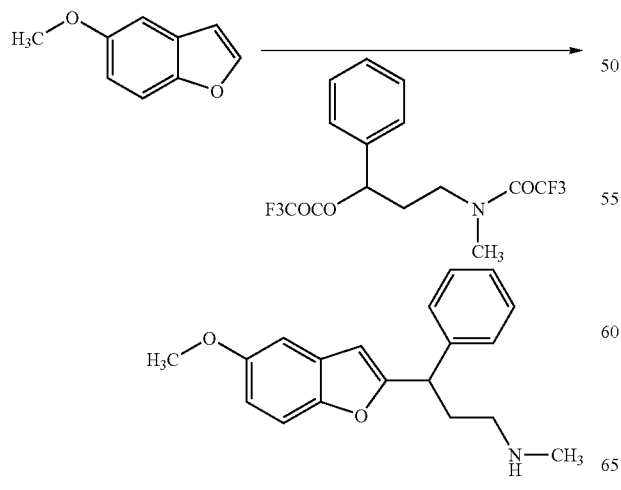

5-methoxybenzofuran (0.48 g) and trifluoro-acetic acid 3-[methyl-(2,2,2-trifluoro-acetyl)-amino]-1-phenyl-propyl ester (0.48 g) were mixed and heated in a sealed tube at 110° C. for 90 minutes. Upon cooling, the reaction mixture was taken up in methanol and treated with excess 1N sodium hydroxide solution, sufficient to form a strongly basic solution. After stirring for 20 minutes, the reaction mixture was concentrated at reduced pressure to remove the bulk of the methanol. The resulting mixture was partitioned between ethyl acetate and water. The layers were separated and the organic layer was evaporated to dryness. Purification by column chromatography (silica gel, dichloromethane (130):methanol (10):ammonium hydroxide (1)) followed by preparative tlc afforded [3-(5-Methoxy-benzofuran-2-yl)-3-phenyl-propyl]-methyl-amine (M+H=296) as the major component.

Additional compounds made using the above procedure are shown in Table 1 above.

Example 6

[3-(5-Methoxy-benzofuran-2-yl)-3-phenyl-propyl]-methyl-amine

The synthetic procedure of Example 6 is outlined in Scheme K below.

SCHEME K

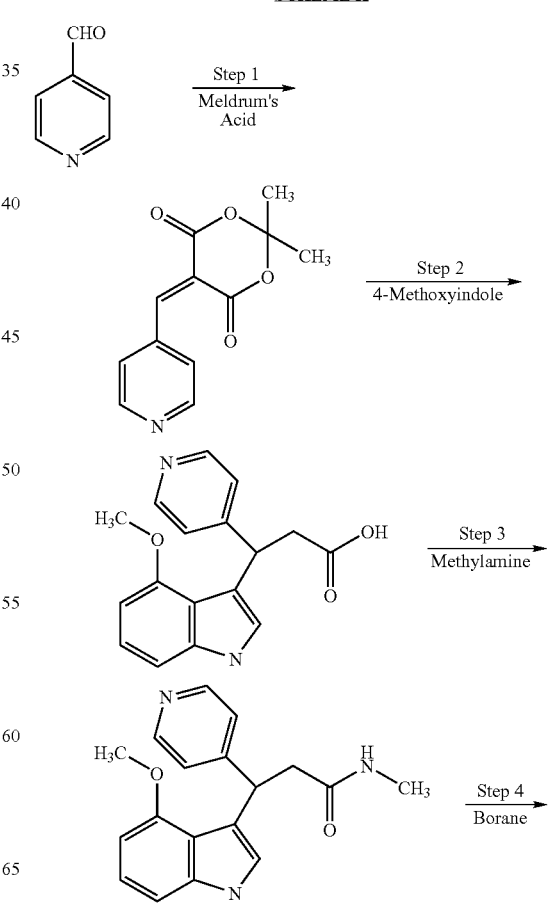

-continued

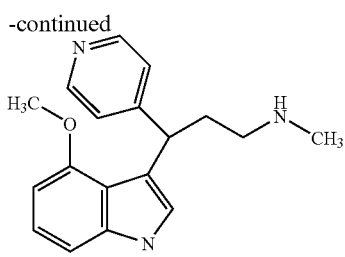

Step 1

2,2-Dimethyl-5-pyridin-4-ylmethylene-[1,3]dioxane-4,6-dione

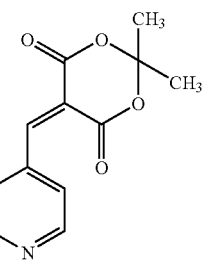

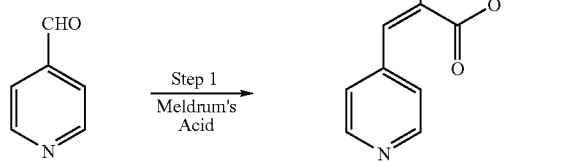

Pyridine-4-carboxaldehyde (2.04 g) was mixed with Meldrum's acid (2,2-Dimethyl-[1,3]dioxane-4,6-dione, 2.7 g) and proline (0.20 g) in acetonitrile (40 ml) with stirring under a nitrogen atmosphere. Almost immediately product began to precipitate. The mixture was stirred overnight, filtered and washed with ether, affording 3.7 g of 2,2-dimethyl-5-pyridin-4-ylmethylene-[1,3]dioxane-4,6-dione which was used with no further purification in the next step.

Step 2

3-(4-methoxy-1H-indol-3-yl)-3-pyridin-4-yl-propionic acid

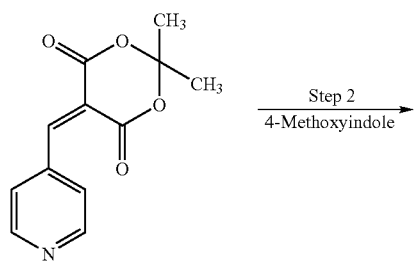

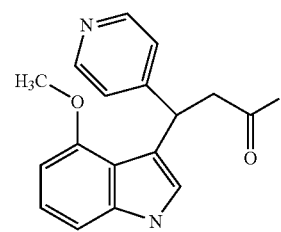

2,2-Dimethyl-5-pyridin-4-ylmethylene-[1,3]dioxane-4,6-dione (0.27 g) and 4-methoxyindole (0.17 g) were mixed and heated in a sealed tube at 110° C. for 2 h. The cooled residue was purified by chromatography on silica gel, eluting first with ethyl acetate and then with dichloromethane (60):methanol (10):ammonium hydroxide (1) to afford 0.09 g of 3-(4-methoxy-1H-indol-3-yl)-3-pyridin-4-yl-propionic acid.

Step 3

3-(4-Methoxy-1H-indol-3-yl)-N-methyl-3-pyridin-4-yl-propionamide

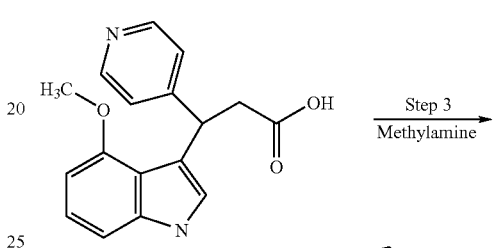

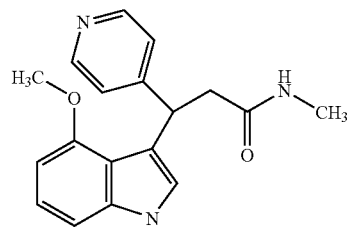

3-(4-Methoxy-1H-indol-3-yl)-3-pyridin-4-yl-propionic acid (0.09 g) was dissolved in a mixture of 5 ml dichloromethane and 1 ml dimethylformamide. To this mixture was added methyl amine (0.2 ml 2.0 M in THF), (Benzotriazol-1-yloxy)tris(dimethylamino) hexafluorophosphate (Bop reagent) (0.16 g), and triethylamine (0.084 g). The mixture was stirred under a nitrogen atmosphere for 2 h at room temperature. Ethyl acetate was added and the mixture was washed with water 3 times followed by brine once. The organic layer was dried and concentrated, and purified on silica gel eluting with dichloromethane (130):methanol (10):ammonium hydroxide (1) to afford 0.095 g of 3-(4-methoxy-1H-indol-3-yl)-N-methyl-3-pyridin-4-yl-propionamide.

Step 4

[3-(4-Methoxy-1H-indol-3-yl)-3-pyridin-4-yl-propyl]-methyl-amine

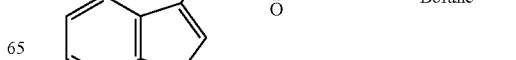

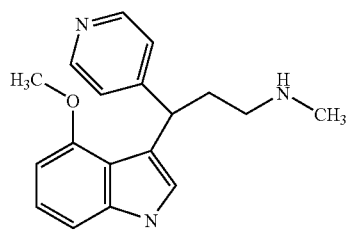

3-(4-methoxy-1H-indol-3-yl)-N-methyl-3-pyridin-4-yl-propionamide was reduced with borane using the procedure described in step 3 of Example 1 to afford [3-(4-methoxy-1H-indol-3-yl)-3-pyridin-4-yl-propyl]-methyl-amine, (M+H=296).

Additional compounds made using the above procedure are shown in Table 1 above.

Example 7

[3-(4-Methoxy-2,3-dihydro-indol-1-yl)-3-phenyl-propyl]-methyl-amine

The synthetic procedure of Example 7 is outlined in Scheme L below.

Step 1

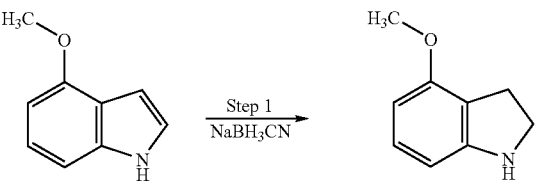

4-methoxyindole (0.735 g) was dissolved in acetic acid (25 ml) and cooled in an ice bath. To this solution was added sodium cyanoborohydride (0.942 g) in portions. After the addition was complete, the solution was allowed to come to room temperature and the solution was stirred for an hour. The solvent was removed under vacuum and the residue was taken up in ethyl acetate, washed with sodium carbonate solution, water and finally with brine. The organic layer was evaporated and the resulting product was purified on a silica gel column eluting with ethyl acetate:dichloromethane (5:95) to give 0.404 g of 4-methoxyindoline.

Step 2

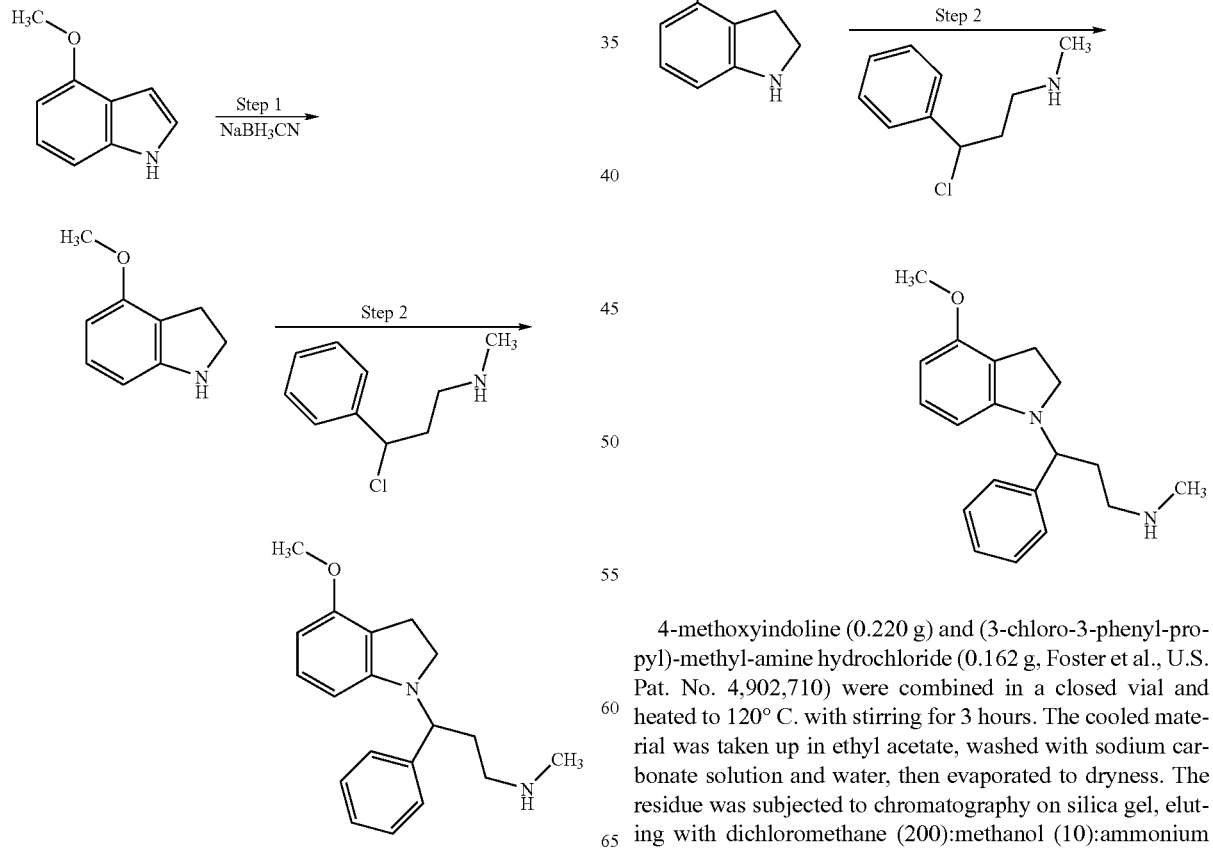

4-methoxyindoline (0.220 g) and (3-chloro-3-phenyl-propyl)-methyl-amine hydrochloride (0.162 g, Foster et al., U.S. Pat. No. 4,902,710) were combined in a closed vial and heated to 120° C. with stirring for 3 hours. The cooled material was taken up in ethyl acetate, washed with sodium carbonate solution and water, then evaporated to dryness. The residue was subjected to chromatography on silica gel, eluting with dichloromethane (200):methanol (10):ammonium hydroxide (1) to give 0.126 g of [3-(4-methoxy-2,3-dihydro-indol-1-yl)-3-phenyl-propyl]-methyl-amine, (M+H=297).

Additional compounds made using the above procedure are shown in Table 1 above.

Example 8

[3-(6-Methoxy-indazol-2-yl)-3-phenyl-propyl]-methyl-aine

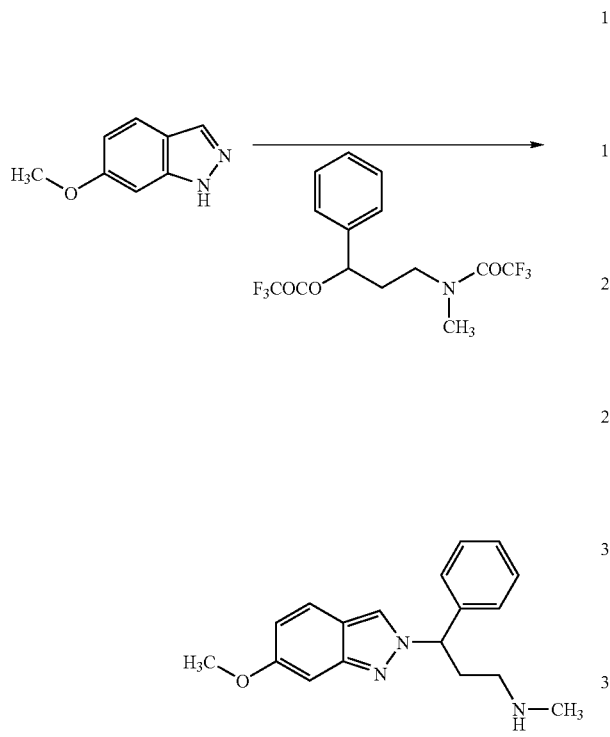

6-Methoxyindazole (0.24 g, Tiefenthaler et al., Helvetica Chimica Acta (1967), 50(8), 2244-58) and trifluoro-acetic acid 3-[methyl-(2,2,2-trifluoro-acetyl)-amino]-1-phenyl-propyl ester (0.596 g) were placed in a sealed vial and heated to 120° C. for 4 hours. The dark gum was taken up into dichloromethane and reprotected with trifluoroacetic anhydride (2 ml) by stirring for 2 hours. The mixture was evaporated to dryness and purified on silica gel by elution with ethyl acetate-hexane (3:7) to afford 0.146 g of (3-indazol-2-yl-3-phenyl-propyl)-methyl-carbamic acid trifluoromethyl ester (not shown). This trifluoroacetate was dissolved in methanol (25 ml) and 1N aqueous sodium hydroxide was added. After stirring at room temperature for 3 hours, the mixture was evaporated to dryness and partitioned between ethyl acetate and water. The organic layer was dried and evaporated to dryness. Purification was carried out by chromatography on silica gel by elution with dichloromethane (200):methanol (10):ammonium hydroxide (1) to give 0.067 g of [3-(6-methoxy-indazol-2-yl)-3-phenyl-propyl]-methyl-amine, (M+H=296).

Additional compounds made using the above procedure are shown in Table 1 above.

Example 9

Resolution of [3-(4-Methoxy-1H-indol-3-yl)-3-phenyl-propyl]-methyl-amine to (R)-[3-(4-Methoxy-1H-indol-3-yl)-3-phenyl-propyl]-methyl-amine and (S)-[3-(4-Methoxy-1H-indol-3-yl)-3-phenyl-propyl]-methyl-amine

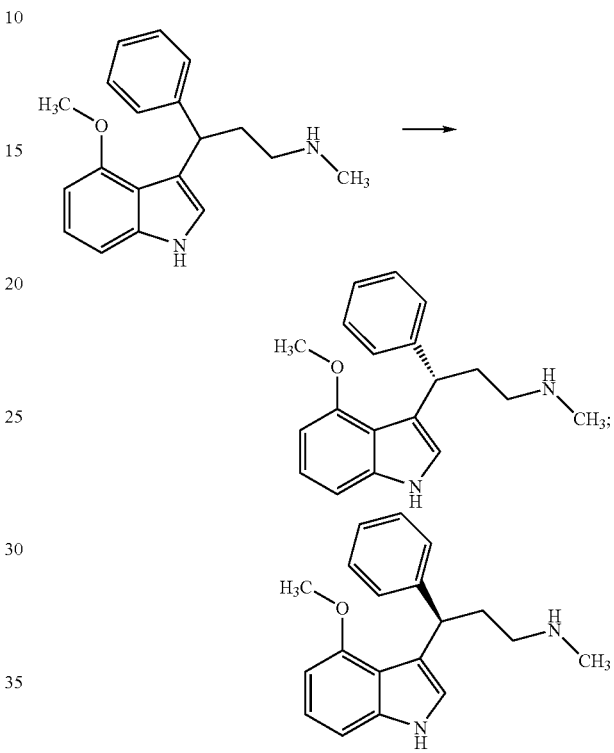

[3-(4-Methoxy-1H-indol-3-yl)-3-phenyl-propyl]-methyl-amine, 3.2 g (prepared using the procedure of Example 1), was dissolved in dichloromethane (300 ml), and di-tert-butyl carbonate (3.2 g) was added. The solution thus formed was stirred at room temperature over night and then evaporated to dryness. The crude mixture was applied to a silica gel column and eluted with ethyl acetate-hexane (1:9). When product began to elute, the solvent was changed to a 15:85 mixture of the same two solvents. Upon evaporation of all pure fractions, the Boc-protected product (not shown) was isolated as a colorless foam, 4.06 g after thorough drying.

The mixture of Boc-protected enantiomers was then separated by multiple injections onto a 50×500 mm Chiralpak AD preparative column using a 75:25 mixture of hexanes:isopropanol at 50 ml/min. The material from the first peak (0.99 g) was dissolved in dry acetonitrile (50 ml) and sodium iodide (2.02 g) was added. Chlorotrimethylsilane (1.46 g) was added dropwise with stirring. Twenty-five minutes after the addition, saturated sodium bicarbonate solution was added followed by ethyl acetate. The two phase system was stirred gently for 10 minutes and the layers were separated and the organic layer was evaporated to dryness to give 0.992 g of a crystalline solid, which was triturated with first with dichloromethane and then with ethyl acetate to afford 0.805 g of (R)-[3-(4-methoxy-1H-indol-3-yl)-3-phenyl-propyl]-methyl-amine hydroiodide salt, homogeneous by LC/MS analysis. This salt was converted to free-base by dissolving in a mixture of 100 ml water and 25 ml methanol, and treating with 4 ml 2N sodium hydroxide solution. After stirring for 10 minutes, the milky suspension was extracted with two portions of ethyl acetate. The combined organic extracts were washed with water, dried over magnesium sulfate, and evaporated to dryness to afford (R)-[3-(4-methoxy-1H-indol-3-yl)-3-phenyl-propyl]-methyl-amine free base as a white solid (0.543 g). The hydrochloride salt was then prepared by taking the material up in ethyl acetate and dropwise adding 3 ml 1M hydrogen chloride in ether. The solvents were immediately removed without heating. The residual hydrochloride salt was taken up in dichloromethane and evaporated to dryness to remove any excess HCl. Finally the residue was taken up in a minimum of dichloromethane, ethyl acetate was added and the solvents were removed under reduced pressure at 40° C. The beige powder which resulted was dried over night at 40° C. to afford 0.575 g of (R)-[3-(4-methoxy-1H-indol-3-yl)-3-phenyl-propyl]-methyl-amine hydrochloride salt, homogeneous by LC/MS with M+H=295.

The above procedure was repeated for the material from the second peak to yield (S)-[3-(4-methoxy-1H-indol-3-yl)-3-phenyl-propyl]-methyl-amine, M+H=295.

Stereoisomers of additional compounds isolated using the above procedure are shown in Table 1 above.

Example 10

[3-Cyclohexyl-3-(4-methoxy-1H-indol-3-yl)-propyl]-methylamine

The synthetic procedure of Example 10 is outlined in Scheme M below.

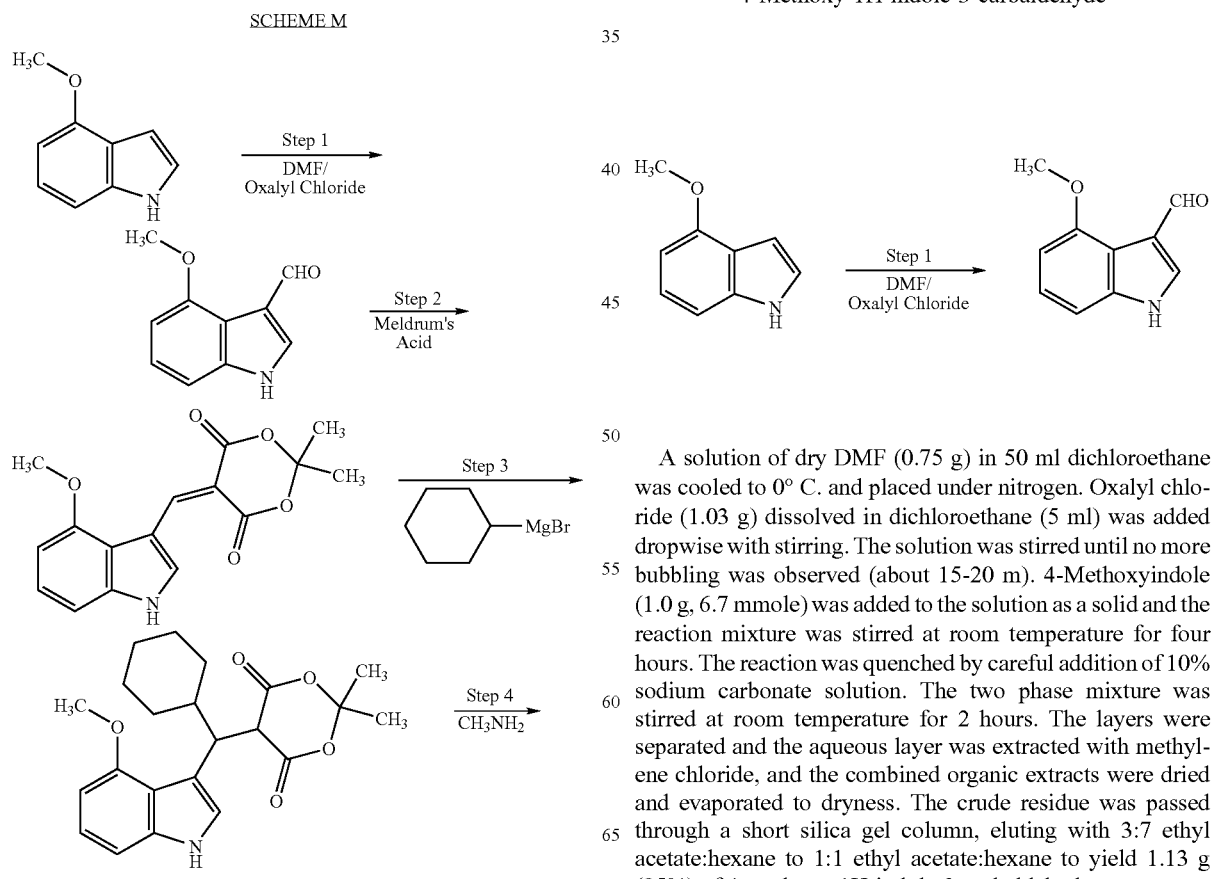

-continued

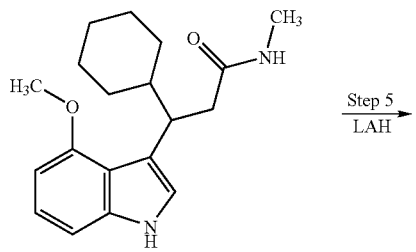

Step 1

4-Methoxy-1H-indole-3-carbaldehyde

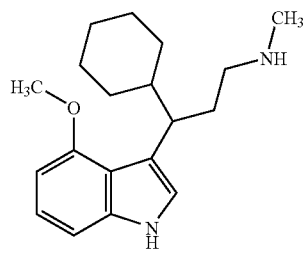

A solution of dry DMF (0.75 g) in 50 ml dichloroethane was cooled to 0° C. and placed under nitrogen. Oxalyl chloride (1.03 g) dissolved in dichloroethane (5 ml) was added dropwise with stirring. The solution was stirred until no more bubbling was observed (about 15-20 m). 4-Methoxyindole (1.0 g, 6.7 mmole) was added to the solution as a solid and the reaction mixture was stirred at room temperature for four hours. The reaction was quenched by careful addition of 10% sodium carbonate solution. The two phase mixture was stirred at room temperature for 2 hours. The layers were separated and the aqueous layer was extracted with methylene chloride, and the combined organic extracts were dried and evaporated to dryness. The crude residue was passed through a short silica gel column, eluting with 3:7 ethyl acetate:hexane to 1:1 ethyl acetate:hexane to yield 1.13 g (95%) of 4-methoxy-1H-indole-3-carbaldehyde.

Step 2

5-(4-Methoxy-1H-indol-3-ylmethylene)-2,2-dimethyl-[1,3]dioxane-4,6-dione

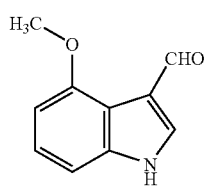

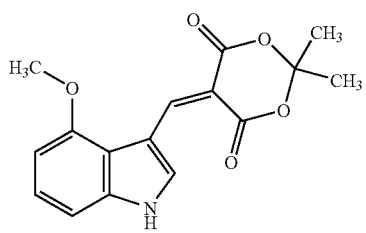

4-MethoxyIndole-3-carboxaldehyde (5.0 g) and Meldrum's acid (2,2-Dimethyl-[1,3]dioxane-4,6-dione, 4.11 g) were mixed in toluene (200 ml). To this mixture was added 0.6 ml each of piperidine and acetic acid. The reaction mixture was stirred at room temperature for four hours. The precipitate was filtered and washed with toluene to afford 4.25 g of crude 5-(4-methoxy-1H-indol-3-ylmethylene)-2,2-dimethyl-[1,3]dioxane-4,6-dione as an orange solid which was used without further purification.

Step 3

5-[Cyclohexyl-(4-methoxy-1H-indol-3-yl)-methyl]-2,2-dimethyl-[1,3]dioxane-4,6-dione

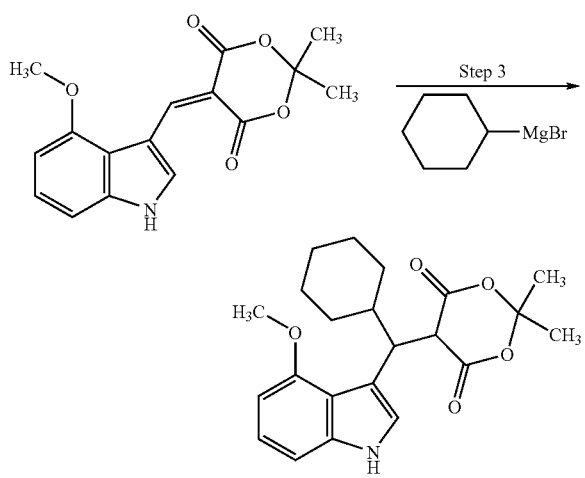

5-(4-Methoxy-1H-indol-3-ylmethylene)-2,2-dimethyl-[1,3]dioxane-4,6-dione (0.392 g) was dissolved in dry THF (15 ml) and added slowly to cyclohexyl-magnesium bromide (10 ml, 1M) at room temperature with stirring. The reaction was stirred for 20 minutes, and then was worked up by the careful addition of saturated ammonium chloride solution, acidified with dilute HCl, and extracted with ethyl acetate. The crude product was purified on silica gel. Elution was done with 3:7 ethyl acetate-hexane to afford 0.390 g of 5-[cyclohexyl-(4-methoxy-1H-indol-3-yl)-methyl]-2,2-dimethyl-[1,3]dioxane-4,6-dione.

Step 4

3-Cyclohexyl-3-(4-methoxy-1H-indol-3-yl)-N-methyl-propionamide

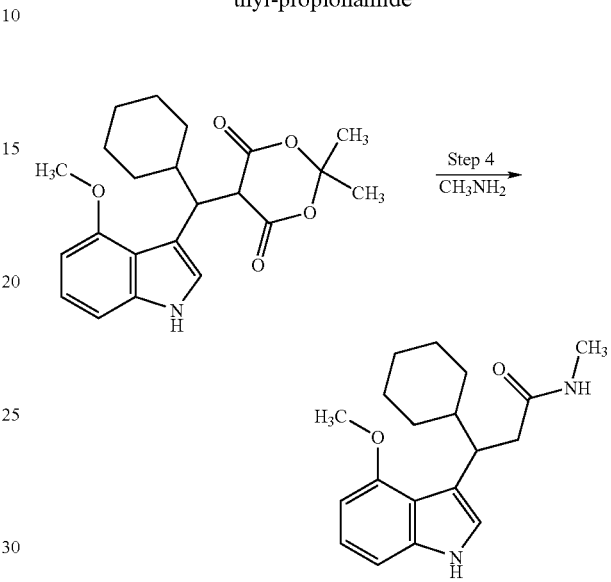

5-[Cyclohexyl-(4-methoxy-1H-indol-3-yl)-methyl]-2,2-dimethyl-[1,3]dioxane-4,6-dione was treated with methyl amine using the procedure of step 2 of Example 1 to afford 3-cyclohexyl-3-(4-methoxy-1H-indol-3-yl)-N-methyl-propionamide, (M+H=315).

Step 5

[3-Cyclohexyl-3-(4-methoxy-1H-indol-3-yl)-propyl]-methyl-amine

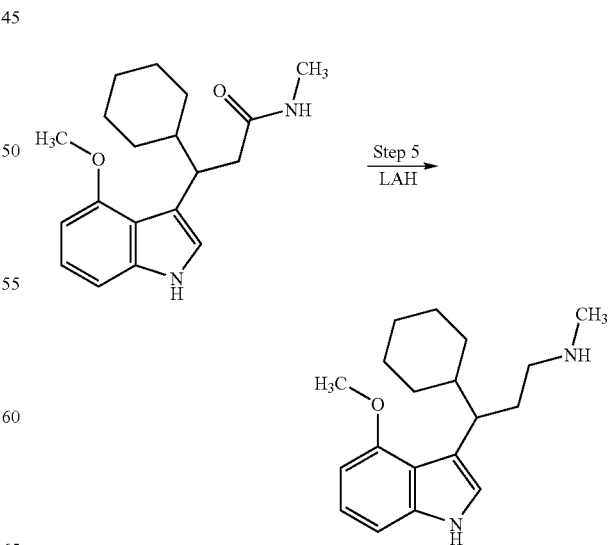

3-Cyclohexyl-3-(4-methoxy-1H-indol-3-yl)-N-methyl-propionamide was treated with lithium aluminum hydride using the procedure of step 3 of Example 1 to yield [3-cyclohexyl-3-(4-methoxy-11H-indol-3-yl)-propyl]-methyl-amine, (M+H=301).

Similarly prepared, using the appropriate Grignard reagents in step 3, were:
[3-Cyclohexyl-3-(1H-indol-3-yl)-propyl]-methyl-amine;
[3-(1H-Indol-3-yl)-4-methyl-pentyl]-methyl-amine;
[3-(1H-Indol-3-yl)-4,4-dimethyl-pentyl]-methyl-amine;
[3-(1H-Indol-3-yl)-4-phenyl-butyl]-methyl-amine; and
[3-(1H-Indol-3-yl)-5-phenyl-pentyl]-methyl-amine.

Additional compounds made using the above procedure are shown in Table 1 above.

Example 11

1-(3-Methylamino-1-phenyl-propyl)-1H-indazole-4-carbonitrile

The synthetic procedure of Example 11 is outlined in Scheme N below.

SCHEME N

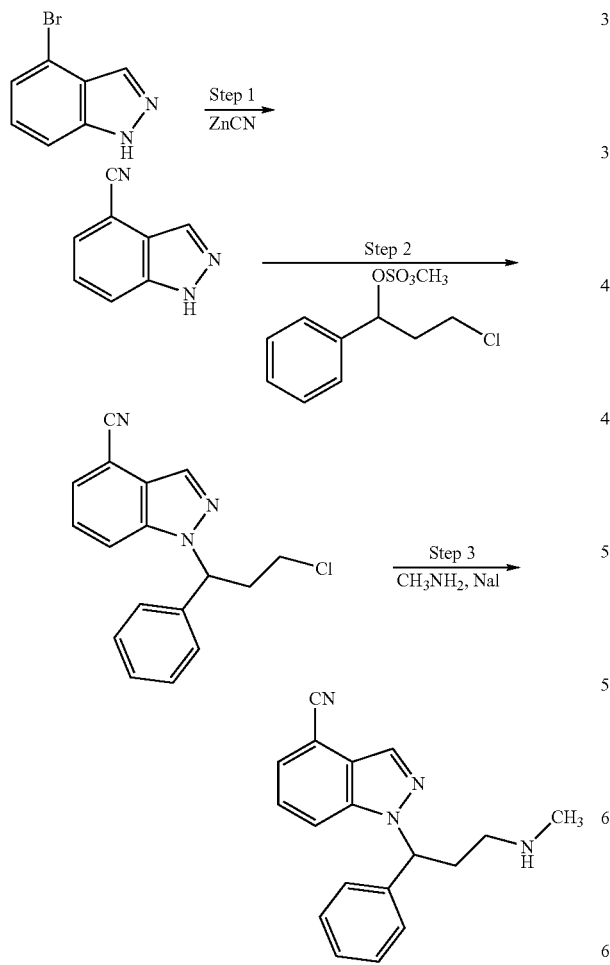

Step 1

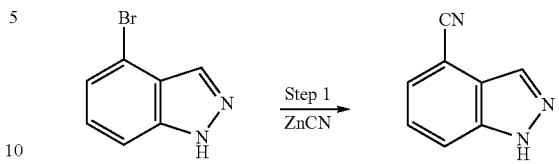

4-Bromoindazole (1.0 g, Judkins et al., WO 9641803) and zinc cyanide (0.6 g) were added to N-methylpyrrolidinone (12.5 ml) and placed under an argon atmosphere. To this mixture was added tetrakis(triphenylphosphine)palladium(0) (0.88 g) and the reaction was heated to 85° C. overnight. The reaction mixture was cooled and partitioned between ethyl acetate and water, the organic layer was washed with brine, dried (MgSO$_4$), and evaporated to dryness. The product was purified by chromatography on silica gel using ethyl acetate-dichloromethane (5:95) as the eluting solvent to afford 0.581 g pure 4-cyanoindazole.

Step 2

1-(3-Chloro-1-phenylpropyl)-1H-indazole-4-carbonitrile

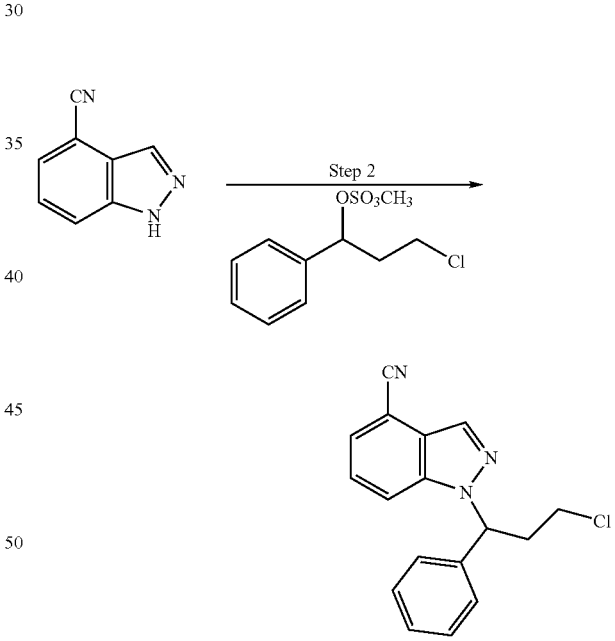

Sodium hydride (0.092 g, 60% in oil) was added to a solution of 4-cyanoindazole (0.300 g) in N-methylpyrrolidinone (5 mL) and the reaction mixture was stirred at room temperature for 30 minutes. Methanesulfonic acid 3-chloro-1-phenyl-propyl ester (0.573 g) was added followed by 3 ml more of N-methylpyrrolidinone. The reaction mixture was stirred for an additional 6 hours at room temperature. The reaction mixture was partitioned between water and ethyl acetate, and the organic layer was washed with water, then with brine, and dried (MgSO$_4$). Evaporation to dryness gave a residue which was purified by column chromatography on silica gel using ethyl acetate-hexane (1:9) to give 1-(3-chloro-1-phenyl-propyl)-1H-indazole-4-carbonitrile (0.228 g) as a foam, (M+H=297).

Step 3

1-(3-Methylamino-1-phenyl-propyl)-1H-indazole-4-carbonitrile 1-(3-Chloro-1-phenyl-propyl)-1H-indazole-4-carbonitrile (0.228 g) was dissolved in 3 ml of a 33% solution of methylamine in methanol, and sodium iodide (0.100 g) was added. The reaction mixture was subjected to microwave irradiation at 100° C. for 45 minutes. The solvents were removed from the cooled reaction mixture and the crude product was partitioned between ethyl acetate and water. The organic layer was washed and evaporated and the residue was purified by chromatography on silica gel eluting with dichloromethane (200): methanol (10):ammonium hydroxide (1) to give 0.151 g of 1-(3-methylamino-1-phenyl-propyl)-1H-indazole-4-carbonitrile, (M+H=291).

Additional compounds made using the above procedure, using the appropriate substituted indoles and indazoles, are shown in Table 1 above.

Example 12

(S)-[3-(4-Chloro-indol-1-yl)-3-phenyl-propyl]-methyl-amine

The synthetic procedure of Example 12 is outlined in Scheme O below.

SCHEME O

Step 1

Methanesulfonic acid 3-chloro-1-phenyl-propyl ester

To a solution of (R) 3-chloro-1-phenyl-propan-1-ol (Aldrich) (0.250 g) in 40 ml dichloromethane was added triethylamine (0.272 g) at 0° C. followed by the dropwise addition of methanesulfonyl chloride (0.185 g). The reaction mixture was stirred at this temperature for 2 hours and then quenched by the addition of sodium bicarbonate solution. The phases were separated and the organic phase was evaporated to dryness to afford methanesulfonic acid 3-chloro-1-phenyl-propyl ester as an oil which was used directly in the next step.

Step 2

(S)-4-Chloro-1-(3-chloro-1-phenyl-propyl)-1H-indole

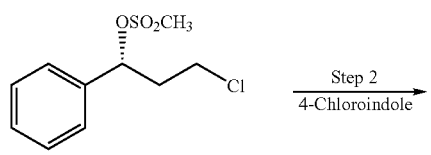

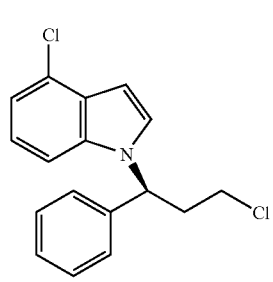

To a solution of 4-chloroindole (0.222 g) in dry DMF (7.5 ml) was added sodium hydride (0.064 g) at room temperature. The mixture was stirred at the same temperature for 30 minutes and then the crude methanesulfonic acid 3-chloro-1-phenyl-propyl ester from the previous step was dissolved in DMF (5 ml) and added at 0° C. to the reaction mixture and stirred for 2 hours. The reaction mixture was partitioned between ethyl acetate and water, the organic layer was washed twice with water and once with brine, then dried over magnesium sulfate, filtered and evaporated to dryness to afford an oil. Purification of the crude product was done by column chromatography on silica gel, eluting the desired product with ethyl acetate-hexane (1:9). The (S) 4-chloro-1-(3-chloro-1-phenyl-propyl)-1H-indole thus produced weighed 0.251 g, sufficiently pure for use in the following step.

Step 3

(S)-[3-(4-Chloro-indol-1-yl)-3-phenyl-propyl]-methyl-amine

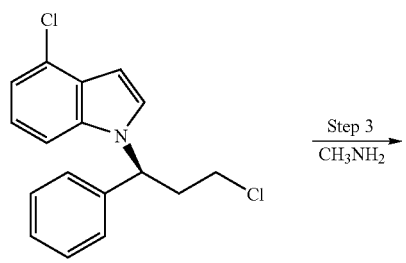

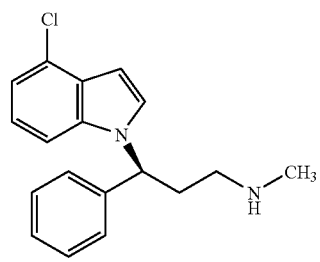

(S) 4-chloro-1-(3-chloro-1-phenyl-propyl)-1H-indole (0.228 g) was reacted with methylamine following the procedure of step 3 of Example 11 to afford 0.135 g of (S)-[3-(4Chloro-indol-1-yl)-3-phenyl-propyl]-methyl-amine, (M+H=300).

Example 13

[3-(7-Methoxy-indol-1-yl)-3-pyridin-3-yl-propyl]-methyl-amine

The synthetic procedure of Example 13 is outlined in Scheme P below.

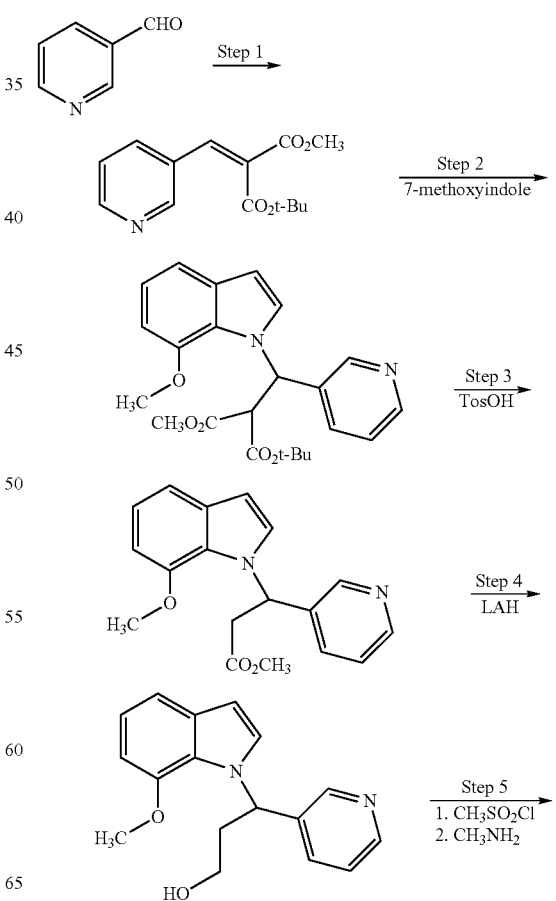

-continued

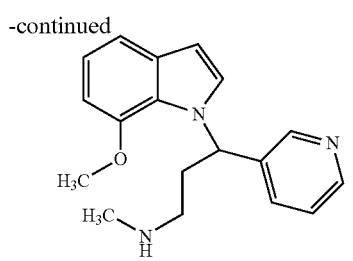

Step 1

2-Pyridin-3-ylmethylene-malonic acid tert-butyl ester methyl ester

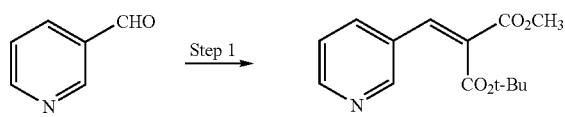

A mixture of pyridine-3-carboxaldehyde (2.72 g), propanedioic acid, 1,1-dimethylethyl methyl ester (4.42 g), piperidine (0.173 g) and benzoic acid (0.155 g) in benzene (100 ml) was heated at reflux with removal of water to a Dean-Stark trap for 12 hours. The cooled mixture was washed with bicarbonate solution, concentrated under vacuum and the residue was purified by column chromatography, eluting with ethyl acetate-hexane (3:7) to afford racemic 2-pyridin-3-yl-methylene-malonic acid tert-butyl ester methyl ester as an oil (3.21 g).

Step 2

2-[(7-Methoxy-indol-1-yl)-pyridin-3-yl-methyl]-malonic acid tert-butyl ester methyl ester

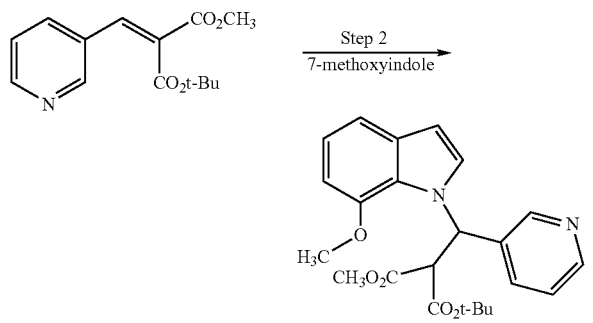

To a solution of 7-methoxyindole in DMF was added sodium hydride (0.086 g, 60% in oil) at 0° C. and the resulting mixture was stirred for 30 minutes. 2-Pyridin-3-ylmethylene-malonic acid tert-butyl ester methyl ester (0.470 g) was added and the mixture was stirred for 2 hours at room temperature. The reaction mixture was partitioned between ethyl acetate and water, the organic layer was washed twice with water and once with brine, then dried over magnesium sulfate, filtered and evaporated to dryness to afford the crude 2-[(7-methoxy-indol-1-yl)-pyridin-3-yl-methyl]-malonic acid tert-butyl ester methyl ester, which was crystallized from a hexane-ether mixture (0.207 g).

Step 3

3-(7-Methoxy-indol-1-yl)-3-pyridin-3-yl-propionic acid methyl ester

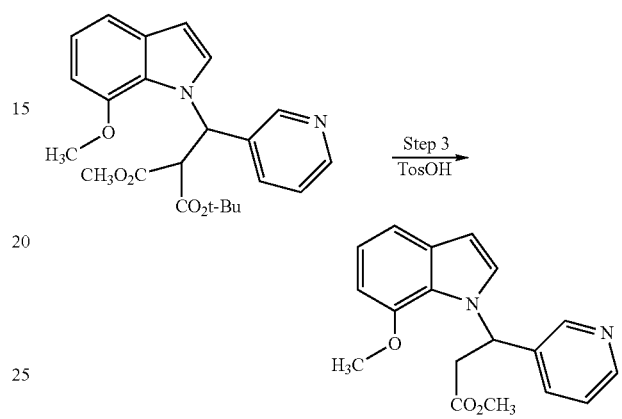

2-[(7-Methoxy-indol-1-yl)-pyridin-3-yl-methyl]-malonic acid tert-butyl ester methyl ester (0.200 g) was dissolved in toluene (50 ml) and treated with p-toluenesulfonic acid (0.102 g). The mixture was brought to reflux temperature and stirred for 4 hours. The reaction mixture was partitioned between ethyl acetate and aqueous bicarbonate solution, the organic layer was dried over magnesium sulfate, filtered and evaporated to dryness to afford 3-(7-methoxy-indol-1-yl)-3-pyridin-3-yl-propan-1-ol as an oil which was purified by column chromatography (ethyl acetate-hexane 3:7).

Step 4

3-(7-Methoxy-indol-1-yl)-3-pyridin-3-yl-propan-1-ol

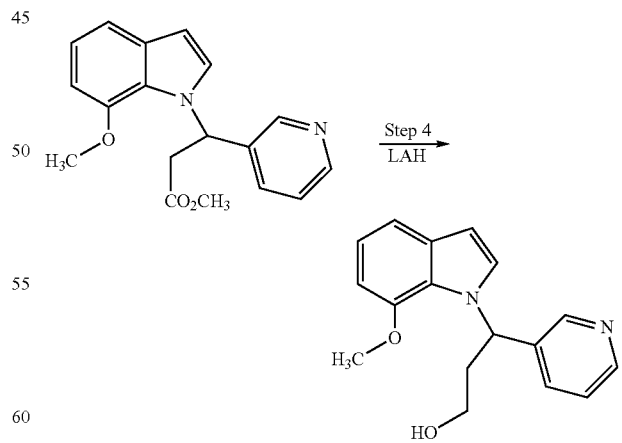

To a solution of 3-(7-methoxy-indol-1-yl)-3-pyridin-3-yl-propionic acid methyl ester (0.290 g) in THF (10 ml) was added a solution of lithium aluminum hydride (1 M in THF, 1 ml) at 0° C. The reaction mixture was stirred for 2 hours at room temperature. To the solution was added sodium sulfate decahydrate (1 g) and stirring was continued until no more bubbling was observed. The suspension was filtered through Celite and the filtrate was evaporated to dryness. The residue was purified by chromatography on silica gel eluting with ethyl acetate to give 3-(7-methoxy-indol-1-yl)-3-pyridin-3-yl-propan-1-ol (0.178 g) as an oil, (M+H=283).

Step 5

[3-(7-Methoxy-indol-1-yl)-3-pyridin-3-yl-propyl]-methyl-amine

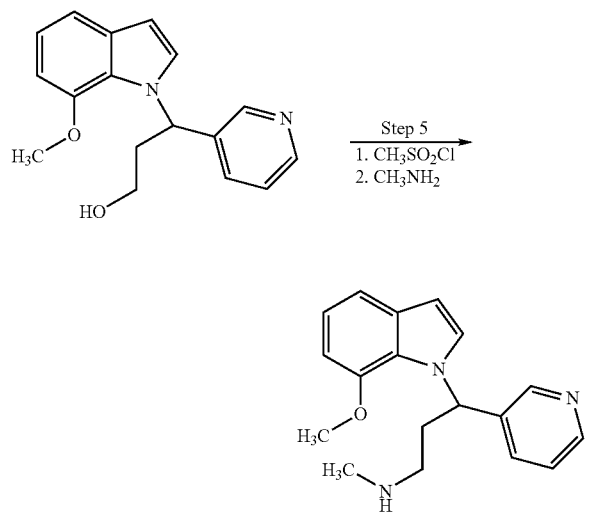

To a solution of 3-(7-methoxy-indol-1-yl)-3-pyridin-3-yl-propan-1-ol in dichloromethane (10 ml) was added triethylamine (0.086 g) followed by methanesulfonyl chloride (0.071 g) dropwise at 0° C. The mixture was stirred for 30 minutes at the same temperature and then the reaction was quenched by partitioning between water and dichloromethane. The organic layer was washed with bicarbonate solution, dried and evaporated to dryness. The crude product was taken up in an ethanolic solution of methyl amine (33%, 4 ml), stirred for 30 minutes at room temperature and then at 100° C. in a microwave reactor. After cooling, the solvents were removed, the crude product was partitioned between dichloromethane and bicarbonate solution, and the organic layer separated. The resulting residue was purified by chromatography on silica gel eluting with mixtures of dichloromethane, methanol and ammonium hydroxide to give 0.088 g of [3-(7-methoxy-indol-1-yl)-3-pyridin-3-yl-propyl]-methyl-amine.

Example 14

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt/wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 15

Screening for Human Serotonin Transporter (hSERT) Antagonists Using a Scintillation Proximity Assay (SPA)

The screening assay of this example was used to determine the affinity of ligands at the hSERT transporter by competition with [$^3$H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 µg/ml G418 and 2 mM L-Glutamine) and incubated at 37° C. with 5% $CO_2$. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube ($7.5 \times 10^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay $IC_{50}/K_i$ determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the [$^3$H]-Citalopram radioligand was added at 50 µl/well. Membrane and beads were prepared to a ratio of 10 µg:0.7 mg, with 0.7 mg PVT-WGA Amersham beads (Cat# RPQ0282V) added per well. 130 µl of the membrane:bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{max - min}{1 + (IC50/x)^n} + min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for human serotonin transporter. For example, [3-(4-methoxy-1H-indol-3-yl)-3-phenyl-propyl]-methyl-amine exhibited an $IC_{50}$ of approximately 8.9 using the above assay.

Example 16

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine.

As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 µg/ml G418 and 2 mM L-Glutamine) and incubated at 37° C. with 5% $CO_2$. Cells were released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube ($7.5 \times 10^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v) and stored at −80° C.

$^3$[H] Nisoxetine radioligand (Amersham Cat. # TRK942 or Perkin Elmer Cat. # NET1084, specific activity: 70-87 Ci/mmol, stock concentration: 1.22 e-5 M, final concentration: 8.25 e-9 M), and 50 mM Tris-HCl, 300 mM NaCl, (pH 7.4) buffers were used for Scintillation Proximity Assay $IC_{50}$/$K_i$ determination. Compounds of the invention were diluted from 101 mM to 0.1 nM FAC (10 point curves, whole log/half log dilutions) via a Beckman Biomek 2000 using a serial dilution protocol. The test compounds were then transferred (20 µl/well) and the radioligand was added at 50 µl/well. Membrane and beads were prepared to a ratio of 10 µg:0.7 mg, with 0.7 mg PVT-WGA Amersham beads (Cat# RPQ0282V) added per well. 130 µl of the membrane:bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{max - min}{1 + (IC50/x)^n} + min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human norepinephrine transporter. For example, [3-(4-methoxy-1H-indol-3-yl)-3-phenyl-propyl]-methyl-amine exhibited an $IC_{50}$ of approximately 7.3 using the above assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

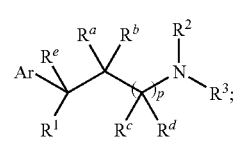

or a pharmaceutically acceptable salt thereof,
wherein:
  p is 1;
  Ar is:
    indolyl selected from indol-1-yl, indol-2-yl and indol-3-yl, each optionally substituted;
    2,3-dihydroindolyl selected from 2,3-dihydroindol-1-yl, 2,3-dihydroindol-2-yl and 2,3-dihydroindol-3-yl, each optionally substituted;
    indazolyl selected from indazol-1-yl, indazol-2-yl and indazol-3-yl, each optionally substituted;
    benzimidazolyl selected from benzimidazol-1-yl and benzimidazol-2-yl, each optionally substituted;
    benzofuranyl selected from benzofuran-2-yl and benzofuran-3-yl, each optionally substituted;
    benzothiophenyl selected from benzothiophen-2-yl and benzothiophen-3-yl, each optionally substituted;
    optionally substituted benzoxazol-2-yl; or
    optionally substituted benzothiazol-2-yl;
  $R^1$ is:
    aryl selected from phenyl and naphthyl, each optionally substituted;
    heteroaryl selected from thienyl, furanyl, pyridinyl, pyrimidinyl, pyridazinyl, pyrazinyl, oxazolyl, thiazolyl, isoxazolyl, isothiazolyl, imidazolyl, pyrazolyl quinolinyl and isoquinolinyl, each optionally substituted;
    optionally substituted arylalkyl;
    optionally substituted heteroarylalkyl;
    cycloalkyl;
    cycloalkylmethyl; or
    branched alkyl;
  one of $R^2$ and $R^3$ is hydrogen and the other is alkyl;
  $R^a$ is:
    hydrogen;
    fluoro; or
    alkyl;
  $R^b$ is:
    hydrogen;
    alkyl;
    hydroxy;
    alkoxy;

fluoro; or hydroxyalkyl;

$R^c$ and $R^d$ each independently is:

hydrogen; or alkyl; and $R^e$ is hydrogen or alkyl.

2. The compound of claim 1, wherein $R^a$, $R^b$, $R^c$ and $R^d$ are hydrogen.

3. The compound of claim 2, wherein $R^e$ is hydrogen.

4. The compound of claim 3, wherein $R^1$ is aryl or heteroaryl.

5. The compound of claim 1, wherein one of $R^2$ and $R^3$ is hydrogen and the other is methyl.

6. The compound of claim 1, wherein said compound is of formula

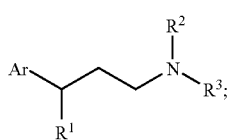

II or a pharmaceutically acceptable salt thereof, wherein:

Ar, $R^1$, $R^2$ and $R^3$ are as recited in claim 1.

7. The compound of claim 6, wherein $R^1$ is phenyl or pyridyl, each optionally substituted.

8. The compound of claim 7, wherein Ar is: indol-1-yl; indol-2-yl; indol-3-yl; 2,3-dihydroindol-1-yl; indazol-1-yl; indazol-2-yl; or indazol-3-yl; each optionally substituted one, two or three or four times with alkyl, alkoxy, halo, haloalkyl, haloalkoxy, cyano, nitro, hydroxyalkyl, alkoxyalkyl, heteroalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —(CH$_2$)$_q$—S(O)$_r$R$^f$; —(CH$_2$)$_q$—NR$^g$R$^h$; —(CH$_2$)$_q$—C(=O)—NR$^g$R$^h$; —(CH$_2$)$_q$—C(=O)—C(=O)—NR$^g$R$^h$; —(CH$_2$)$_q$—SO$_2$—NR$^g$R$^h$; —(CH$_2$)$_q$—N(R$^f$)—C(=O)—R$^i$; —(CH$_2$)$_q$—C(=O)—R$^i$; or —(CH$_2$)$_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy.

9. The compound of claim 8, wherein Ar is: indol-1-yl; indol-2-yl; or indol-3-yl; each optionally substituted one, two or three times with alkyl, alkoxy, halo, haloalkyl, haloalkoxy, cyano, hydroxyalkyl, alkoxyalkyl, heteroalkyl, benzyloxy, cycloalkoxy, cycloalkylalkoxy, alkylsulfonyloxy, optionally substituted thienyl, optionally substituted pyrazolyl, optionally substituted pyridinyl, morpholinocarbonyl, —(CH$_2$)$_q$—S(O)$_r$R$^f$; —(CH$_2$)$_q$—NR$^g$R$^h$; —(CH$_2$)$_q$—C(=O)—NR$^g$R$^h$; —(CH$_2$)$_q$—C(=O)—C(=O)—NR$^g$R$^h$; —(CH$_2$)$_q$—SO$_2$—NR$^g$R$^h$; —(CH$_2$)$_q$—N(R$^f$)—C(=O)—R$^i$; —(CH$_2$)$_q$—C(=O)—R$^i$; or —(CH$_2$)$_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy.

10. The compound of claim 9, wherein Ar is: indol-1-yl; indol-2-yl; or indol-3-yl; each optionally substituted.

11. The compound of claim 9, wherein Ar is: indazol-1-yl; indazol-2-yl; or indazol-3-yl; each optionally substituted.

12. The compound of claim 6, wherein said compound is of the formula III:

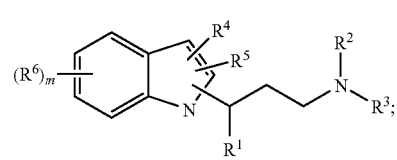

III wherein:

m is from 0 to 4;

$R^4$ and $R^5$ each independently is: hydrogen; alkyl, alkoxy, halo, haloalkyl, haloalkoxy, cyano, nitro, hydroxyalkyl, alkoxyalkyl, heteroalkyl, benzyloxy, cycloalkoxy, cycloalkylalkoxy, optionally substituted thienyl, optionally substituted pyrazolyl, morpholinocarbonyl, —(CH$_2$)$_q$—S(O)$_r$R$^f$; —(CH$_2$)$_q$—NR$^g$R$^h$; —(CH$_2$)$_q$—C(=O)—NR$^g$R$^h$; —(CH$_2$)$_q$—C(=O)—C(=O)—NR$^g$R$^h$; —(CH$_2$)$_q$—SO$_2$—NR$^g$R$^h$; —(CH$_2$)$_q$—N(R$^f$)—C(=O)—R$^i$; —(CH$_2$)$_q$—C(=O)—R$^i$; or —(CH$_2$)$_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy;

each $R^6$ is independently: alkyl, alkoxy, halo, haloalkyl, haloalkoxy, cyano, nitro, hydroxyalkyl, alkoxyalkyl, heteroalkyl, benzyloxy, cycloalkoxy, cycloalkylalkoxy, optionally substituted thienyl, optionally substituted pyrazolyl, morpholinocarbonyl, —(CH$_2$)$_q$—S(O)$_r$R$^f$; —(CH$_2$)$_q$—NR$^g$R$^h$; —(CH$_2$)$_q$—C(=O)—NR$^g$R$^h$; —(CH$_2$)$_q$—C(=O)—C(=O)—NR$^g$R$^h$; —(CH$_2$)$_q$—SO$_2$—NR$^g$R$^h$; —(CH$_2$)$_q$—N(R$^f$)—C(=O)—R$^i$; —(CH$_2$)$_q$—C(=O)—R$^i$, or —(CH$_2$)$_q$—N(R$^f$)—SO$_2$—R$^g$; where q is 0 or 1, r is from 0 to 2, R$^f$, R$^g$, and R$^h$ each independently is hydrogen or alkyl, and each R$^i$ is independently hydrogen, alkyl, hydroxy, or alkoxy; and $R^1$, $R^2$ and $R^3$ are as recited in claim 6.

13. The compound of claim 12, wherein $R^1$ is optionally substituted phenyl or optionally substituted pyridinyl.

14. The compound of claim 13, wherein one of $R^2$ and $R^3$ is hydrogen and the other is methyl.

15. The compound of claim 14, wherein m is 0, 1 or 2 and $R^6$ is halo, alkyl, alkoxy or cyano.

16. The compound of claim 14, wherein m is 1, and $R^6$ is halo or alkoxy at the 4- or 7 position of the indole ring system.

17. The compound of claim 14, wherein $R^4$ and $R^5$ are hydrogen.

18. The compound of claim 12, wherein said compound is of formula IV:

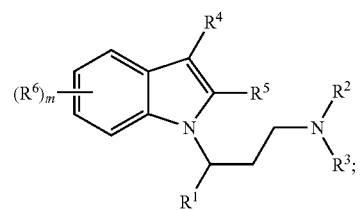

IV and wherein m, $R^1$, $R^2$, $R^3$, $R^4$, $R^5$ and $R^6$ are as recited in claim 12.

19. The compound of claim 12, wherein said compound is of formula I:

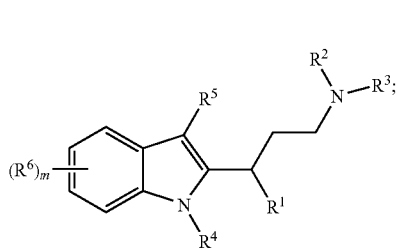

and wherein m, $R^1$, $R^2$, $R^3$, $R^4$, $R^5$ and $R^6$ are as recited in claim 12.

20. The compound of claim 12, wherein said compound is of formula VI:

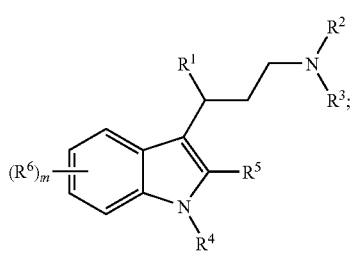

and wherein m, $R^1$, $R^2$, $R^3$, $R^4$, $R^5$ and $R^6$ are as recited in claim 12.

21. The compound of claim 12, wherein said compound is of formula VIa or VIb:

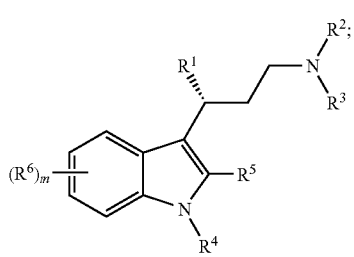

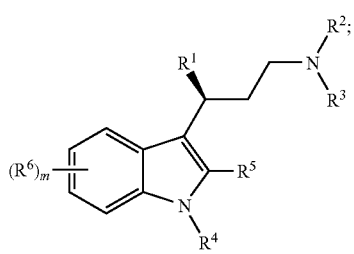

and wherein m, $R^1$, $R^2$, $R^3$, $R^4$, $R^5$ and $R^6$ are as recited in claim 12.

22. The compound of claim 12, wherein said compound is of formula VII:

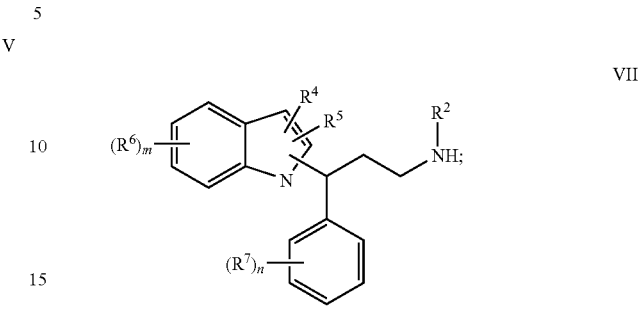

wherein:
n is from 0 to 4;
each $R^7$ independently is halo, alkyl, haloalkyl, alkoxy, or cyano, or two of $R^7$ may form an alkylene dioxy; and
m, $R^2$, $R^4$, $R^5$, and $R^6$ are as recited in claim 12.

23. The compound of claim 22, wherein said compound is of formula VIII:

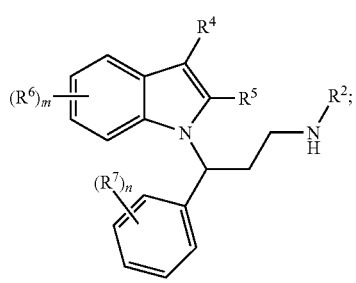 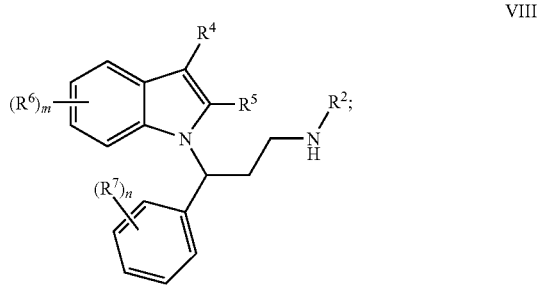

and wherein m, n, $R^2$, $R^4$, $R^5$, $R^6$ and $R^7$ are as recited in claim 22.

24. The compound of claim 22, wherein said compound is of formula IX:

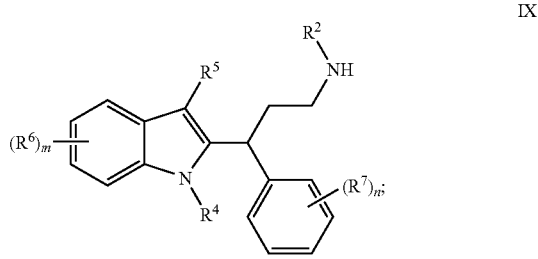

and wherein m, n, $R^2$, $R^4$, $R^5$, $R^6$ and $R^7$ are as recited in claim 22.

25. The compound of claim 22, wherein said compound is of formula X:

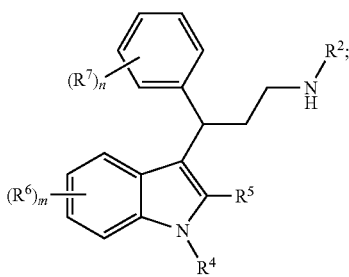

X and wherein m, n, $R^2$, $R^4$, $R^5$, $R^6$ and $R^7$ are as recited in claim 22.

26. The compound of claim 25, wherein said compound is of formula Xa or Xb:

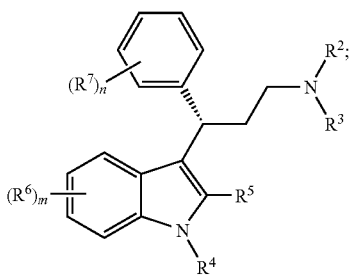

Xa

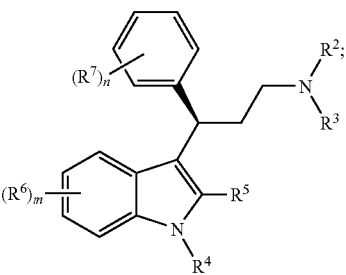

Xb and wherein m, n, $R^2$, $R^4$, $R^5$, $R^6$ and $R^7$ are as recited in claim 25.

27. A pharmaceutical composition, comprising a compound of claim 1 together with a pharmaceutically acceptable carrier.

28. A method for treating a disease mediated by serotonin and norepinephrine neurotransmission, said disease selected from depression and anxiety, said method comprising administering to a subject in need thereof an effective amount of a compound of claim 1.

* * * * *